US012807645B2

(12) United States Patent
Stupp et al.

(10) Patent No.: US 12,807,645 B2
(45) Date of Patent: Nov. 24, 2026

(54) METHODS FOR ASSEMBLING PEPTIDES INTO PEPTIDE AMPHIPHILE NANOFIBERS

(71) Applicant: Northwestern University, Evanston, IL (US)

(72) Inventors: Samuel I. Stupp, Chicago, IL (US); Ruomeng Qiu, Skokie, IL (US)

(73) Assignee: Northwestern University, Evanston, IL (US)

( * ) Notice: Subject to any disclaimer, the term of this patent is extended or adjusted under 35 U.S.C. 154(b) by 1080 days.

(21) Appl. No.: 17/995,784

(22) PCT Filed: Apr. 8, 2021

(86) PCT No.: PCT/US2021/026330
§ 371 (c)(1),
(2) Date: Oct. 7, 2022

(87) PCT Pub. No.: WO2021/207460
PCT Pub. Date: Oct. 14, 2021

(65) Prior Publication Data

US 2023/0287045 A1 Sep. 14, 2023

Related U.S. Application Data

(60) Provisional application No. 63/007,579, filed on Apr. 9, 2020.

(51) Int. Cl.

| | |
|---|---|
| ***C07K 7/06*** | (2006.01) |
| ***A61P 31/14*** | (2006.01) |
| *A61K 38/00* | (2006.01) |
| *B82Y 5/00* | (2011.01) |

(52) U.S. Cl.
CPC ................ *C07K 7/06* (2013.01); *A61P 31/14* (2018.01); *A61K 38/00* (2013.01); *B82Y 5/00* (2013.01)

(58) Field of Classification Search
CPC .................................. C07K 7/06; B82Y 5/00
See application file for complete search history.

(56) References Cited

U.S. PATENT DOCUMENTS

| | | | |
|---|---|---|---|
| 7,030,167 | B2 | 4/2006 | Gunther |
| 7,371,719 | B2 | 5/2008 | Stupp et al. |
| 7,452,679 | B2 | 11/2008 | Stupp et al. |
| 7,491,690 | B2 | 2/2009 | Stupp et al. |
| 7,534,761 | B1 | 5/2009 | Stupp et al. |
| 7,544,661 | B2 | 6/2009 | Stupp et al. |
| 7,554,021 | B2 | 6/2009 | Stupp et al. |
| 7,683,025 | B2 | 3/2010 | Stupp et al. |
| 7,745,708 | B2 | 6/2010 | Stupp et al. |
| 7,838,491 | B2 | 11/2010 | Stupp et al. |
| 7,851,445 | B2 | 12/2010 | Stupp et al. |
| 8,063,014 | B2 | 11/2011 | Stupp et al. |
| 8,076,295 | B2 | 12/2011 | Hulvat et al. |
| 8,080,262 | B2 | 12/2011 | Lee et al. |
| 8,114,834 | B2 | 2/2012 | Hsu et al. |
| 8,114,835 | B2 | 2/2012 | Mata et al. |
| 8,124,583 | B2 | 2/2012 | Stupp et al. |
| 8,138,140 | B2 | 3/2012 | Stupp et al. |
| 8,236,800 | B2 | 8/2012 | Degrado et al. |
| 8,450,271 | B2 | 5/2013 | Shah et al. |
| 8,512,693 | B2 | 8/2013 | Capito et al. |
| 8,546,338 | B2 | 10/2013 | Donners et al. |
| 8,580,923 | B2 | 11/2013 | Stupp et al. |
| 8,748,569 | B2 | 6/2014 | Stupp et al. |
| 8,772,228 | B2 | 7/2014 | Stupp et al. |
| 9,011,914 | B2 | 4/2015 | Wong Po Foo et al. |
| 9,040,626 | B2 | 5/2015 | Chien et al. |
| 9,044,514 | B2 | 6/2015 | Xu et al. |
| 2009/0156505 | A1 | 6/2009 | Stupp et al. |
| 2018/0111963 | A1* | 4/2018 | Stupp ..................... A61K 38/08 |

FOREIGN PATENT DOCUMENTS

WO WO 2015/048747 4/2015

OTHER PUBLICATIONS

Shah, R. N., et al., Feb. 2010, Supramolecular design of self-assembling nanofibers for cartilage regeneration, PNAS 107(8):3293-3298.*

Qiu, R., et al., 2023, Supramolecular Nanofibers Block SARS-CoV-2 Entry into Human Host Cells, ACS Appl. Mater. Interfaces 15:26340-26348.*

Li, et al. Peptide-based supramolecular hydrogels for delivery. Bioeng Transl Med. Sep. 2016;1(3):306-322.

Sundar, et al. Delivery of Therapeutics and Molecules using Self-Assembled Peptides. Curr Med Chem. 2014;21(22):2469-79.

Dehsorkhi et al. Self-Assembling Amphiphilic Peptides. J Pept Sci. Jul. 2014;20(7):453-67.

Extended European Search Report for EP 21785057.7, mailed Apr. 4, 2024, 8 pages.

International Search Report and Written Opinion for PCT/US21/26330. Mailed Oct. 5, 2021. 12 pages.

Chen et al., Drug-Bearing Supramolecular Filament Hydrogels as Anti-Inflammatory Agents. Theranostics. May 12, 2017;7(7):2003-2014.

Cinar et al., Local delivery of doxorubicin through supramolecular peptide amphiphile nanofiber gels. Biomater Sci. Dec. 20, 2016;5(1):67-76.

Cui et al., Amino acid sequence in constitutionally isomeric tetrapeptide amphiphiles dictates architecture of one-dimensional nanostructures. J Am Chem Soc. Sep. 3, 2014;136(35):12461-8.

De Bona et al., Design and synthesis of new trehalose-conjugated pentapeptides as inhibitors of Abeta(1-42) fibrillogenesis and toxicity. J Pept Sci. Mar. 2009;15(3):220-8.

Gelain et al., Slow and sustained release of active cytokines from self-assembling peptide scaffolds. J Control Release. Aug. 3, 2010;145(3):231-9.

(Continued)

*Primary Examiner* — Jeffrey S Parkin
(74) *Attorney, Agent, or Firm* — Casimir Jones, S.C.; Rikki A. Hullinger

(57) ABSTRACT

Provided herein are peptide amphiphile co-assemblies and uses thereof. In particular, the technology relates to peptides that are intercalated into peptide amphiphile nanofibers, and methods of delivering peptide drugs using the same.

8 Claims, 55 Drawing Sheets

Specification includes a Sequence Listing.

(56) References Cited

OTHER PUBLICATIONS

Han et al., Amyloid β-42 induces neuronal apoptosis by targeting mitochondria. Mol Med Rep. Oct. 2017;16(4):4521-4528.
Israelachvili. Intermolecular and surface forces; 2nd ed.; Academic: London San Diego, 1992. TOC only. 2 pages.
Korevaar et al., Pathway selection in peptide amphiphile assembly. J Am Chem Soc. Jun. 18, 2014;136(24):8540-3.
Kuida et al., Decreased apoptosis in the brain and premature lethality in CPP32-deficient mice. Nature. Nov. 28, 1996;384(6607):368-72.
Lee et al., Gel scaffolds of BMP-2-binding peptide amphiphile nanofibers for spinal arthrodesis. Adv Healthc Mater. Jan. 7, 2015;4(1):131-141.
Levine. Thioflavine T interaction with synthetic Alzheimer's disease beta-amyloid peptides: detection of amyloid aggregation in solution. Protein Sci. Mar. 1993;2(3):404-10.
Matson et al., Nanostructure-templated control of drug release from peptide amphiphile nanofiber gels. Soft Matter. Apr. 7, 2012;8(13):3586-3595.
Mayo et al., A recipe for designing water-soluble, beta-sheet-forming peptides. Protein Sci. Jul. 1996;5(7):1301-15.
Meisburger et al., X-ray Scattering Studies of Protein Structural Dynamics. Chem Rev. Jun. 28, 2017;117(12):7615-7672.
Ortony et al., Internal dynamics of a supramolecular nanofibre. Nat Mater. Aug. 2014;13(8):812-6.
Rossi et al., Analysis of protein-ligand interactions by fluorescence polarization. Nat Protoc. Mar. 2011;6(3):365-87.
Soto et al., Beta-sheet breaker peptides inhibit fibrillogenesis in a rat brain model of amyloidosis: implications for Alzheimer's therapy. Nat Med. Jul. 1998;4(7):822-6.
Tantakitti et al., Energy landscapes and functions of supramolecular systems. Nat Mater. Apr. 2016;15(4):469-76.
Viola et al., Amyloid β oligomers in Alzheimer's disease pathogenesis, treatment, and diagnosis. Acta Neuropathol. Feb. 2015;129(2):183-206.
Walsh et al., Naturally secreted oligomers of amyloid beta protein potently inhibit hippocampal long-term potentiation in vivo. Nature. Apr. 4, 2002;416(6880):535-9.
Xu. Cross-beta-sheet structure in amyloid fiber formation. J Phys Chem B. Sep. 17, 2009;113(37):12447-55.
Zhang et al., A self-assembly pathway to aligned monodomain gels. Nat Mater. Jul. 2010;9(7):594-601.
Zhang et al., Self-assembled Tat nanofibers as effective drug carrier and transporter. ACS Nano. Jul. 23, 2013;7(7):5965-77.

* cited by examiner

P3:PA 2:1

P2:PA 2:1

| Sample | Average width (nm) |
|---|---|
| P4/PA 0.4:1 | 14.88 |
| P4/PA 2:1 | 18.11 |
| P1/PA 0.4:1 | 8.25 |
| P1/PA 2:1 | 8.16 |
| PA | 9.19 |

METHODS FOR ASSEMBLING PEPTIDES INTO PEPTIDE AMPHIPHILE NANOFIBERS

RELATED APPLICATIONS

This application is a national phase application under 35 U.S.C. § 371 of PCT International Application No.: PCT/US2021/026330, filed on Apr. 18, 2021, which claims priority to U.S. Non-Provisional Patent Application No. 63,007,579, filed Apr. 9, 2020, the entire contents of which are incorporated herein by reference for all purposes.

INCORPORATION-BY-REFERENCE OF MATERIAL SUBMITTED ELECTRONICALLY

The computer readable sequence listing filed herewith, titled "NWEST-38426-252_SQL", created Oct. 6, 2022, having a file size of 53,979 bytes, is hereby incorporated by reference in its entirety.

FIELD OF INVENTION

Provided herein is technology relating to peptide amphiphile co-assemblies and uses thereof. In particular, the technology relates to free peptides that are intercalated into peptide amphiphile nanofibers, and methods of delivering peptide drugs using the same.

BACKGROUND

Peptides represent viable therapeutic options for the treatment or prevention of a wide range of diseases or conditions. However, peptide delivery can be inefficient for a variety of reasons, including enzymatic degradation of the peptide prior to release in the desired area within a subject. Accordingly, what is needed are novel methods for delivery of peptides to a subject that protect the peptide from the external environment and thus reduce the risk of preemptive degradation of the peptide.

SUMMARY

In some aspects, provided herein are nanostructures comprising a peptide amphiphile and a free peptide. In some embodiments, the peptide amphiphile comprises a hydrophobic tail, a structural peptide segment, and a charged peptide segment. In some embodiments, the free peptide and the peptide amphiphile are non-covalently co-assembled within the nanostructure. In some embodiments, the hydrophobic tail comprises a chain of 8-24 carbons. In some embodiments, the structural peptide segment has a propensity for forming β-sheet conformations. In some embodiments, the structural peptide segment comprises $V_2A_2$, $V_2A_3$, $V_3A_3$, or VEV.

The charged peptide segment may comprise 1-4 glutamic acid residues. For example, the charged peptide segment may comprise E, EE, EEE, or EEEE (SEQ ID NO: 43). In some embodiments, the charged peptide segment may comprise 1-4 lysine residues. For example, the charged peptide segment may comprise K, KK, KKK, or KKKK (SEQ ID NO: 44).

In some embodiments, the free peptide comprises a charged head and a β-sheet forming sequence. For example, the free peptide may comprise an amyloid-β fragment or derivative thereof. In some embodiments, the free peptide comprises LPFFD (SEQ ID NO: 45) or KLVFF (SEQ ID NO: 46). In some embodiments, the peptide amphiphile comprises a hydrophobic tail conjugated to a segment comprising $V_3A_3E_3$ (SEQ ID NO: 47) and the free peptide comprises LPFFD (SEQ ID NO: 45) or KLVFF (SEQ ID NO: 46). For example, in some embodiments the peptide amphiphile comprises $C_{16}$-$V_3A_3E_3$ (SEQ ID NO: 47) and the free peptide comprises LPFFD (SEQ ID NO: 45) or KLVFF (SEQ ID NO: 46).

In some embodiments, the free peptide comprises a peptide that prevents entry of a virus into a host cell. For example, the peptide may bind to a viral protein, bind to a binding partner of a viral protein, disrupt activation of a viral protein, and/or disrupt fusion of a viral protein with a host cell membrane. In some embodiments, the viral protein is a component of a virus belonging to the coronaviridae family. In some embodiments, the virus is SARS-CoV-2. In some embodiments, the free peptide binds to the spike protein of SARS-CoV-2.

In some embodiments, the free peptide comprises an amino acid sequence having at least 80% sequence identity to any one of SEQ ID NO:1-SEQ ID NO: 42. In some embodiments, the free peptide comprises an amino acid sequence having at least 80% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. For example, the free peptide may comprise an SBP-1 peptide having the amino acid sequence of SEQ ID NO: 1. In some embodiments, the peptide amphiphile comprises $C_{16}$-$V_3A_3E_3$ (SEQ ID NO: 47), $C_{16}$-$FV_2A_3E_3$ (SEQ ID NO: 48), $C_{16}$-VEVE (SEQ ID NO: 49), or $C_{16}$-$V_3A_3K_3$ (SEQ ID NO: 50) and the free peptide comprises an SBP-1 peptide having the amino acid sequence of SEQ ID NO: 1.

In some aspects, the nanostructure is a nanofiber. In some aspects, provided herein are compositions comprising a nanostructure as described herein. Such compositions may be used in various methods. For example, compositions comprising a nanostructure as described herein may be used in methods of treating or preventing a neurodegenerative disorder in a subject. The neurodegenerative disorder may be, for example, Alzheimer's disease, Parkinson's disease, or Huntington's disease. As another example, compositions comprising a nanostructure as described herein may be used in methods of treating or preventing a viral infection in a subject. The viral infection may be caused by SARS-CoV-2.

In some aspects, provided herein are methods of treating or preventing a neurodegenerative disorder in a subject. The neurodegenerative disorder may be Alzheimer's disease, Parkinson's disease, or Huntington's disease. In some embodiments, the method comprises providing to the subject a composition comprising a nanostructure comprising a peptide amphiphile and a free peptide. In some embodiments, the peptide amphiphile comprises a hydrophobic tail, a structural peptide segment, and a charged peptide segment. In some embodiments, the free peptide and the peptide amphiphile are non-covalently co-assembled within the nanostructure. In some embodiments, the free peptide comprises an amyloid-β fragment or derivative thereof. For example, the free peptide may comprise LPFFD (SEQ ID NO: 45) or KLVFF (SEQ ID NO: 46). In some embodiments, the structural peptide segment has a propensity for forming β-sheet conformations. In some embodiments, the structural peptide segment comprises $V_2A_2$ (SEQ ID NO: 51), $V_2A_3$ (SEQ ID NO: 52), or $V_3A_3$ (SEQ ID NO: 53). In some embodiments, the charged peptide segment comprises EE, EEE, or EEEE (SEQ ID NO: 43).

In some aspects, provided herein are methods of treating or preventing a viral infection in a subject. The methods comprise providing to the subject a composition comprising a nanostructure comprising a peptide amphiphile and a free peptide. In some embodiments, the peptide amphiphile comprises a hydrophobic tail, a structural peptide segment, and a charged peptide segment. In some embodiments, the free peptide and the peptide amphiphile are non-covalently co-assembled within the nanostructure. In some embodiments, the free peptide comprises an amino acid sequence having at least 80% sequence identity to any one of SEQ ID NO:1-SEQ ID NO: 42. In some embodiments, hydrophobic tail comprises a chain of 8-24 carbons. In some embodiments, the structural peptide segment has a propensity for forming β-sheet conformations. In some embodiments, the structural peptide segment comprises $V_2A_2$ (SEQ ID NO: 51), $V_2A_3$ (SEQ ID NO: 52), $V_3A_3$ (SEQ ID NO: 53), or VEV. The charged peptide segment may comprise E, EE, EEE, EEEE (SEQ ID NO: 43), K, KK, KKK, or KKKK (SEQ ID NO: 44). In some embodiments, the peptide amphiphile comprises $C_{16}$-$V_3A_3E_3$ (SEQ ID NO: 47), $C_{16}$-$FV_2A_3E_3$ (SEQ ID NO: 48), $C_{16}$-VEVE (SEQ ID NO: 49), or $C_{16}$-$V_3A_3K_3$ (SEQ ID NO: 50). The methods may be used to treat or prevent any viral infection. In some embodiments, the viral infection is an infection with SARS-CoV-2. In some embodiments, the free peptide comprises SEQ ID NO: 1.

For any of the methods described herein, the subject may be human.

BRIEF DESCRIPTION OF THE DRAWINGS

(FIG. 1A) Chemical structures of peptide amphiphile (PA), composed of alkyl tail and β-sheet forming sequence with charged residues, and free peptides of sequentially reduced β-sheet forming residues, P1-P3. (FIG. 1B) Schematic representation of mixing monomeric peptide (in red) and PA (in gray) to form co-assemblies in aqueous environment. Water molecules remaining within the nanostructure are shown in blue. (FIG. 1C) Cryogenic transmission electron microscopy (Cryo-TEM) of P1 co-assembled PA at 0.4:1 molar ratio. Scale bar is 100 nm.

FIG. 4. Internal structure and peptide dynamics of free peptide/PA co-assemblies controlled via stoichiometry.

(FIG. 12**F) Transmission FTIR spectra of annealed P1/$^{13}$C-PA assemblies ($^{13}$C-PA: $C_{15}H_{31}$CO-VV*VAAAEEE (SEQ ID NO: 47) —$NH_2$).

FIG. 23. Effect of P4/PA co-assemblies on primary mouse cortical neurons survival.

FIG. 24. Effect of annealing on P4/PA co-assemblies' bioactivity.

DEFINITIONS

Figure 1A:
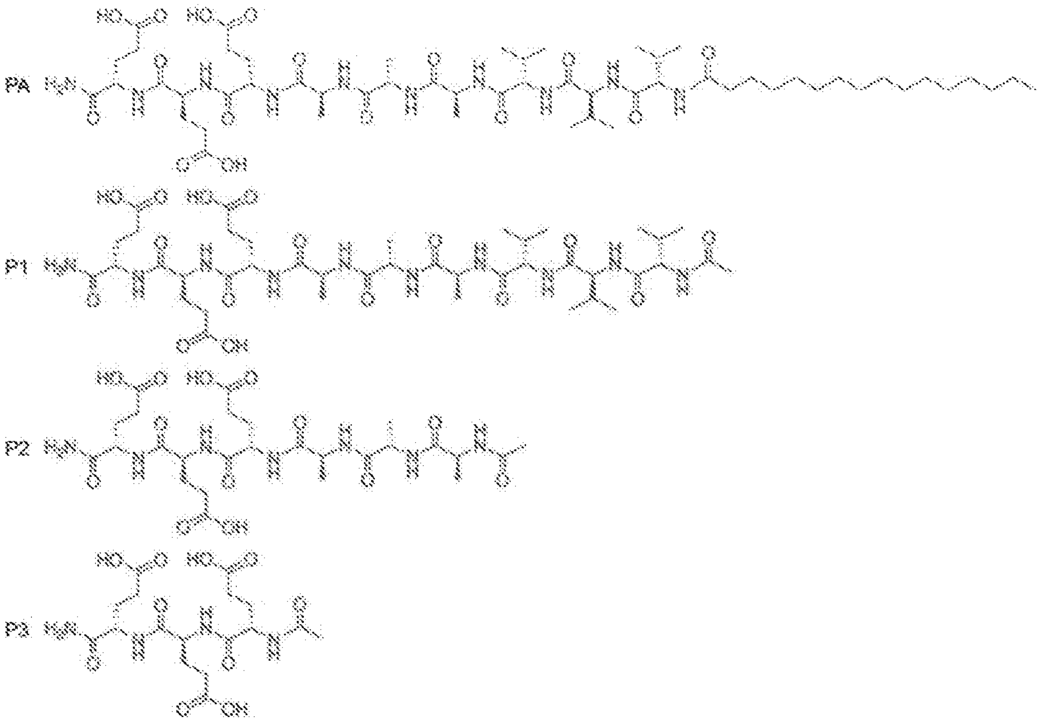
FIG. 1A-C show chemical structures and morphology of free peptide/PA co-assemblies.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodemosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "scaffold" refers to a material capable of supporting growth and differentiation of a cell.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both). The peptide amphiphile may express a net charge at physiological pH, either a net positive or negative net charge, or may be zwitterionic (i.e., carrying both positive and negative charges).

As used herein and in the appended claims, the term "lipophilic moiety" or "hydrophobic moiety" refers to the moiety (e.g., an acyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system. Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. In some embodiments, the hydrophobic component is a palmitoyl group. However, other lipophilic groups may be used in place of the acyl chain such as steroids, phospholipids and fluorocarbons.

As used interchangeably herein, the terms "structural peptide" or "structural peptide segment" refer to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural peptide segments of adjacent structural peptide segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the terms "treat," "treatment," and "treating" refer to reducing the amount or severity of a particular condition, disease state, or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and preventing" refer to reducing the likelihood of a particular condition or disease state from occurring in a subject not presently experiencing or afflicted with the condition or disease state. The terms do not necessarily indicate complete or absolute prevention. For example preventing a disease or condition refers to reducing the likelihood of the disease or condition from occurring in a subject not presently experiencing or diagnosed with the disease or condition. In order to prevent a disease or condition, a composition or method need only reduce the likelihood of the disease or condition, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "free peptide" refers to a peptide that is not a peptide amphiphile (e.g., not covalently attached to a hydrophobic moiety (e.g., a non-peptide hydrophobic moiety)). The free peptide may be part of a co-assembly comprising a peptide amphiphile and the free peptide.

DETAILED DESCRIPTION

In some aspects, provided herein are peptide amphiphiles (PAs) and co-assemblies (e.g. nanostructures, such as nanofibers) comprising the same. In some embodiments, the co-assemblies further comprise a free peptide, such as a therapeutic peptide. Further provided herein are methods of use of the PAs and co-assemblies provided herein.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —$NH_2$ group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH2, and —$NH_2$.

In some embodiments, peptide amphiphiles comprise a hydrophobic segment (i.e. a hydrophobic tail) linked to a peptide. In some embodiments, the peptide comprises a structural peptide segment. In some embodiments, the structural peptide segment is a hydrogen-bond-forming segment, or beta-sheet-forming segment. In some embodiments, the structural peptide segment has the propensity to form random coil structures. In some embodiments, the peptide comprises a charged segment (e.g., acidic segment, basic segment, zwitterionic segment, etc.). In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules may self-assemble (e.g., into cylindrical micelles (a.k.a., nanofibers)) to bury the lipophilic segment in their core. In some embodiments, the peptide amphiphiles and one or more peptides may co-assemble into a nanofiber. In some embodiments, the structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30). In some embodiments, the hydrophobic segment comprises a palmitoyl group.

In some embodiments, PAs comprise one or more peptide segments. The peptide segment may comprise natural amino acids, modified amino acids, unnatural amino acids, amino acid analogs, peptidomimetics, or combinations thereof. In some embodiments, the peptide segment comprises at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide segment may comprise one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises E, EE, EEE, or EEEE (SEQ ID NO: 43). For example, the acidic peptide segment may comprise E. For example, in some embodiments an acidic peptide segment comprises EE. In some embodiments, an acidic peptide segment comprises EEE. In other embodiments, an acidic peptide segment comprises EEEE (SEQ ID NO: 43).

In some embodiments, peptide amphiphiles comprise a basic peptide segment. For example, in some embodiments, the basic peptide segment comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, a basic peptide segment comprises $(Xb)_{1-7}$, wherein each Xb is independently R, H, and/or K. In some embodiments, the basic peptide segment comprises K, KK, KKK, or KKKK (SEQ ID NO: 44). In some embodiments, the basic peptide segment comprises $K_3$.

In some embodiments, peptide amphiphiles comprises a structural peptide segment. In some embodiments, the structural peptide segment is a beta-sheet-forming segment. In some embodiments, the structural peptide segment displays weak hydrogen bonding and has the propensity to form random coil structures rather than rigid beta-sheet conformations. In some embodiments, the structural peptide segment is rich in one or more of H, I, L, F, V, G, and A residues. In some embodiments, the structural peptide segment comprises an alanine- and valine-rich peptide segment (e.g., VVAA (SEQ ID NO: 51), VVVAAA (SEQ ID NO: 53), AAVV (SEQ ID NO: 54), AAAVVV (SEQ ID NO: 55), or other combinations of V and A residues, etc.). In some embodiments, the structural peptide segment comprises 4 or more consecutive A and/or V residues, or conservative or semi-conservative substitutions thereto. In some embodiments, the structural peptide segment comprises $V_2A_2$ (SEQ ID NO: 51). In some embodiments, the structural peptide segment comprises $V_3A_3$ (SEQ ID NO: 53). In some embodiments, the structural peptide segment comprises $V_2A_3$ (SEQ ID NO: 52). In some embodiments, the structural peptide segment comprises VEV.

In some embodiments, peptide amphiphiles comprise a spacer or linker segment. In some embodiments, the spacer or linker segment is located at the opposite terminus of the peptide from the hydrophobic segment. In some embodiments, the linker segment is a non-peptide linker. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C═O groups (e.g., $CH2(O(CH_2)_2)_2NH$, $CH2(O(CH_2)_2)_2NHCO(CH_2)_2CCH$, etc.). In some embodiments, a spacer or linker further comprises additional bioactive groups, substituents, branches, etc. In some embodiments, the linker segment is a single glycine (G) residue.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural peptide segment, etc.). In some embodiments, the characteristics of a supramolecular structure (e.g. co-assembly of a PA and a free peptide) additionally depend on the identify and characteristics of the peptide. For example, nanofibers, nanospheres, intermediate shapes, and other supramolecular structures are achieved by adjusting the identity of the PA component parts and/or peptide. In some embodiments, characteristics of supramolecular nanostructures of PAs (e.g. co-assemblies) are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural peptide segment (e.g., comprising VVAA (SEQ ID NO: 51), VVVAAA (SEQ ID NO: 53), etc.); and (c) a charged segment (e.g., comprising EE, EEE, EEEE (SEQ ID NO: 43), etc.). In some embodiments, any PAs within the scope described herein, comprising the components described herein, or within the skill of one in the field, may find use herein.

In some embodiments, a peptide amphiphile comprises (e.g., from C-terminus to N-terminus or from N-terminus to C-terminus): charged segment (e.g., comprising EE, EEE, EEEE (SEQ ID NO: 43), etc.)—structural peptide segment (e.g., VVAA (SEQ ID NO: 51), VVVAAA (SEQ ID NO: 53), etc.)—hydrophobic tail (e.g., comprising an alkyl chain of 8-24 carbons).

In some embodiments, a PA further comprises an attachment segment or residue (e.g., K, F) for attachment of one or more segments of the PA to another segment. For example, the PA may further comprise a residue for attachment the hydrophobic tail to the peptide portion of the PA. In some embodiments, the hydrophobic tail is attached to a lysine side chain. In some embodiments, the hydrophobic tail is attached to a phenylalanine side chain.

In some embodiments, the peptide amphiphile comprises a hydrophobic tail conjugated to $V_3A_3E_3$ (SEQ ID NO: 47), $FV_2A_3E_3$ (SEQ ID NO: 48), VEVE (SEQ ID NO: 49), or $V_3A_3K_3$ (SEQ ID NO: 50).

In some embodiments, provided herein are nanostructures, such as nanofibers, assembled from any combination of the peptide amphiphiles described herein. In some embodiments, a nanostructure (e.g. nanofiber) is prepared by the self-assembly of the PAs described herein. In some embodiments, the nanostructure additionally comprises a free peptide, such as a therapeutic peptide. A nanofiber or other supramolecular structure comprising a peptide amphiphile and a free peptide as described herein is referred to as a co-assembly.

In some embodiments, the co-assembly (e.g. nanostructure) further comprises a free peptide (e.g., in addition to PAs). For example, the co-assembly may comprise a therapeutic peptide for the treatment of a disease or condition. Any suitable free peptide may be used, provided that the free peptide effectively forms a co-assembly (e.g. a nanostructure, such as a nanofiber) with a peptide amphiphile described herein. In some embodiments, the free peptide is amphiphilic.

In some embodiments, the free peptide comprises a β-sheet forming sequence. In some embodiments, the β-sheet forming sequence is the same as the structural peptide segment of the peptide amphiphile. In some embodiments, the β-sheet forming sequence is similar to the structural peptide segment of the peptide amphiphile. For example, the β-sheet forming sequence may have 50% or more sequence identity (e.g. 50%, 60%, 70%, 80%, 90%, 95%, or more) to the structural peptide segment of the peptide amphiphile.

In some embodiments, the β-sheet forming sequence of the free peptide is rich in one or more of H, I, L, F, V, G, and A residues. In some embodiments, the β-sheet forming sequence of the free peptide comprises an alanine- and valine-rich peptide segment (e.g., VVAA (SEQ ID NO: 51), VVVAAA (SEQ ID NO: 53), AAVV (SEQ ID NO: 54), AAAVVV (SEQ ID NO: 55), or other combinations of V and A residues, etc.). In some embodiments, the β-sheet forming sequence of the free peptide comprises 4 or more consecutive A and/or V residues, or conservative or semi-conservative substitutions thereto. In some embodiments, β-sheet forming sequence of the free peptide comprises $V_3A_3$ (SEQ ID NO: 53). In some embodiments, the β-sheet forming sequence of the free peptide comprises $A_3$. Suitable β-sheet forming sequences are exemplified in P1, P2, P3, ad P4.

In some embodiments, the free peptide comprises a charged head. The charged head may be acidic, basic, or zwitterionic. In some embodiments, the charged head of the free peptide is the same as the charged segment of the peptide amphiphile. In some embodiments, the charged head of the free peptide is similar to the charged segment of the peptide amphiphile. For example, the charged head of the free peptide may have 50% or more sequence identity (e.g. 50%, 60%, 70%, 80%, 90%, 95%, or more) to the charged segment of the peptide amphiphile. In some embodiments, the free peptide comprises a β-sheet forming sequence and a charged head.

In some embodiments, the charged head is acidic. For example, the charged head may comprise one or more (e.g., 1, 2, 3, 4, 5, 6, 7, or more) acidic residues (D and/or E) in sequence. In some embodiments, the charged head comprises up to 7 residues in length and comprises at least 50% acidic residues. In some embodiments, a charged head comprises $(Xa)_{1-7}$, wherein each Xa is independently D or E. In some embodiments, the charged head comprises $E_{2-4}$. For example, in some embodiments the charged head comprises EE, EEE, or EEEE (SEQ ID NO: 43).

In some embodiments, charged head is basic. For example, in some embodiments, the charged head comprises one or more (e.g., 1, 2, 3, 4, 5, 6, 7, or more) basic residues (R, H, and/or K) in sequence. In some embodiments, the charged head comprises up to 7 residues in length and comprises at least 50% basic residues. In some embodiments, the charged head comprises $(Xb)_{1-7}$, wherein each Xb is independently R, H, and/or K.

In some embodiments, the free peptide comprises $V_3A_3E_3$ (SEQ ID NO: 47). In some embodiments, the free peptide comprises $A_3E_3$ (SEQ ID NO: 56).

In some embodiments, the free peptide is a therapeutic peptide. In some embodiments, the free peptide is a therapeutic peptide with potential for treating neurodegenerative disease, such as neurodegenerative disease characterized by protein aggregation (e.g. amyloid aggregation). In some embodiments, the free peptide comprises a β-amyloid fragment or a derivative thereof. For example, the free peptide may comprise the β-amyloid fragment derivative LPFFD (SEQ ID NO: 45). As another example, the free peptide may comprise the β-amyloid fragment derivative KLVFF (SEQ ID NO: 46). In some embodiments, the free peptide additionally comprises a suitable N-terminal and C-terminal group bound to the β-amyloid fragment. For example, the free peptide may comprise Ac-LPFFD (SEQ ID NO: 45) —NH2.

In some embodiments, the free peptide is a therapeutic peptide with potential for treating and/or preventing infection, such as a viral infection in a subject. For example, the free peptide may be an immunogenic peptide for use in the prevention of infection in a subject. Any suitable immunogenic peptide that forms a co-assembly with a peptide amphiphile described herein may be used. As another example, the free peptide may be a suitable peptide for the treatment of infection in a subject.

In some embodiments, the free peptide may be a therapeutic peptide that prevents one or more steps necessary for viral infection of a host cell, thereby preventing viral infection in a subject. In some embodiments, the free peptides may be selected to act extracellularly, i.e. to target early steps of viral replication, such as viral envelope glycoprotein activation, receptor attachment, or fusion. Accordingly, the nanostructure comprising the therapeutic peptide would not need to penetrate the cell membrane to be effective.

In some embodiments, the free peptide may bind to a specific portion of a viral protein. In some embodiments, the free peptide may bind to a binding partner of the viral protein. For example, the free peptide may bind to a portion of the virus or to a portion of a binding partner of the virus necessary for viral entry into a cell. For example, SARS-CoV-2 infection relies on the SARS-CoV-2 spike protein binding to angiotensin-converting enzyme 2 (ACE2) on host cells to initiate cellular entry. Blocking the interactions between spike protein and ACE2 offers promising opportunities for developing therapeutics for the prevention or treatment of COVID-19. Accordingly, in some embodiments the free peptide may be a suitable peptide that binds to the spike protein or ACE2, thereby disrupting interactions between SARS-CoV-2 and ACE2. For example, the free peptide may be a suitable peptide that binds to the receptor binding domain (RBD) of the spike protein of SARS-CoV-2, thereby disrupting interactions between SARS-CoV-2 and ACE2 and preventing entry into the cell. In other embodiments, the free peptide may be a suitable peptide that binds to the spike protein (i.e. the S-protein) in an area away from the RBD.

In some embodiments, the free peptide is SBP-1 or a derivative thereof. For example, the free peptide may comprise an SBP-1 protein having an amino acid sequence of IEEQAKTFLDKFNHEAEDLFYQS (SEQ ID NO: 1). The free peptide may be an SBP-1 derivative having at least 80% sequence identity (e.g. 80%, 81%, 82%, 83%, 84%, 85%, 85%, 86%, 87%, 88%, 89%, 90%, 91%, 92%, 93%, 94%, 95%, 96%, 97%, 98%, 99%, or 100%) with SEQ ID NO: 1.

In some embodiments, the free peptide comprises the amino acid sequence of an ACE2 mimic peptide. Such ACE2 mimic peptides would also bind to the spike protein (e.g. RBD of the spike protein) of SARS-CoV-2, thereby preventing entry of SARS-CoV-2 into the cell. Suitable ACE2 mimic peptides includes, for example, EEQAKTFLDKFNHEAEDLFYQSS (SEQ ID NO: 2), and EEQAKTFLDKFNHEAEDLFYQSSLASWNYNTNITEE (SEQ ID NO: 3).

Other suitable peptides that may be used to inhibit the interaction between SARS-CoV-2 and ACE2 include, for example, PTTKFMLKYDENGTITDAVDC (SEQ ID NO: 4), YQDVNCTDVSPTAIHADQLTP (SEQ ID NO: 5), QYGSFCT(A)QLNRALSGIAAVEQ (SEQ ID NO: 6), DEDLEELERLYRKAEEVAKEAKDASRRGDDERAKEQMERAMRLFDQVFELAQELQEK QTDGNRQKATHLDKAVKEAADELYQRVRELEEQVMHVLDQVSELAHELLHKLTGEEL ERAAYFNWWATEMMLELIKSDDEREIREIEEEARRILEHLEELARK (SEQ ID NO: 7), ELEEQVMHVLDQVSELAHELLHKLTGEELERAAYFNWWATEMMLELIKSDDEREIREIE EEARRILEHLEELARK (SEQ ID NO: 8), DKEWILQKIYEIMRLLDELGHAEASMRVSDLIYEFMKKGDERLLEEAERLLEEVER (SEQ ID NO: 9), NDDELHMLMTDLVYEALHFAKDEEIKKRVFQLFELADKAYKNNDRQKLEKVVEELKE LLERLLS (SEQ ID NO: 10), YKYRYL (SEQ ID NO: 11), GFLYVYKGYQPI (SEQ ID NO: 12), FYTTTGIGYQPY (SEQ ID NO: 13), STSQKSIVAYTM (SEQ ID NO: 14), ALNCYWPLNDYGFTTTGIGYQPYRVVVLSFEL (SEQ ID NO: 15), or GDYSHCSPLRYYPWWKCTYPDPEGGG (SEQ ID NO: 16). In some embodiments, the free peptide may be peptide having at least 80% sequence identity (e.g. 80%, 81%, 82%, 83%, 84%, 85%, 85%, 86%, 87%, 88%, 89%, 90%, 91%, 92%, 93%, 94%, 95%, 96%, 97%, 98%, 99%, or 100%) with any one of SEQ ID NOs: 2-16.

Activation of the SARS-CoV-2 S protein requires proteolytic cleavage at two sites. First, the S protein is cleaved and primed at the poly-basic S1/S2 site by the host protease furin, which generates two distinct subunits. The second cleavage site is found in the S2 region (S2') and is processed by the plasma membrane-associated protease TMPRSS2. Alternatively, lysosomal cathepsin L can process and activate the S protein independently of furin-mediated priming. Accordingly, free peptides that inhibit these proteases (e.g. furin, TMPRSS2, or cathepsin L) may also be used in a nanostructure described herein to prevent SARS-CoV-2 infection.

Suitable peptides that may inhibit furin, TMPRSS2, or cathepsin L include, for example, RPDFCLEPPYTGPCK-ARIIRYFYNAKAGLCQTFVYGGCRAKRNNFKSAE-DCMRTCGGA (SEQ ID NO: 17), NGAICWGPCPTA-FRQIGNCGHFKVRCCKIR (SEQ ID NO: 18), and NGA-ICWGPCPTAFRQIGNCGRFRVRCCRIR (SEQ ID NO: 19). In some embodiments, the free peptide may be peptide having at least 80% sequence identity (e.g. 80%, 81%, 82%, 83%, 84%, 85%, 85%, 86%, 87%, 88%, 89%, 90%, 91%, 92%, 93%, 94%, 95%, 96%, 97%, 98%, 99%, or 100%) with any one of SEQ ID NOs: 17, 18, or 19.

Another potential strategy to prevent viral infection is to disrupt viral membrane fusion, or the process by which enveloped viruses enter the host cell. For example, viral class I fusion proteins possess HR regions which facilitate viral fusion and entry into the host cell. Accordingly, HR targeting peptides (e.g. peptides that target HR1 or HR2) may disrupt the membrane fusion process and therefore help prevent SARS-CoV-2 infection, or infection with similar viruses including SARS-CoV-1, MERS-CoV, etc. Accordingly, HR targeting peptides may be suitable free peptides for use in the nanostructures and methods described herein. Such suitable free peptides include, for example, VVEQYNQTILNLTSEISTLENKSAELNYTVQKLQTL-IDNINSTLVDLKWL (SEQ ID NO: 20), LTQINTTLLD-LTYEMLSLQQVVKALNESYIDLKEL (SEQ ID NO: 21), SLTQINTTLLDLTYEMLSLQQVVKALNESYIDLKEL (SEQ ID NO: 22), GINASVVNIQKEIDRLNEVAKNL-NESLIDLQELGKYE (SEQ ID NO: 23), ELDSF-KEELDKYFKNHTSPDVDLGDISGINASVVNIQKEID-RLNEVAKNLNESLIDLQELG KYEQYIK (SEQ ID NO: 24), NGIGVTQNVLYENQKQIANQFNKAISQIQES-LTTTSTA (SEQ ID NO: 25), IQKEIDRLNEVAKNLNESL-IDLQELGK (SEQ ID NO: 26), GDISGINASVV-NIQKEIDRLNEVAKNLNESLIDLQELG (SEQ ID NO: 27), YENQKQIANQFNKAISQIQESLTTTSTA (SEQ ID NO: 28), DVDLGD ISGINAS VVNIQKE IDRLNEV AKNLNES LIDLQEL GKYEQYI (SEQ ID NO: 29), ISGI-NAS VVNIQKE IDRLNEV AKNLNES LIDLQEL (SEQ ID NO: 30), SLDQINVTFLDLEYEMKKLEEAIK-KLEESYIDLKEL (SEQ ID NO: 31), DISGINASVV-NIQKEIDRLNEVAKNLNESLIDLQEL (SEQ ID NO: 32), DISGINASWNIQKEIDRLNEVAKNLNESLIDLQE (SEQ ID NO: 33), SLDQINVTFLDLEYEMKKLEEAIK-KLEESYIDLKELGSGSG (SEQ ID NO: 34), ISGINASVV-NIQKEIDRLNEVAKNLNESLIDLQELK (SEQ ID NO: 35), GIGVT(A)QNVLYENQKQIANQF (SEQ ID NO: 36), IQK(E)EIDRLNEVAKNLNESLI (SEQ ID NO: 37), GYHLMSFPQAAPHGVVFLHVTW (SEQ ID NO: 38), GVFVFNGTSWFITQRNFFS (SEQ ID NO: 39), AACE-VAKNLNESLIDLQELGKYEQYIKW (SEQ ID NO: 40), MWKTPTLKYFGGFNFSQIL (SEQ ID NO: 41), and ATAGWTFGAGAALQIPFAMQMAY (SEQ ID NO: 42). In some embodiments, the free peptide may be peptide having at least 80% sequence identity (e.g. 80%, 81%, 82%, 83%, 84%, 85%, 85%, 86%, 87%, 88%, 89%, 90%, 91%, 92%, 93%, 94%, 95%, 96%, 97%, 98%, 99%, or 100%) with any one of SEQ ID NOs: 20-42.

In some embodiments, provided herein are compositions comprising a co-assembly (e.g. a nanostructure) comprising a peptide amphiphile and a free peptide as described herein.

In some embodiments, the ratio of PAs to free peptides in a nanostructure (e.g. nanofiber) determines the mechanical characteristics (e.g., liquid or gel) of the nanostructure material and under what conditions the material will adopt various characteristics (e.g., gelling upon exposure to physiologic conditions, liquifying upon exposure to physiologic conditions, etc.).

In some embodiments, the molar amount of PA exceeds the molar amount of free peptide in the nanostructure. In other embodiments, the molar amount of PA is less than the molar amount of free peptide in the nanostructure. In some embodiments, the molar amounts of free peptide and PA in the nanostructure are about equal (i.e. the molar ratio is 1:1). In some embodiments, the molar ratio of free peptide:PA in the nanostructure ranges from about 0.1:1 to about 5:1. For example, the molar ratio of free peptide:PA in the nanostructure may be about 0.1:1, 0.2:1, 0.3:1, 0.4:1, 0.5:1, 0.6:1, 0.7:1, 0.8:1. 0.9:1, about 1:1, about 1.5:1, about 2:1, about 2.5:1, about 3:1, about 3.5:1, about 4:1, about 4.5:1, or about 5:1.

In some embodiments, the nanostructures described herein are a nanofiber. In some embodiments, a nanofiber described herein exhibits a small cross-sectional diameter (e.g., <25 nm, <20 nm, <15 nm, about 10 nm, etc.). In some embodiments, the small cross-section of the nanofibers (~10 nm diameter) allows the fibers to permeate the brain parenchyma.

In some embodiments, the PAs and co-assemblies (e.g. nanostructures, such as nanofibers) described herein may be incorporated into pharmaceutical compositions for use in methods of treating disease. For example, the PAs and co-assemblies (e.g. nanofibers) described herein may be used for methods of treatment or prevention of neurodegenerative disease in a subject. For example, compositions comprising nanofibers containing suitable β-amyloid fragments or derivatives thereof may be used for methods of treating and/or preventing neurodegenerative disease. Suitable neurodegenerative diseases include diseases characterized by amyloid aggregation. For example, neurodegenerative diseases include Alzheimer's disease, Parkinson's disease, and Huntington's disease.

In some embodiments, PAs and co-assemblies (e.g. nanofibers) described herein may be incorporated into pharmaceutical compositions for use in methods of treating or preventing infection in a subject. For example, the PAs and nanofibers described herein may be used in methods of treatment and/or prevention of viral infection caused by, for example, adenoviridae (e.g. Adenovirus), arenaviridae (e.g. Lassa virus), astroviridae (e.g. Human astrovirus), bunyavirida (e.g. Crimean-Congo hemorrhagic fever virus, Hantaan virus), Caliciviridae (e.g. Norwalk virus), coronaviridae (e.g. coronavirus OC43, coronavirus 229E, coronavirus NL63, coronavirus HKU1, MERS-CoV, SARS-CoV, and SARS-CoV-2 (COVID-19)), filoviridae (e.g. Ebola virus, Marburg virus), flaviviridae (e.g. Hepatitis C virus, yellow fever virus, dengue virus, west nile virus, TBE virus), hepadnaviridae (e.g. Hepatitis B virus), hepeviridae (e.g. Hepatitis E virus), Herpesviridae (e.g. HSV1, HSV2, varicella-zoster virus, Eppstein-Barr virus, Human cytomegalovirus, Human herpesvirus), Orthomyxoviridae (e.g. influenza A virus, influenza B virus), papilloviridae (e.g. human papillomavirus), paramyxoviridae (e.g. measles virus, mumps virus, parainfluenza virus type 1, parainfluenza virus type 2, respiratory syncytial virus), parvoviridae (e.g. parvovirus), picornaviridae (e.g. coxsackievirus, hepatitis A virus, poliovirus, rhinovirus), polyomaviridae (e.g. BK virus, JC virus), poxviridae (e.g. smallpox), reoviridae (e.g. rotavirus, orbivirus, coltivirus, Banna virus), retroviridae (e.g. HIV), rhabdoviridae (e.g. rabies), togaviridae (e.g.

rubella virus), and other enveloped or non-enveloped viruses (e.g. hepatitis D, metapneumovirus, hantavirus, Nipah virus).

The composition may be administered in any suitable amount, depending on factors including the age of the subject, weight of the subject, severity of the disease, and the like. The composition may be administered in combination with other suitable treatments for neurodegenerative disease.

In some embodiments, the compositions herein are formulated for delivery to a subject. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, the PA compositions are administered parenterally. In some embodiments, parenteral administration is by intrathecal administration, intracerebroventricular administration, or intraparenchymal administration. The PA compositions herein can be administered as the sole active agent or in combination with other pharmaceutical agents such as other agents used in the treatment or prevention of neurodegenerative disease in a subject.

EXAMPLES

Example 1

In this example, co-assembly of PAs with a series of short, soluble free peptides in water was investigated. It was hypothesized that molecular amphiphilicity and molecular complementarity would be factors in driving co-assembly. To understand the generalizability of the findings presented herein and the potential of delivering β-amyloid (Aβ) peptide inhibitors, LPFFD (SEQ ID NO: 45) as an exemplary free peptide was used. LPFFD (SEQ ID NO: 45) is amphiphilic in nature and therefore incorporation into β-sheet structure was hypothesized. Finally, the biological functions of the artificial β-sheet co-assemblies was investigated as a promising approach to intervene in neurodegenerative disease.

Figure 1B:
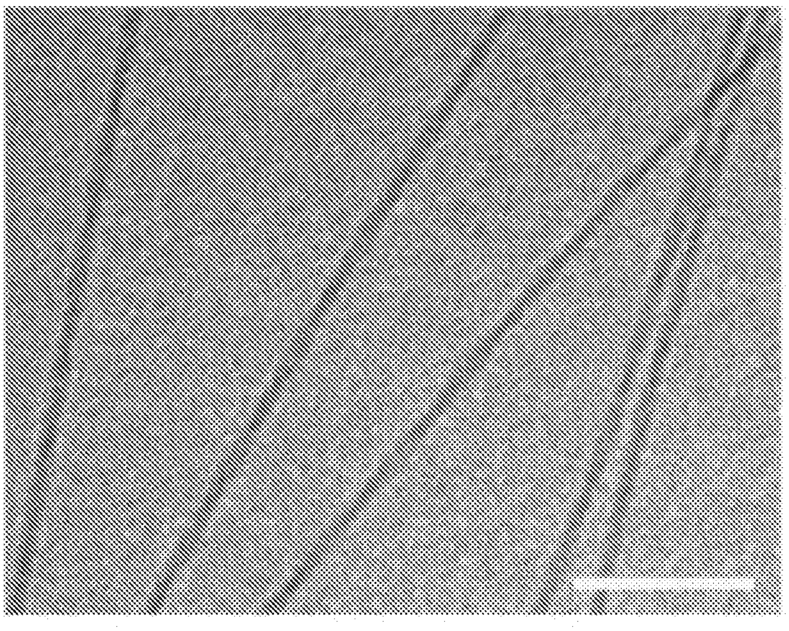
Figure 1C:
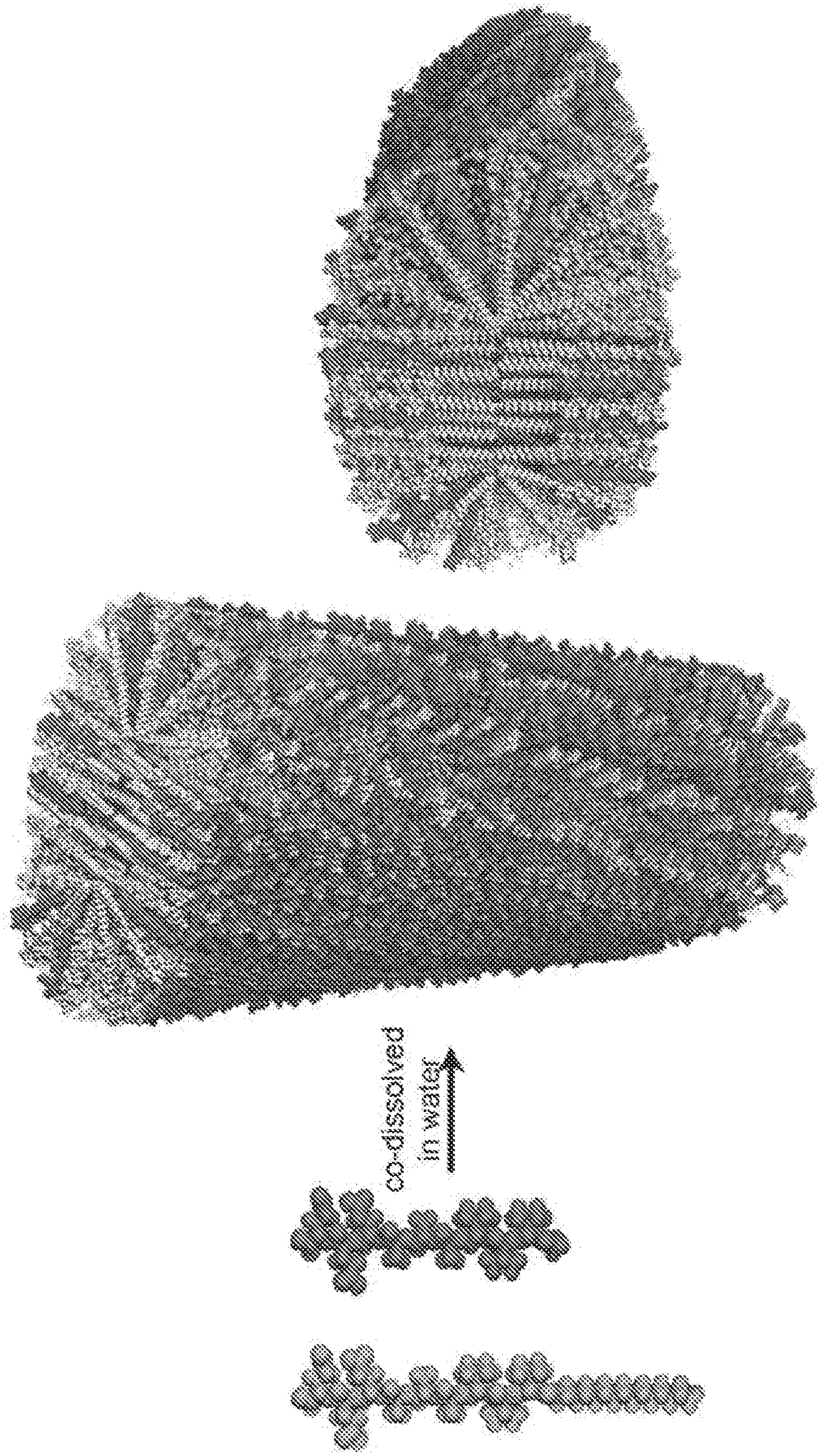
Figure 2:
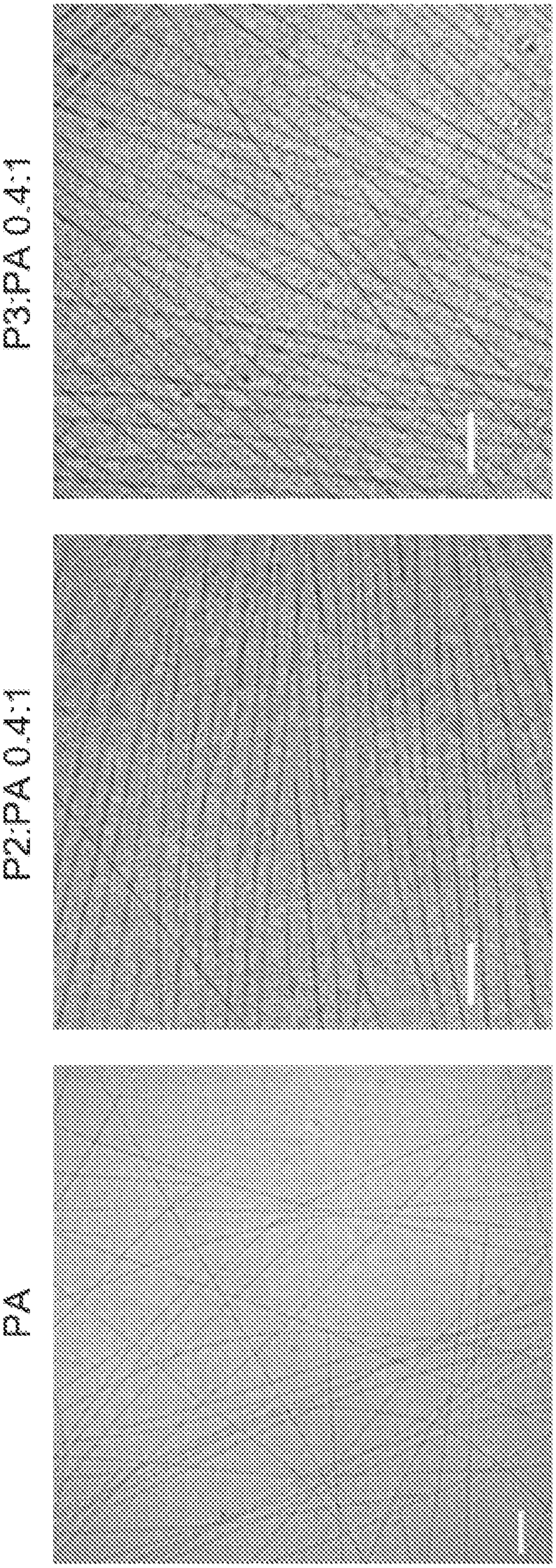
FIG. 2. Cryo-TEM images of aged PA alone (left), P2/PA 0.4:1 (center) and P3/PA 0.4:1 (right), scale bar is 100 nm.
Figure 3B:
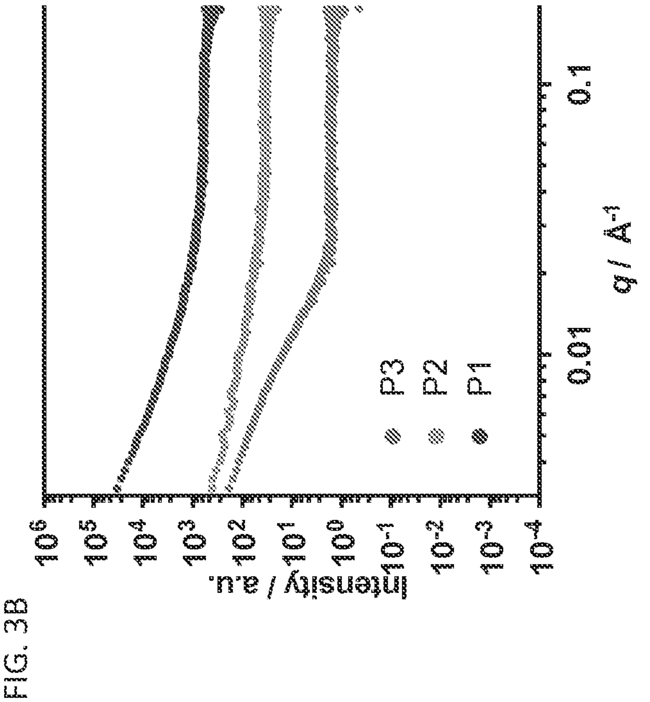
FIG. 3. Small-angel X-ray scattering (SAXS) profiles of P1-P3 co-assembled with PA (FIG. 3A) of 0.4:1 at 10 mM PA and peptide only (FIG. 3B), 10 mM.
Figure 3A:
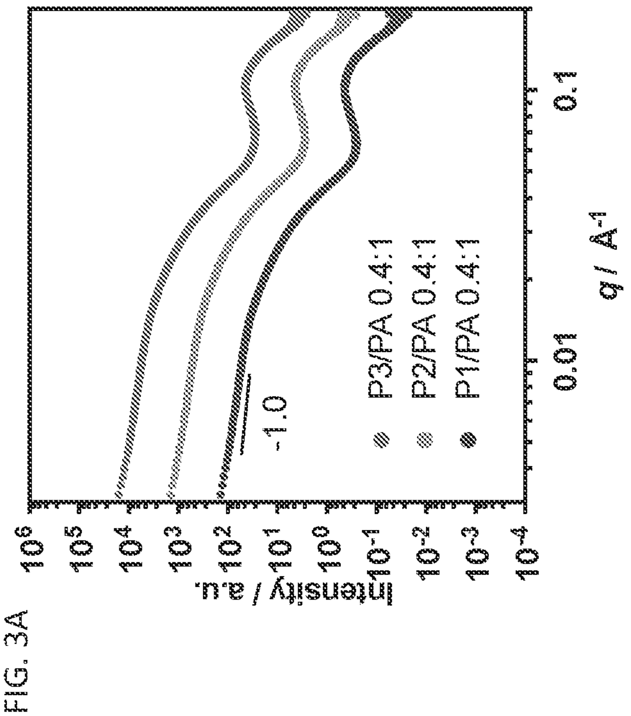

As shown in FIG. 1A, a PA composed of N-palmitoyl group conjugated to $V_3A_3E_3$ (SEQ ID NO: 47) was synthesized. This amphiphilic sequence had strong β-sheet propensity. The hydrophobic N-palmitoyl moiety drives PA self-assembly into nanofilaments (FIG. 2) while the oligopeptide $V_3A_3E_3$ (SEQ ID NO: 47) organizes internal structure through supramolecular β-sheet interactions.[1-3] To explore whether the short peptides that lack a hydrophobic tail can interact with the PA nanostructure and how the varying hydrophobicity of the peptide molecule influences the co-assembly behavior, we synthesized three peptides, $V_3A_3E_3$ (SEQ ID NO: 47) (P1), $A_3E_3$ (SEQ ID NO: 56) (P2) and $E_3$ (P3), with diminishing potential to form β-sheets (FIG. 1A). These peptides, which lack a hydrophobic tail and may form co-assemblies with the PA, may be referred to herein as "free peptides". To ensure complete mixing of the free peptide and PA from the monomeric state, hexafluoro-2-propanol (HFIP) was used to solvate aliphatic chains and hydrophobic residues of the oligopeptide.[4] After HFIP removal, the resulting free peptide/PA mixture was dispersed in water and the pH was adjusted to 7.2 with 1 M NaOH (FIG. 1B). Cryogenic transmission electron microscopy (cryo-TEM) was utilized to characterize the nanostructures formed by the assembled free peptide/PA mixtures at the molar ratio of 0.4:1, which showed slightly twisted nanoribbons with around 8 nm diameter (P1/PA shown in FIG. 1B as well as P2/PA and P3/PA shown in FIG. 2). To corroborate the microscopy results, the 0.4:1 free peptide/PA mixtures, the self-assembled PA alone and free peptide alone were analyzed using solution small-angle X-ray scattering (SAXS). The scattering pattern of the PA alone and the mixtures all showed a slope of −1.0 in the Guinier region, which is indicative of 1D nanostructures formation (FIG. 3A). No significant scattering was observed for the free peptide alone, suggesting that no structures were formed from free peptides (FIG. 3B).

Figure 4B:
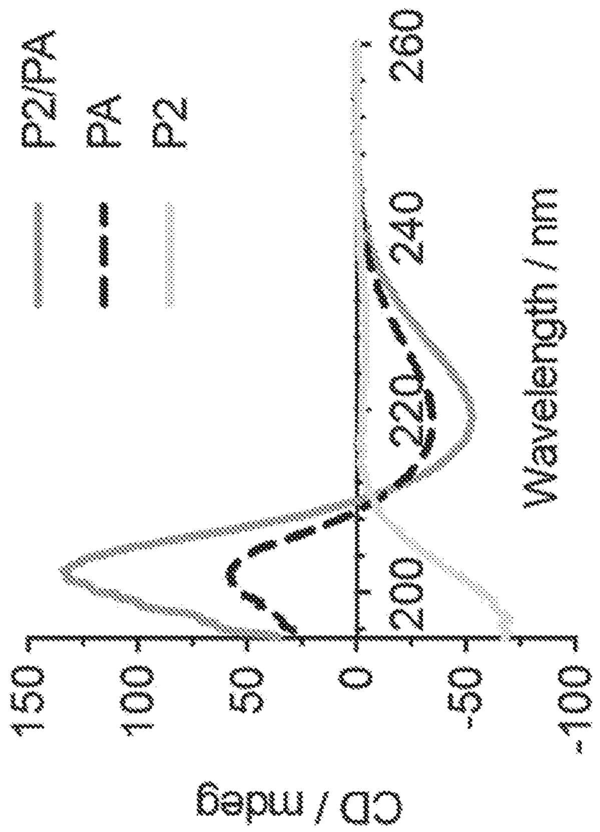
(FIGS. 4A, 4B, and 4C) Circular dichroism (CD) spectra of free peptide alone and free peptide/PA co-assemblies at 0.22 mM PA with 88 mM (0.4 equivalents) peptide.
Figure 4A:
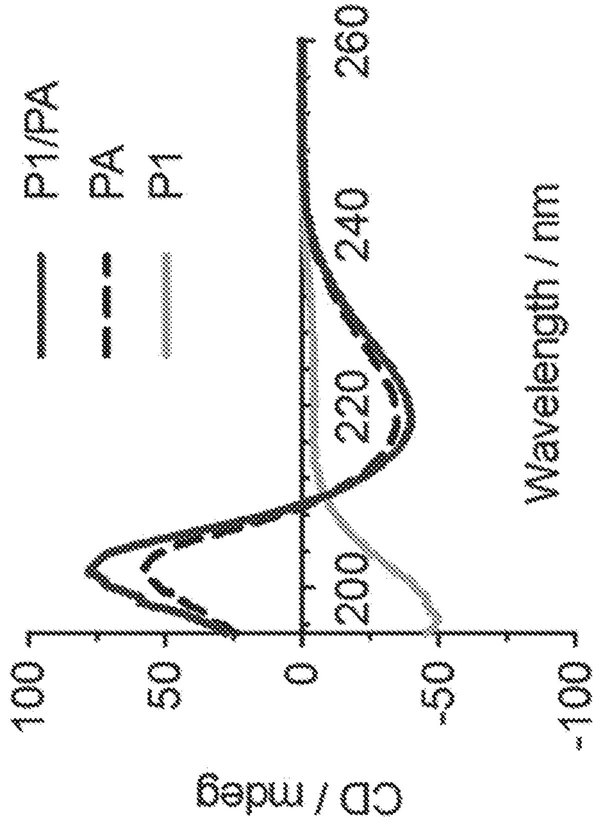
Figure 4C:
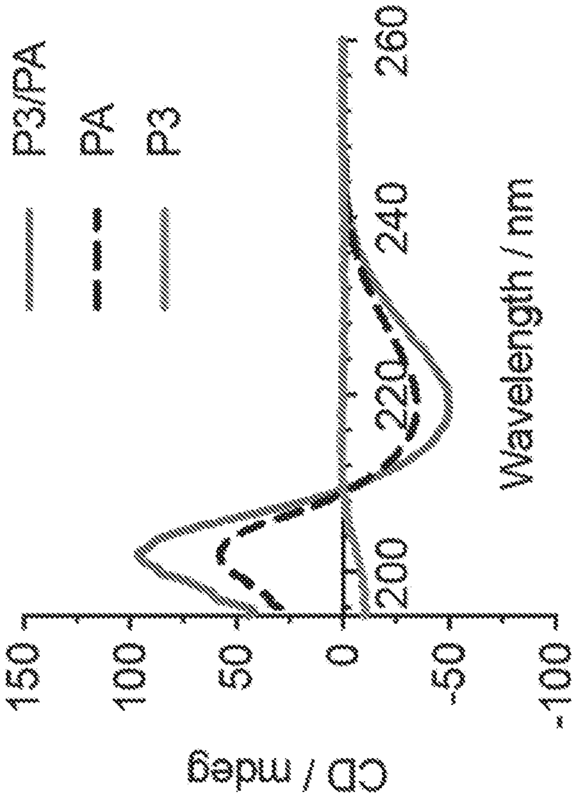

To probe the internal secondary structure of free peptide/PA assemblies, circular dichroism (CD) spectroscopy was performed for free peptide alone, PA alone and free peptide/PA assemblies shown at the molar ratio of 0.4:1 (FIG. 4A-4C). As shown previously,[5] PA alone displayed a negative peak around 220 nm, indicating a β-sheet secondary conformation. All of the free peptide solutions (P1-P3) showed a random coil configuration, indicating that these short peptides lacking the alkyl tail could not form β-sheet structure. Interestingly, the random coil signature observed for the three free peptides disappeared when they were mixed with PA. Alternatively, the 0.4:1 free peptide/PA mixtures displayed a β-sheet signature with stronger negative intensity at 220 nm compared to the PA alone, suggesting the intermolecular association between PA and free peptide.

Figure 4D:
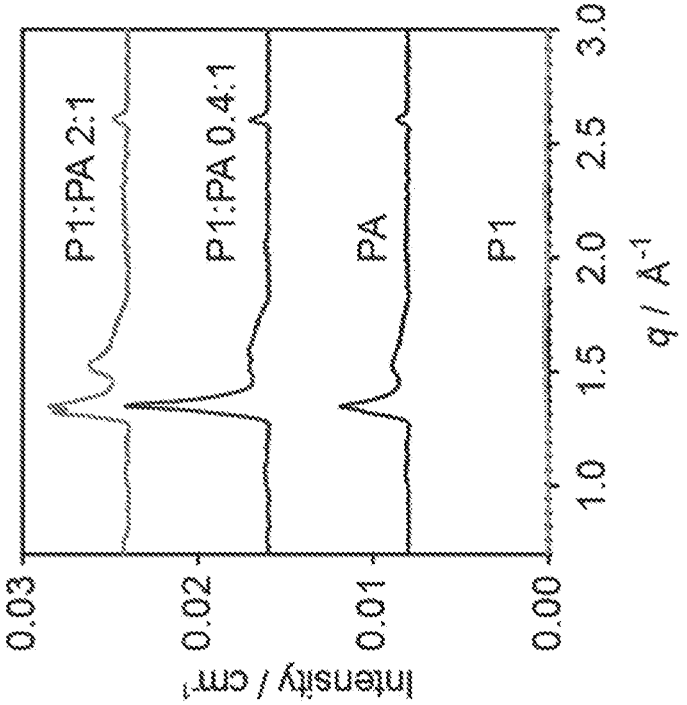
(FIGS. 4D, 4E, and 4F) Wide-angel X-ray scattering (WAXS) profiles of the aqueous samples of free peptide alone, PA alone, and free peptide/PA co-assemblies shows the increased β-sheet character at low free peptide content (0.4:1) and the decreased β-sheet character at high peptide content (2:1). The baselines of PA and peptide/PA co-assemblies were offset by 0.008 cm-1 for each pattern for clarity.
Figure 4E:
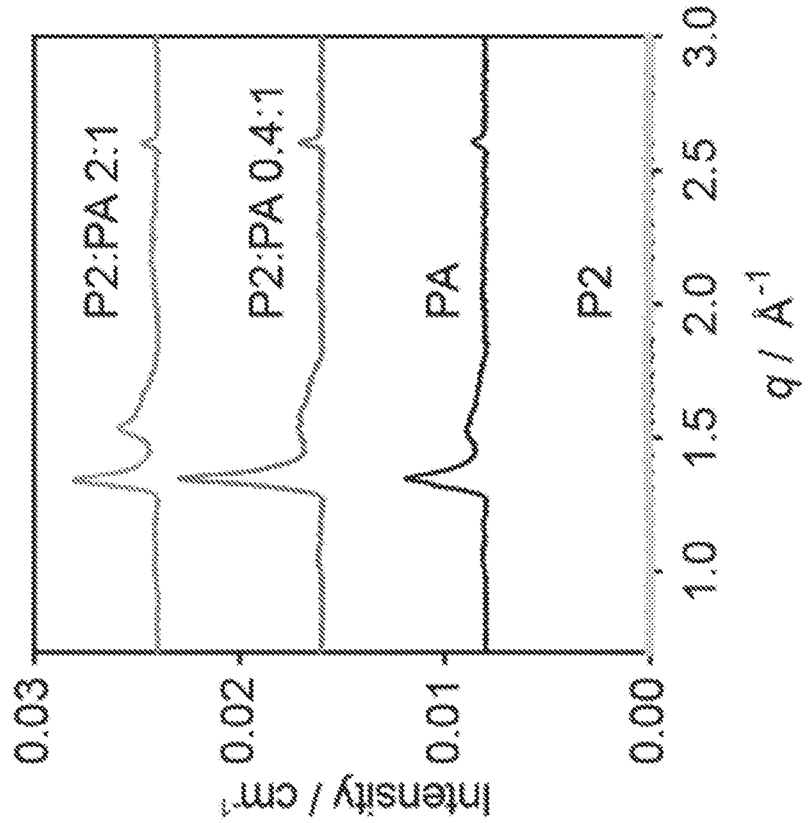
Figure 4F:
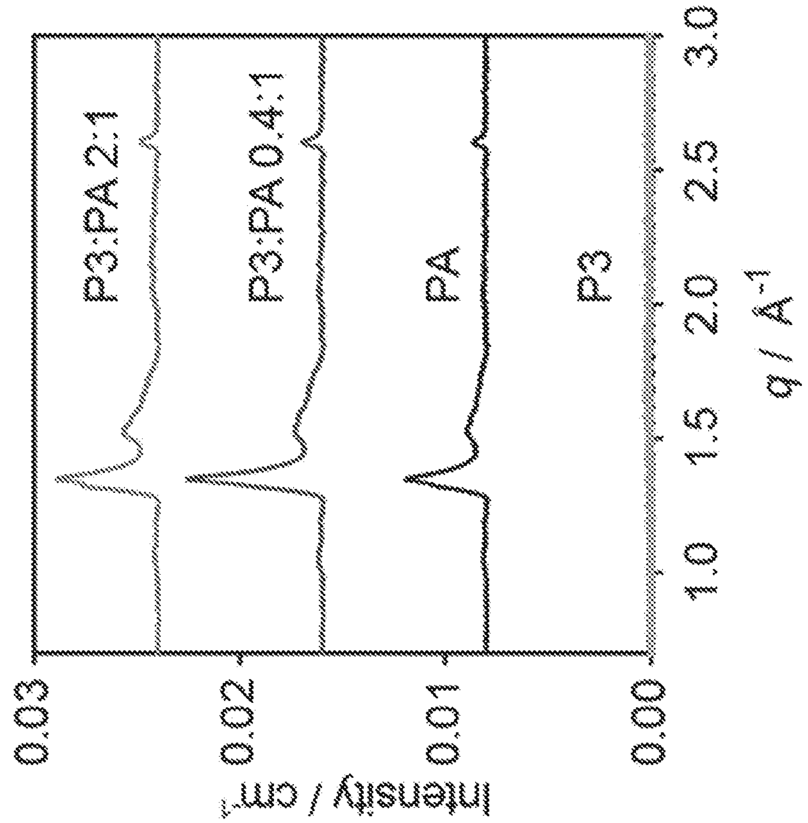
Figure 5:
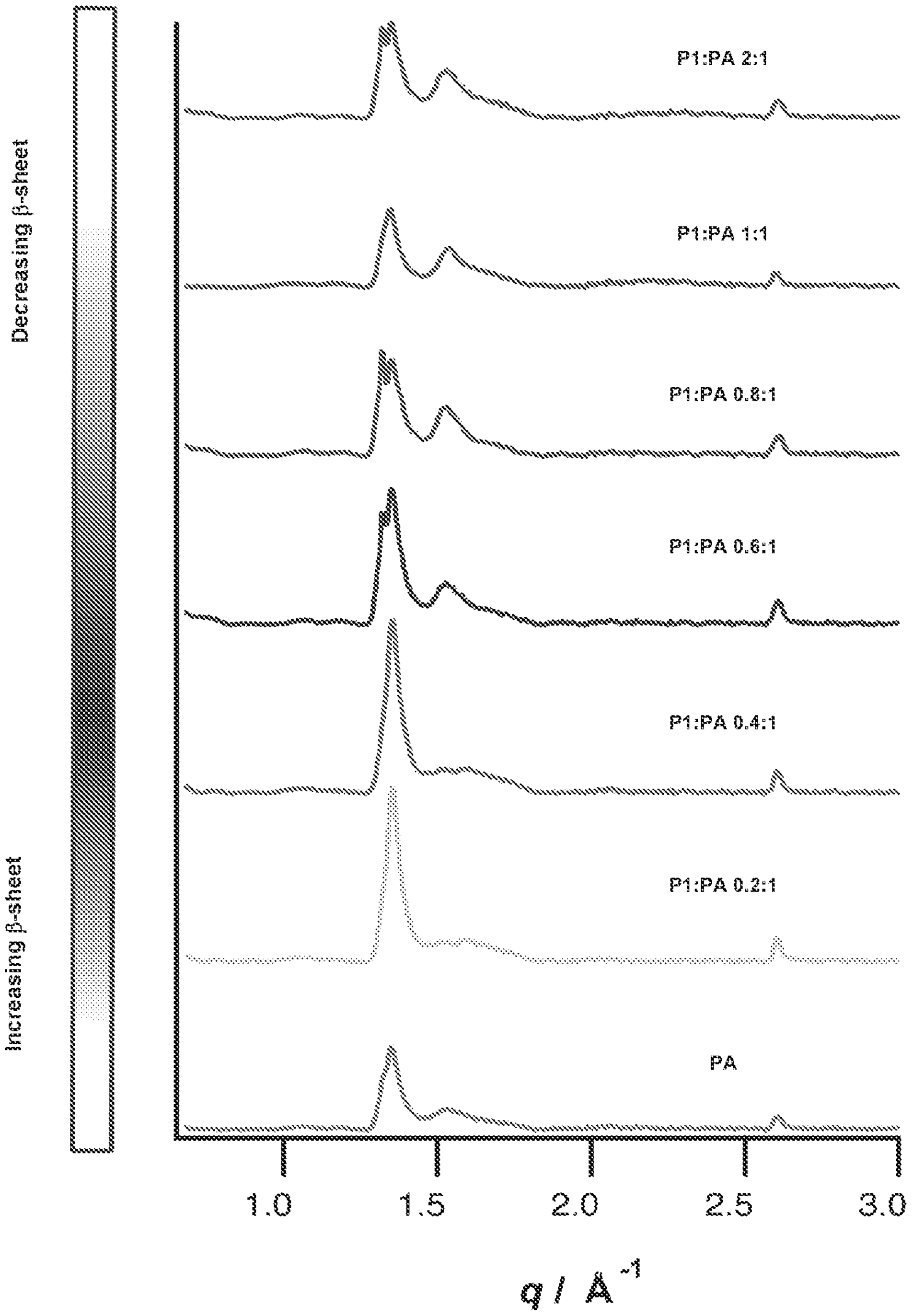
FIG. 5. WAXS patterns of self-assembled PA and P1/PA co-assemblies at molar ratio ranging from 0.2:1 to 2:1.
Figure 6:
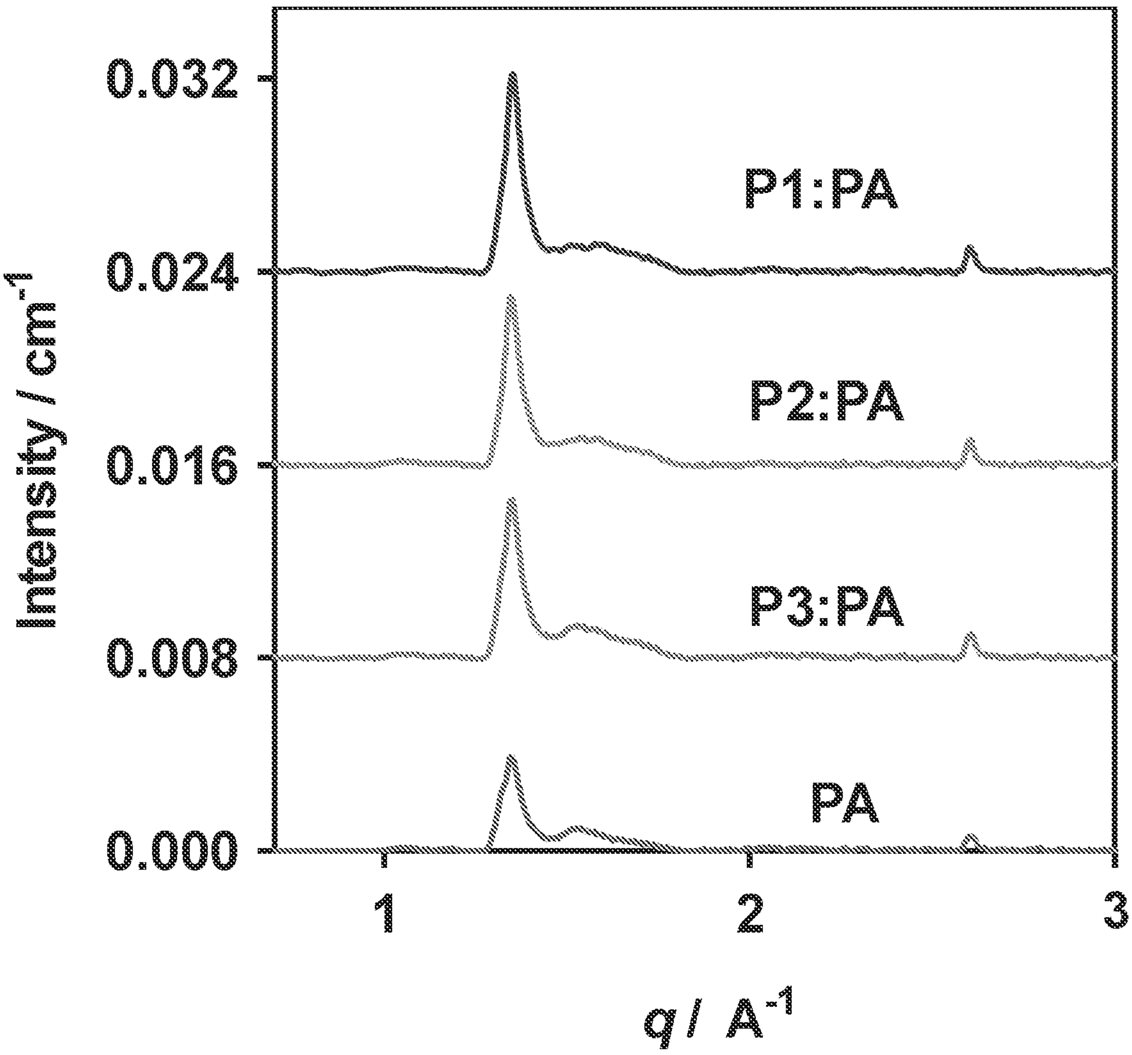
FIG. 6. Comparison of WAXS patterns for self-assembled PA and P1-P3 peptide PA co-assemblies at molar ratio of 0.4:1. PA concentration is 10 mM in all samples for WAXS measurements. The baselines of peptide/PA co-assemblies were offset by 0.008 cm-1 for each pattern.

Solution wide-angle X-ray scattering (WAXS) was used to quantify the degree of long-range order arising from β-sheet motifs within the nanostructures.[2, 6, 7] WAXS patterns of the peptide alone, self-assembled PA and peptide/PA assemblies for P1-P3 were obtained (FIG. 4D-4F). It has been shown that the integrated WAXS peak intensity of proteins is linearly correlated with the number of scatterers.[8] Therefore, this model was adapted to quantify the β-sheet content using the integrated intensity of the Bragg peak around 1.35 $Å^{-1}$. Peptides P1-P3 did not show any Bragg peaks by WAXS, indicating that the short peptides did not have any long-range order under the conditions tested. WAXS was also collected for P1/PA assemblies with free peptide/PA molar ratios from 0.2:1 to 2:1 (FIG. 5). A small equivalent of added P1 increased the β-sheet content relative to PA alone, while further addition of P1 reduced the β-sheet content. Among the tested molar ratios, 0.4:1 P1/PA exhibited the highest β-sheet content. Notably, as free peptide content increased above 0.4:1, a dramatic increase in the intensity of a peak at 1.32 $Å^{-1}$ in addition to the major peak at 1.35 $Å^{-1}$ was observed, indicating that free peptide incorporation amplifies a second β-sheet-like packing motif. The WAXS patterns of PA co-assembled with the other peptides P2 and P3 displayed a similar trend, with higher β-sheet content at a 0.4:1 peptide/PA ratio and a lower β-sheet content at 2:1. However, the increase in the β-sheet content induced by P2 or P3 addition was not as pronounced as P1 based on the observation at representative low peptide molar ratio 0.4:1 (FIG. 6), highlighting the role of hydrophobic amino acid residues in establishing intermolecular forces in free peptide/PA co-assemblies.

Figure 4I:
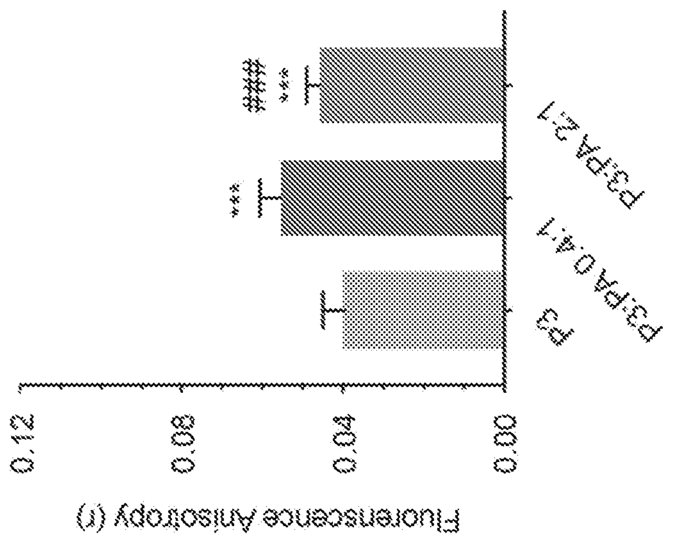
(FIGS. 4G, 4H, and 4I) Fluorescence anisotropy of TAMRA conjugated peptides P1-P3 in non-annealed peptide/PA co-assemblies and peptide alone, showing peptide immobilization in co-assemblies, where the peptide less dynamic in low peptide content than high peptide content. One-way ANOVA with the Bonferroni test is used: ***p<0.001 vs. peptide alone, ###p<0.001 vs. peptide/PA 0.4:1.
Figure 4H:
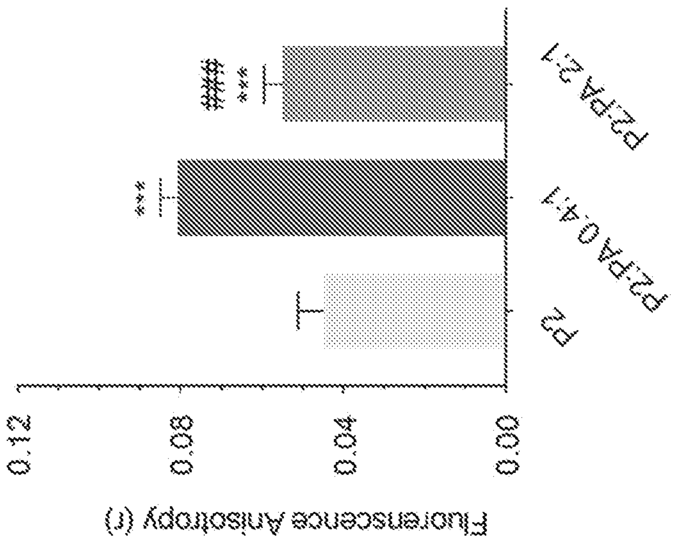
Figure 4G:
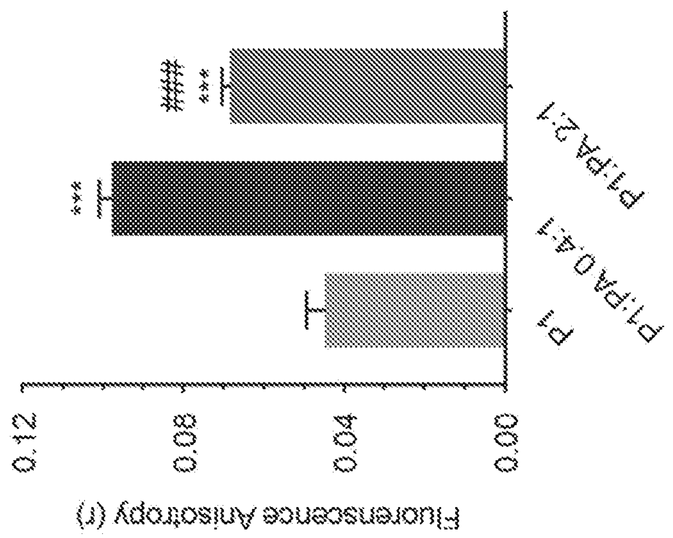

The WAXS patterns revealed that the internal β-sheet of free peptide/PA co-assemblies could be stabilized at low free peptide concentrations or disrupted at high free peptide concentrations. The mobility of these peptides within the co-assemblies was further explored by a fluorescence anisotropy assay,[9, 10] in which the peptide molecular motion was detected by fluorescently labeling 0.5 mol % of the peptide molecules with 5-carboxytetramethylrhodamine (TAMRA). As shown in FIG. 4G-4I, all the peptides alone had low fluorescence anisotropy for these unassembled peptides in a mobile, unstructured state. Compared to P1 alone, P1/PA co-assemblies at 0.4:1 and 2:1 showed significantly higher anisotropy values, indicating that motion of P1 was restricted when co-assembled with PA at both molar ratios. The peptides were more mobile in P1/PA 2:1 than 0.4:1 evidenced by lower anisotropy value, suggesting the weaker intermolecular association within the 2:1 co-assemblies, which showed reduced β-sheet character in WAXS. Similarly, the P2/PA and P3/PA co-assemblies at a 2:1 free peptide/PA molar ratio had increased peptide mobility by fluorescence anisotropy and decreased β-sheet content in WAXS, relative to the 0.4:1 co-assemblies. These observations suggest a correlation between the free peptide dynamics and β-sheet ordering within these co-assembled structures. In view of this data, it is thought that the molecular dynamics of these free peptides are tuned by intermolecular interactions with PA, which includes hydrophobic contacts with adjacent PA through the amino acid side chains and β-sheet hydrogen bonding.

Figure 7A:
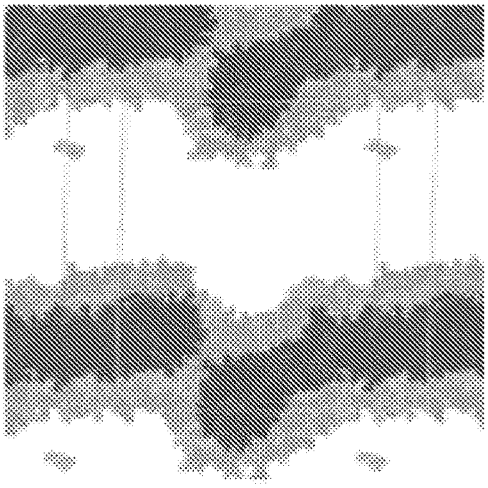
FIG. 7. Co-assembly mechanism analysis of free peptide/PA co-assembly. Molecular dynamics simulations showing the arrangement of P1/PA co-assembled nanoribbons at low free peptide content (FIG. 7A) and at high free peptide content (FIG. 7B). The alkyl tail (in dark blue) stacking is influenced by the amount of incorporated free peptide (in light blue). Cryo-TEM of P1 co-assembled PA at molar ratios of 0.4:1 (FIG. 7C) and 2:1 (FIG. 7D). Scale bar is 100 nm. e, Plot showing size of clusters PA alkyl tails (black) and P1 (blue) with intermolecular spacing less than 0.6 nm.
(FIG. 7F) Plots of the radial molecular distribution in the P1/PA co-assemblies, showing PA arrangement (solid line) at increasing free peptide content (dashed line).
(FIG. 7G) Plot of the PA hydration as a function of increasing equivalents of added free peptide.
(FIG. 7H) Transmission Fourier-transform infrared (FTIR) spectra of P1/$^{13}$C-PA co-assemblies and $^{13}$C-PA ($^{13}$C-PA: $C_{15}H_{31}$CO-VV*VAAAEEE-$NH_2$).
Figure 7B:
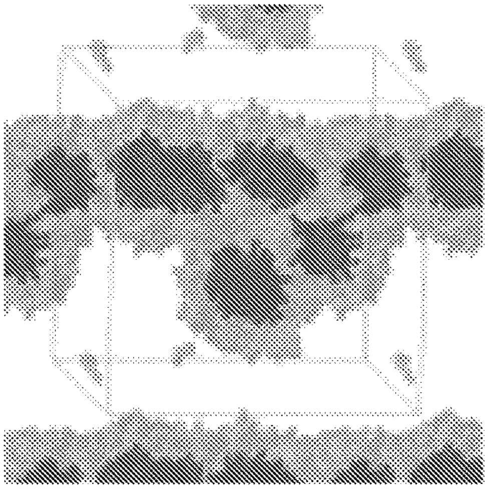
Figure 7C:
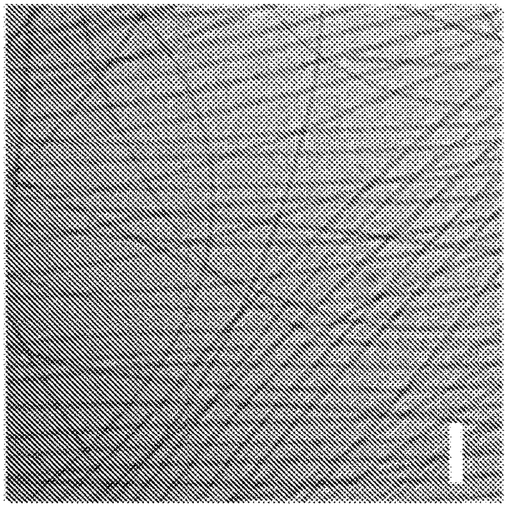
Figure 7D:
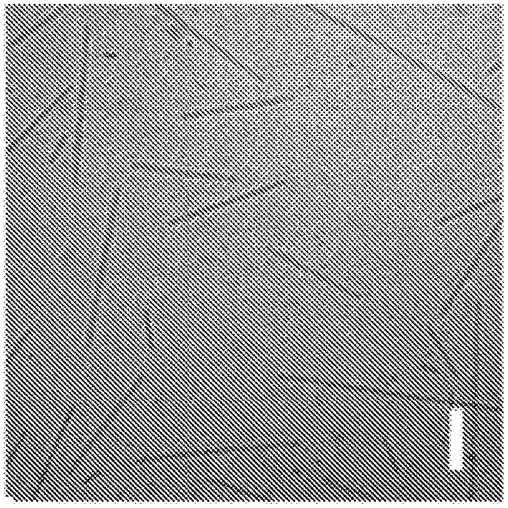
Figure 8:
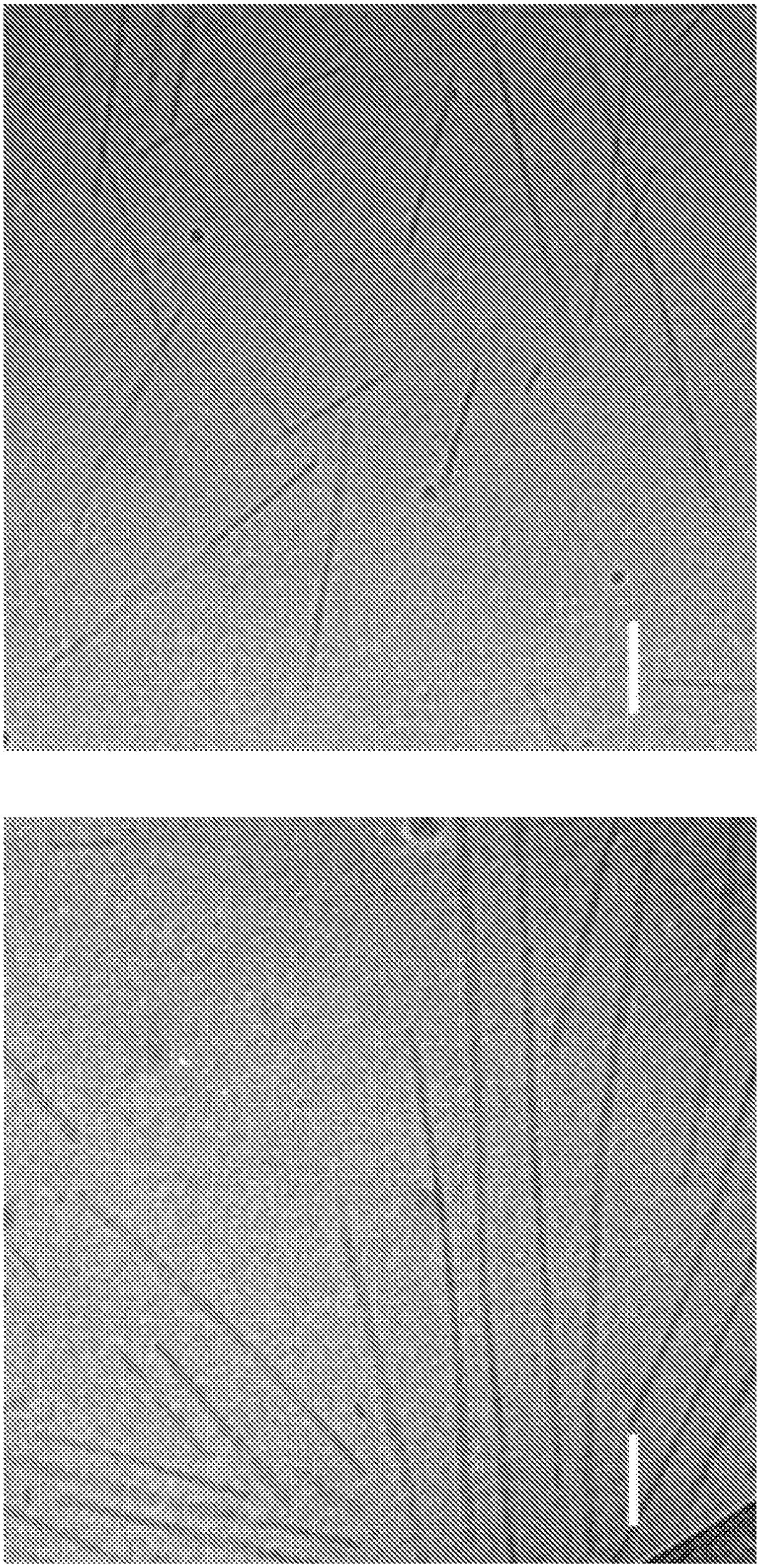
FIG. 8. Cryo-TEM images of aged P2/PA and P3/PA co-assemblies at molar ratio of 2:1.
Figure 9:
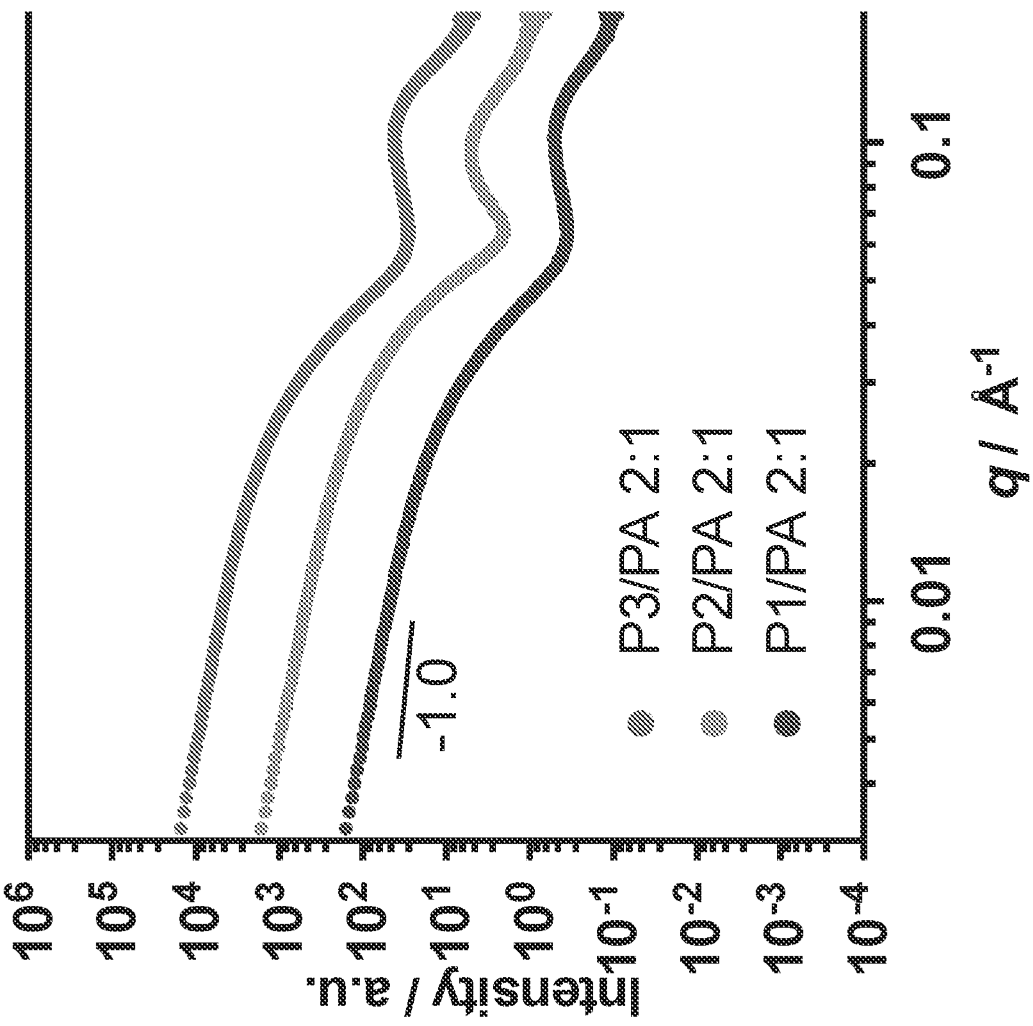
FIG. 9. SAXS profiles of P1-P3 peptide/PA co-assemblies at molar ratio of 2:1. PA concentration is 10 mM in all samples for SAXS measurements.

To investigate the molecular mechanisms of free peptide and PA co-assembly at low and high free peptide concentrations, the molecular alignment within the co-assembled nanostructures of P1/PA was probed using a combination of coarse-grained molecular dynamics simulations and additional spectroscopic experiments (FIG. 7). Analogous to the experimental condition in which the free peptide/PA mixtures were dried from HFIP and then dissolved in water, simulations were performed in which P1 was randomly mixed with PA molecules at varying peptide/PA molar ratios ensuring that aggregation of peptide and PA would happen simultaneously from the monomeric state once they are solvated in water. As shown in FIG. 7A, low free peptide addition of P1 (P1/PA 0.4:1) did not impact the nanofiber hydrophobic core of stacked PA alkyl tails; however, the nanofiber core began breaking up with further P1 addition (FIG. 7B), suggesting that PA β-sheet domain was disrupted by the excess free peptide. This internal structure disruption resulted in nanostructure morphological changes observed by cryo-TEM. The co-assemblies at high free peptide content (2:1, FIG. 7D) were short nanoribbons, in contrast to long nanoribbons formed by low free peptide content co-assemblies (0.4:1, FIG. 7C). For the other two peptides P2 and P3, the 2:1 peptide/PA co-assemblies also displayed short nanoribbons by cryo-TEM (FIG. 8). Solution SAXS profiles of P1-P3 co-assemblies with PA at 2:1 (FIG. 9) showed −1 slope in Guinier region, supporting the 1D structures observed on cryo-TEM.

Figure 7E:
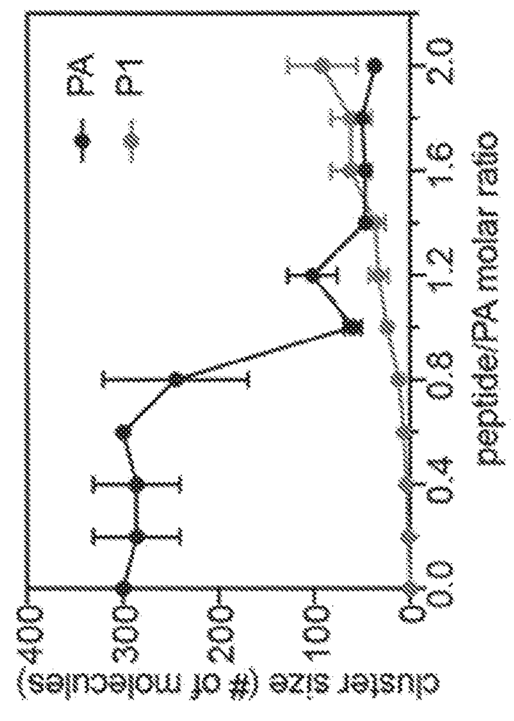
Figure 7F:
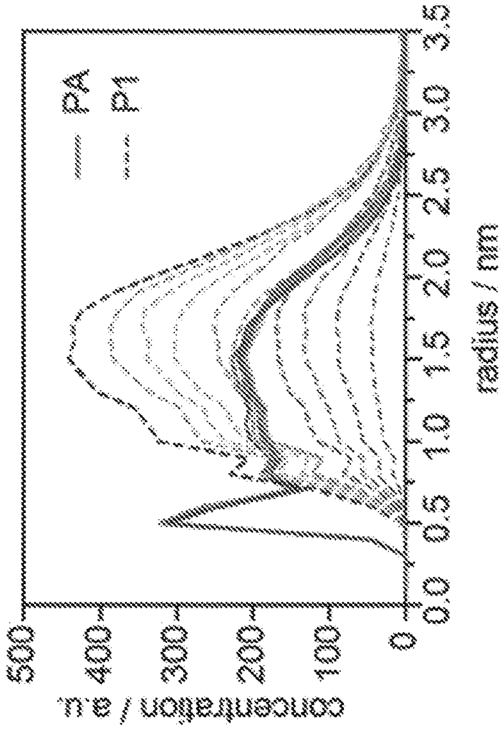
Figure 7G:
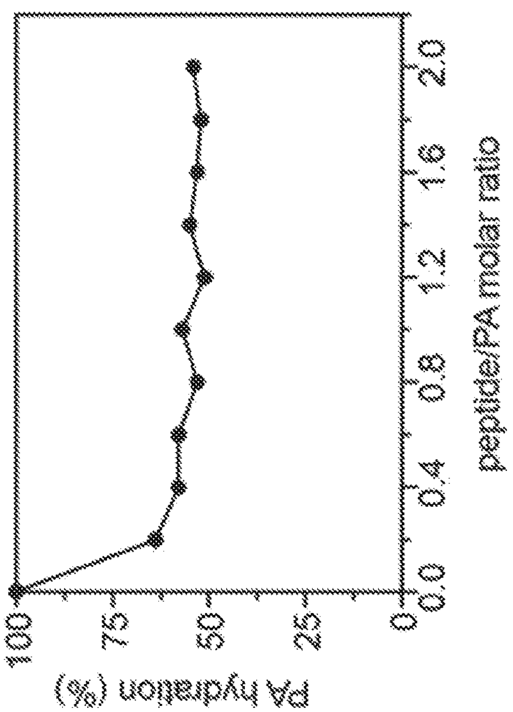

As shown in FIG. 7E, the simulation results were quantitatively described using cluster analysis in order to elucidate the molecular distribution of free peptides and PAs within the co-assemblies as a function of free peptide content. In this analysis, clusters of PA aliphatic tails or peptides with less than 0.6 nm intermolecular spacing were defined. At low P1/PA ratios, all 300 PA molecules in the simulation box exist as a single cluster. With increasing P1/PA ratio above 0.4:1, the averaged PA cluster size gets much smaller with an average of approximately 30 molecules per cluster at high P1/PA ratios. Conversely, the peptide cluster size of P1 increased monotonically with the peptide concentration. This trend suggests that the peptides are distributed separately at lower molar ratios and only clustered at high peptide concentration. The radial distribution of P1 (dashed line) and PA (solid line) from the core to surface is shown in FIG. 1F. The PA radial distribution does not change with increasing ratios of P1, indicating the free peptide has little impact on the cross-sectional arrangement of PA molecules. At low free peptide concentrations (0.2-1.2 equiv. P1), P1 is superimposable with the whole peptide region (0.8-2.7 nm) of PA. Above 1.2 equiv., where the free peptide is in excess, the free peptide accumulates in the region close to the fiber edge (at a radius of 1.5-2.0 nm). The accumulation of free peptide towards the edge of the fiber, increases the fiber radius from 2.1 to 2.5 nm. Therefore, P1 is not well internalized at high concentrations and instead localizes near the fiber surface causing the fibers to expand.

Figure 7H:
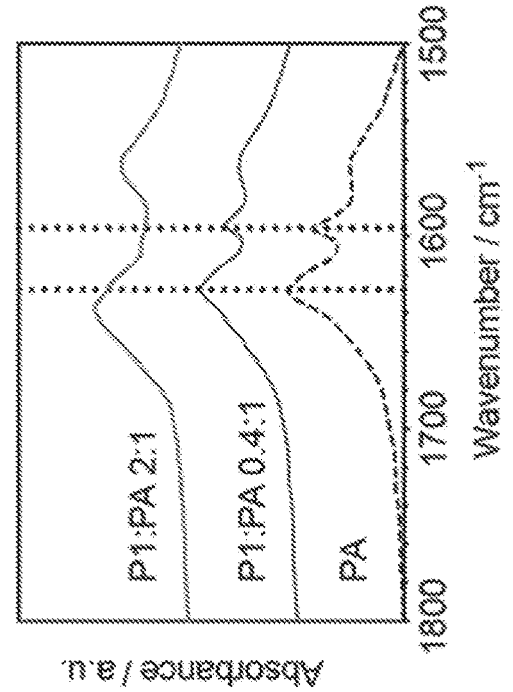
Figure 10:
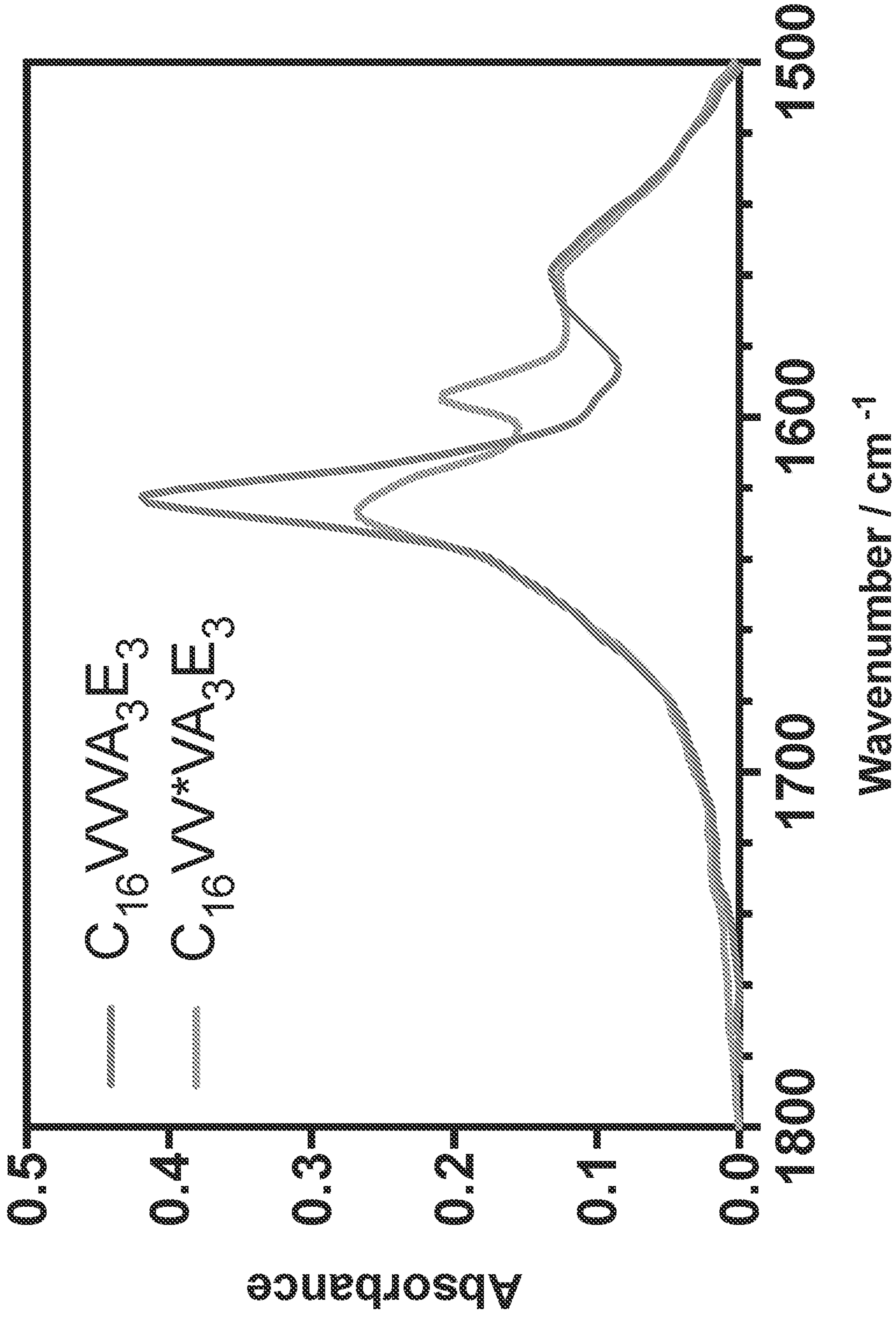
FIG. 10. Transmission FT-IR spectra of PA ($C_{16}$-$V_3A_3E_3$ (SEQ ID NO: 47)) and $^{13}$C-PA ($C_{16}$VV*$VA_3E_3$ (SEQ ID NO: 47)).
Figure 11:
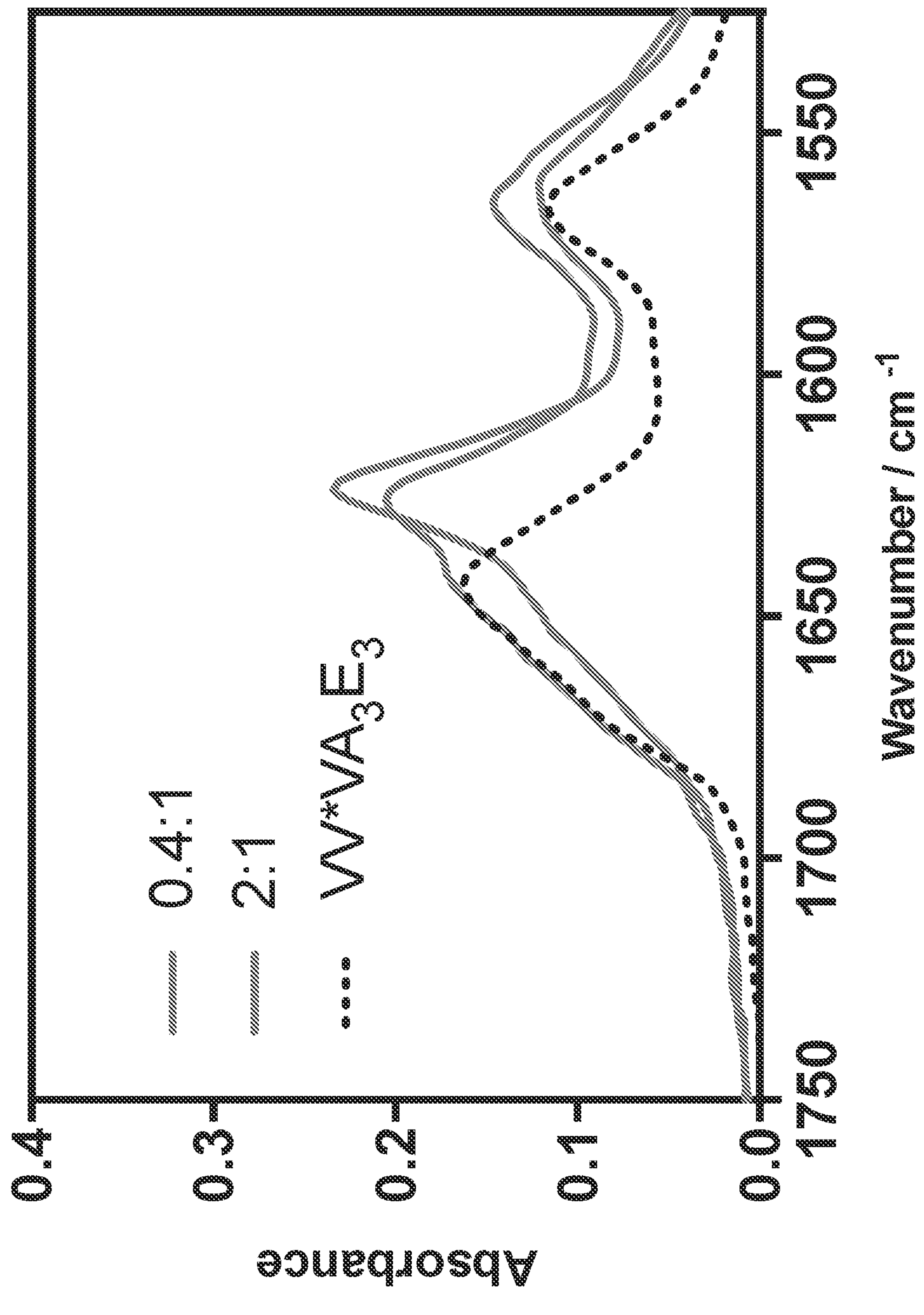
FIG. 11. Transmission FT-IR spectra of non-annealed P1/PA co-assembly at molar ratios of 0.4:1 and 2:1, and P1 only, where P1 is 100% $^{13}$C-labeled on the carbonyl of middle valine (VV*$VA_3E_3$ (SEQ ID NO: 47)).

The co-assembly mechanism at the molecular level was characterized by transmission Fourier transform infrared (FTIR) spectroscopy (FIG. 7H). The PA molecule was isotopically labeled with $^{13}C$ at the carbonyl group of the middle valine ($C_{15}H_{31}$CO-VV*VAAAEEE (SEQ ID NO: 47)-$NH_2$) to provide a spectroscopic handle that does not perturb the overall assembly. Compared to the FTIR spectrum of non-labeled PA, the $^{13}C$-PA showed a shifted peak at 1593 $cm^{-1}$ arising from the β-sheet motif formed by the isotope-labeled valines (FIG. 10). In the 2:1 P1/PA co-assemblies, the disappearance of the 1593 $cm^{-1}$ peak suggested the decoupling of the hydrogen bonding between PA amides, which is likely caused by the insertion of P1, whereas in 0.4:1 co-assemblies this peak remains, demonstrating that PA hydrogen bonding was not affected by addition of a small amount of free peptide. When $^{13}C$-P1 (Ac-VV*VAAAEEE (SEQ ID NO: 47)-$NH_2$) was used in P1/PA co-assemblies, no shift in the β-sheet peak was detected for ratios of 0.4:1 or 2:1, which suggests that the co-assembled P1 does not form distinct β-sheet domains within the nanostructure (FIG. 11). The simulations further elucidated the co-assembly mechanism by demonstrating PA hydration as a function of the free peptide/PA ratios (FIG. 7H). The addition of P1 up to 0.4 equiv. causes water exclusion but higher ratios do not cause any further changes in PA hydration. Together with the increased β-sheet signal at low free peptide content and the decreased β-sheet signal at high free peptide content observed in WAXS observed herein, it was speculated that the small amount of free peptide stabilizes the internal structure and elongates the coherence length of the nanostructure by replacing the water between β-sheet motifs. When PA is mixed with high concentrations of free peptide, the free peptide tends to suppress β-sheet formation by inhibiting the directional extension of PA hydrogen bonding in the nanostructure.

Figure 12A:
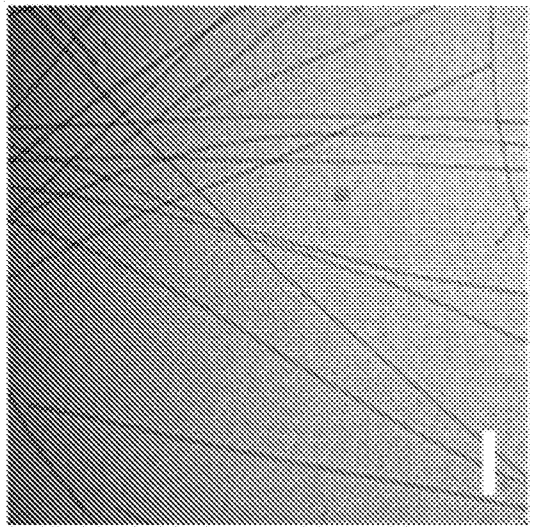
FIG. 12. Effect of annealing on peptide/PA co-assembly. Representative cryo-TEM images of P1/PA assemblies at a molar ratio of 0.4:1 under non-annealed (FIG. 12A) and annealed conditions (FIG. 12B).
(FIG. 12C) SAXS profiles of annealed and non-annealed 0.4:1 P1/PA co-assemblies showing shifted minimum.
(FIG. 12D) VT-WAXS profiles of P1/PA co-assemblies at 0.4:1 P1/PA with heating from 35° C. to 85° C. and subsequent cooling.
(FIG. 12E) Plot of the fluorescence anisotropy of TAMRA-P1 in non-annealed and annealed P1/PA assemblies. One-way ANOVA with the Bonferroni test is used: *p<0.001.
(FIG. 12G) Schematic representation of free peptide (in red) and PA (in gray) co-assembly products at different conditions.
Figure 12B:
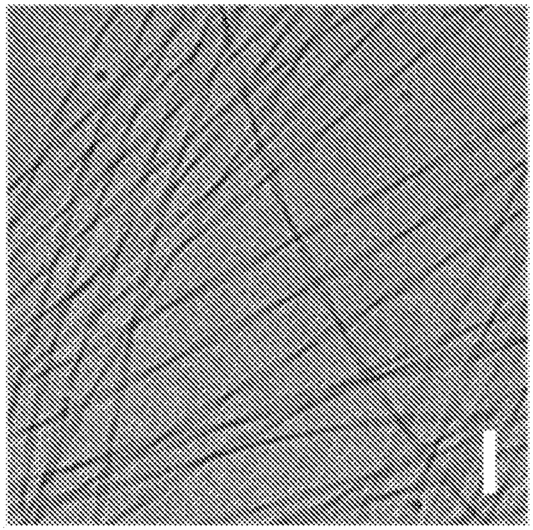
Figure 12C:
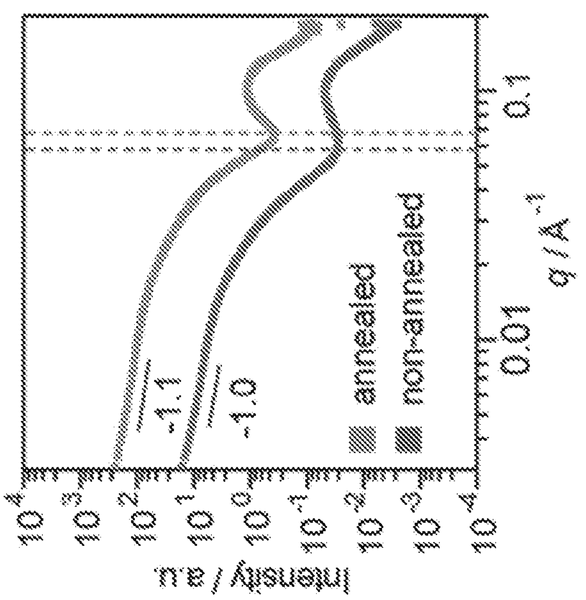
Figure 12D:
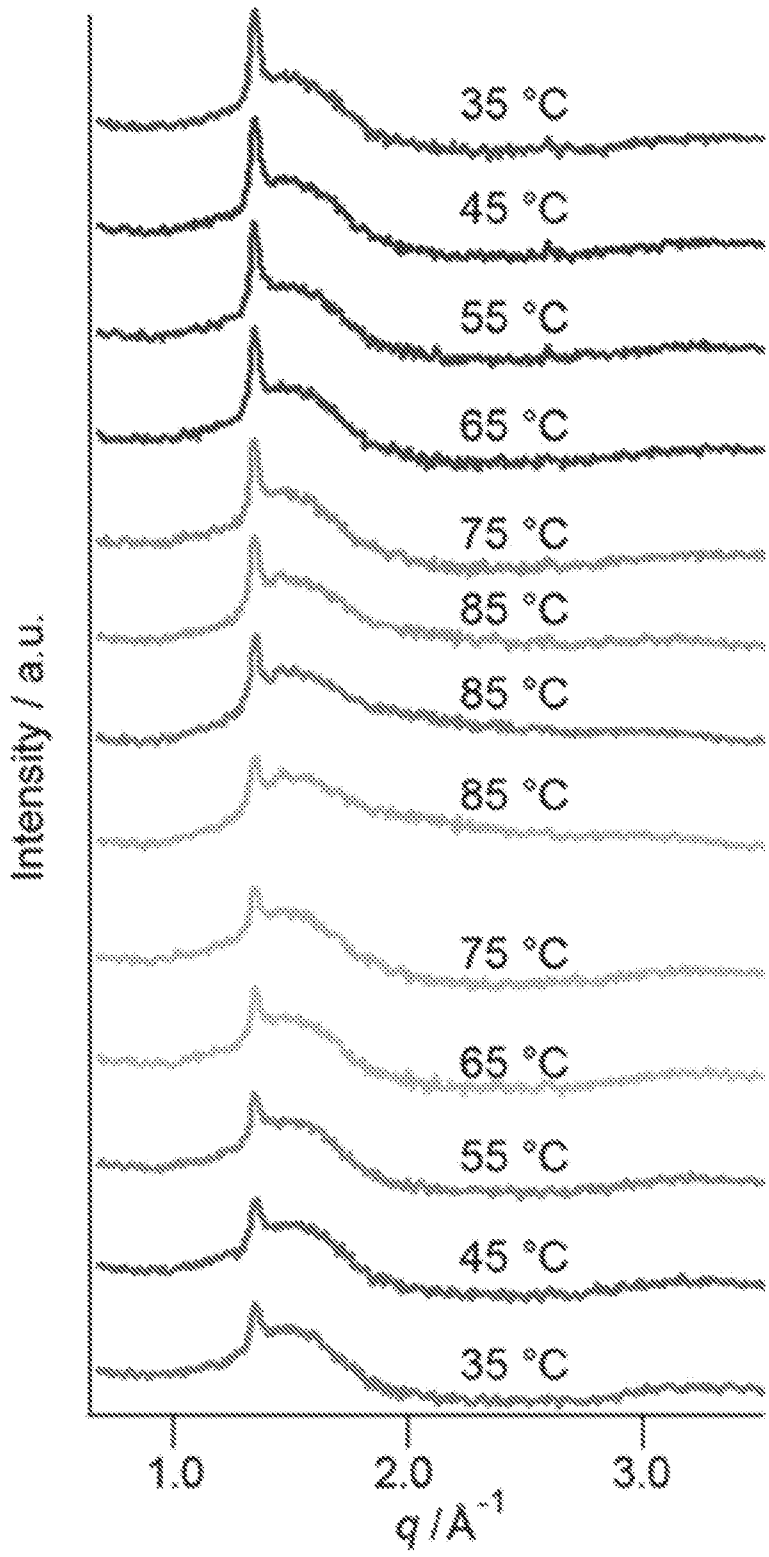
Figure 12E:
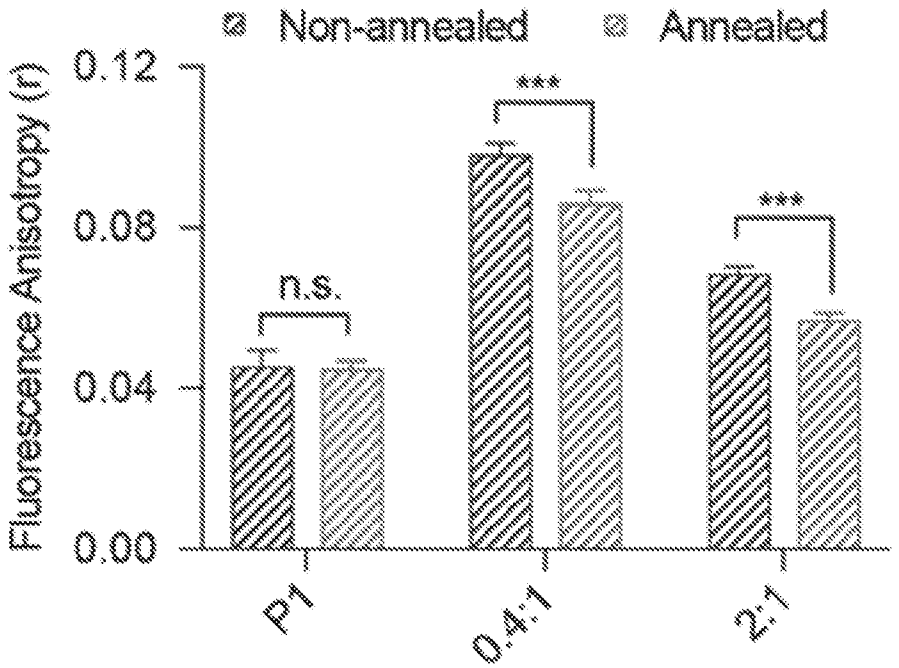
Figure 14A:
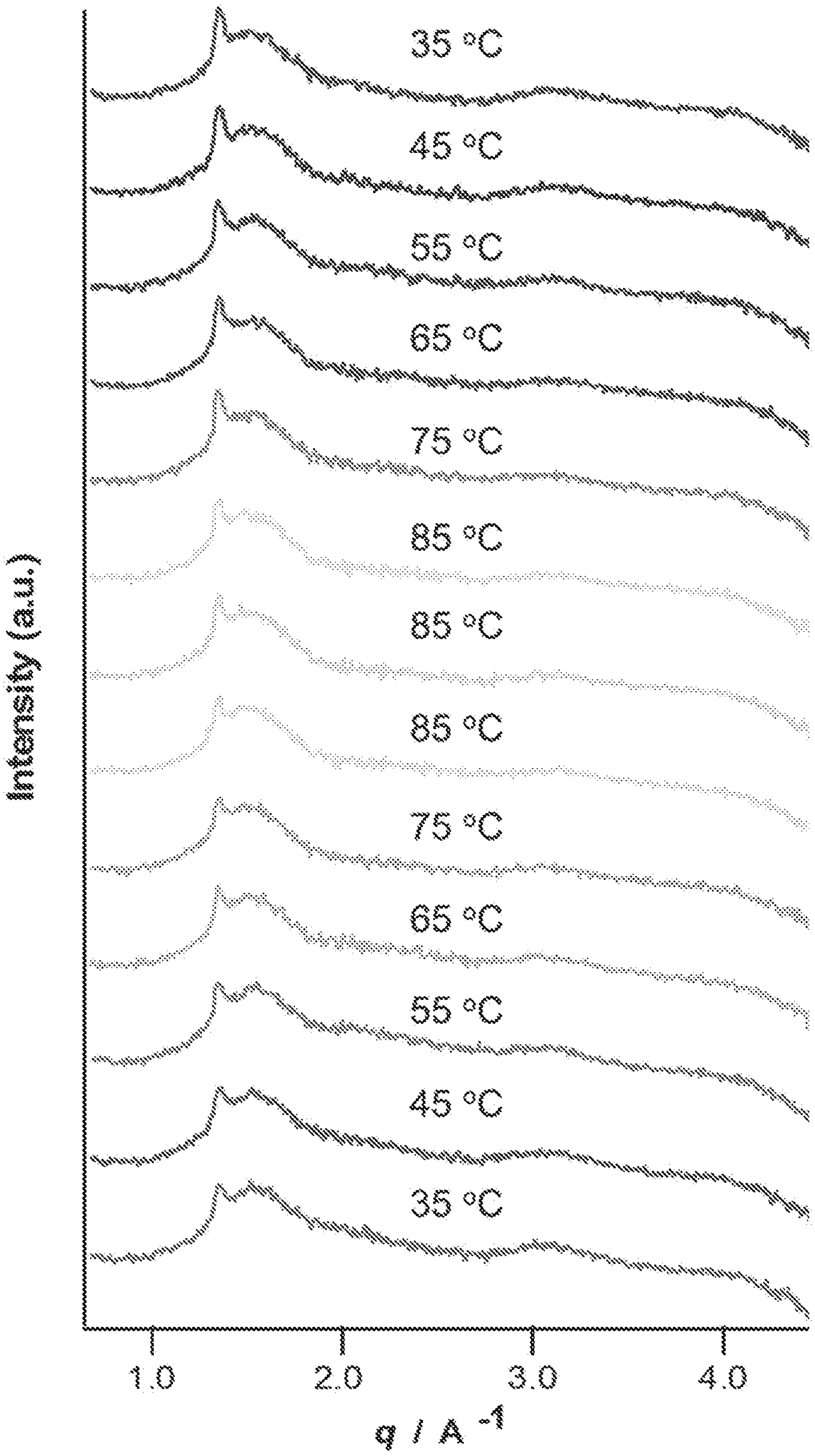
FIG. 14. Variable temperature-WAXS of co-assembled P1/PA at molar ratio of 2:1 (FIG. 14A) and self-assembled PA alone (FIG. 14B). Heating and cooling process are shown from bottom to top.
Figure 14B:
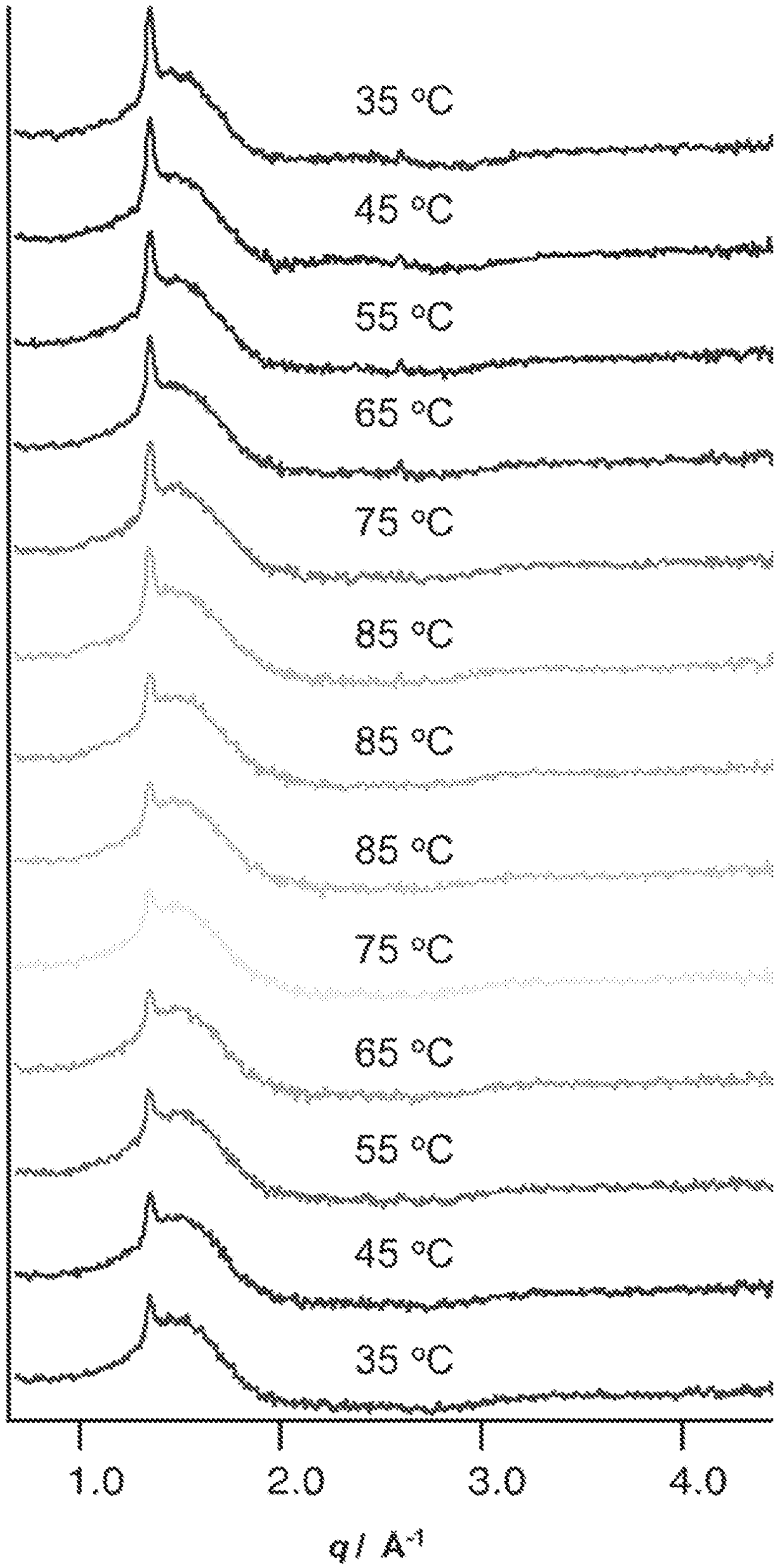

Previous studies have shown that thermal energy can drive supramolecular PA assemblies into long, thermodynamically favored nanostructures.[1] Beyond the non-annealed peptide/PA co-assemblies, it is of great interest to investigate thermodynamic products of these co-assemblies that might extend the scope of available structures and functions. Cryo-TEM showed that the co-assembled P1/PA 0.4:1 nanostructures transitioned from cylindrical fibers (FIG. 12A) into twisted 1D ribbons (FIG. 12B), which is supported by the SAXS profiles (FIG. 12C) where the slope of annealed samples is more negative (−1.1) compared to the non-annealed samples (−1.0). Furthermore, after annealing the SAXS minimum becomes sharper, which indicates increased contrast of the annealed nanoribbons relative to the solvent, likely due to water exclusion from the nanostructure after thermal annealing. The transformation into wider ribbons and SAXS minimum sharpening were also observed in P1/PA 2:1 and PA alone at annealed state (FIG. 13). Variable-temperature WAXS (VT-WAXS) was employed to monitor the internal structural changes of free peptide/PA co-assemblies during the annealing process, demonstrated by P1/PA 0.4:1 (FIG. 12D). The intensity of the β-sheet peak slightly decreases as the temperature increases. During the process of annealing at 85° C. followed by cooling down, the β-sheet peak at 1.35 $Å^{-1}$ becomes more intense and narrower, suggesting that the β-sheet motif becomes more ordered. The annealing process of 2:1 P1/PA and PA alone was also characterized by VT-WAXS, which showed a similar increase in the intensity of the β-sheet peaks (FIG. 14). Moreover, the decrease in the fluorescence anisotropy of P1 in the P1/PA co-assemblies after annealing suggests increased peptide mobility in both 0.4:1 and 2:1 molar ratios, likely due to reduced affinity between P1 and PA (FIG. 12E).

Figure 12F:
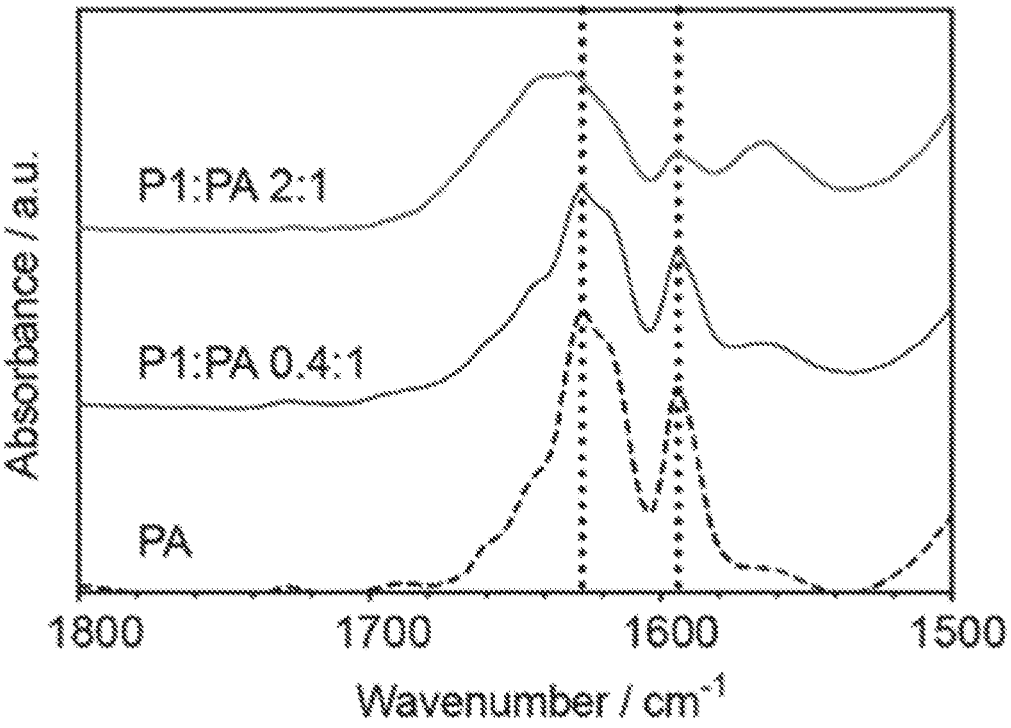
Figure 12G:
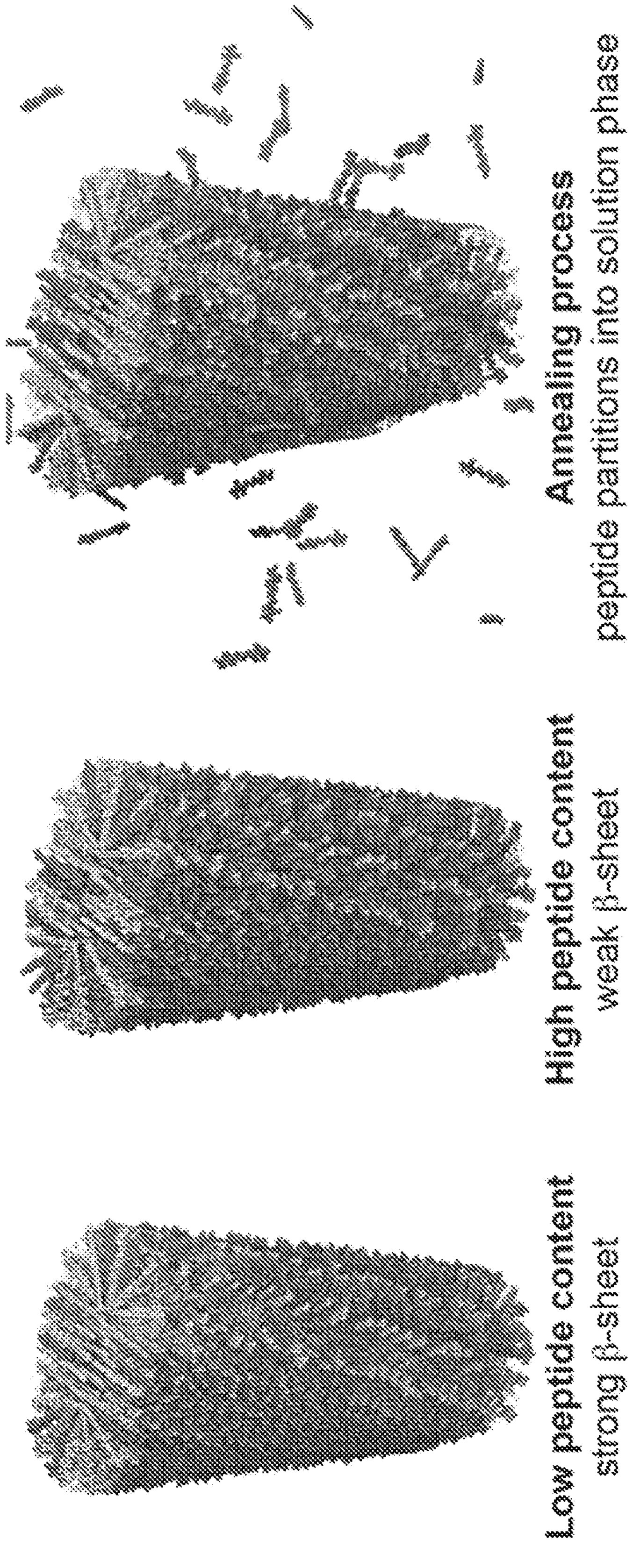
Figure 13B:
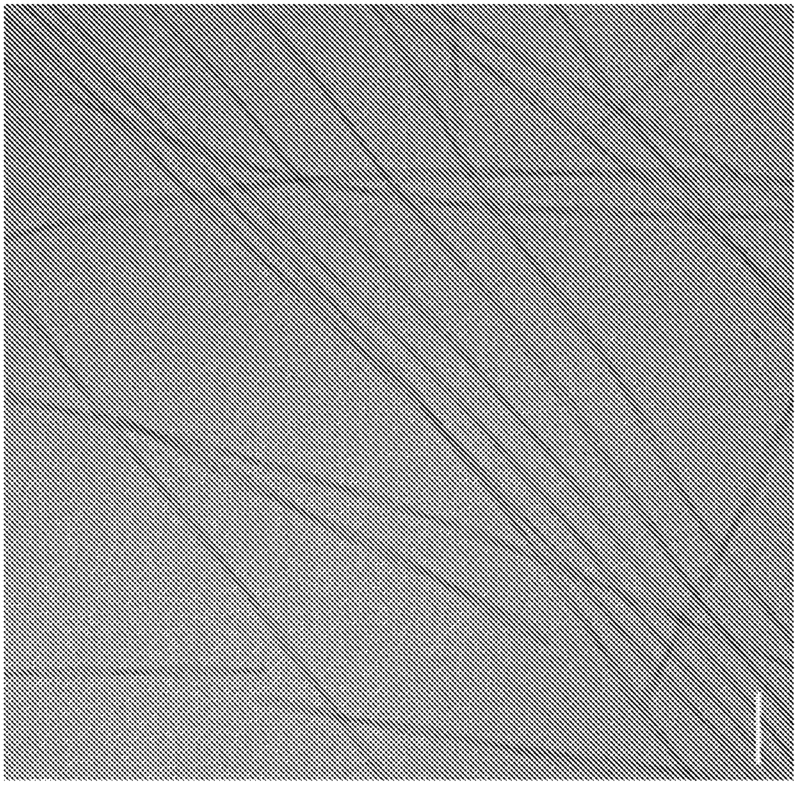
FIG. 13. Cryo-TEM images 2:1 P1/PA assemblies at under non-annealed (FIG. 13A) and annealed condition (FIG. 13B) and self-assembled PA under non-annealed (FIG. 13D) and annealed condition (FIG. 13E), scale bar is 100 nm. Small-angle X-ray scattering (SAXS) profiles of annealed and non-annealed 2:1 P1/PA co-assemblies (FIG. 13C) and self-assembled PA (FIG. 13F) in water.
Figure 13A:
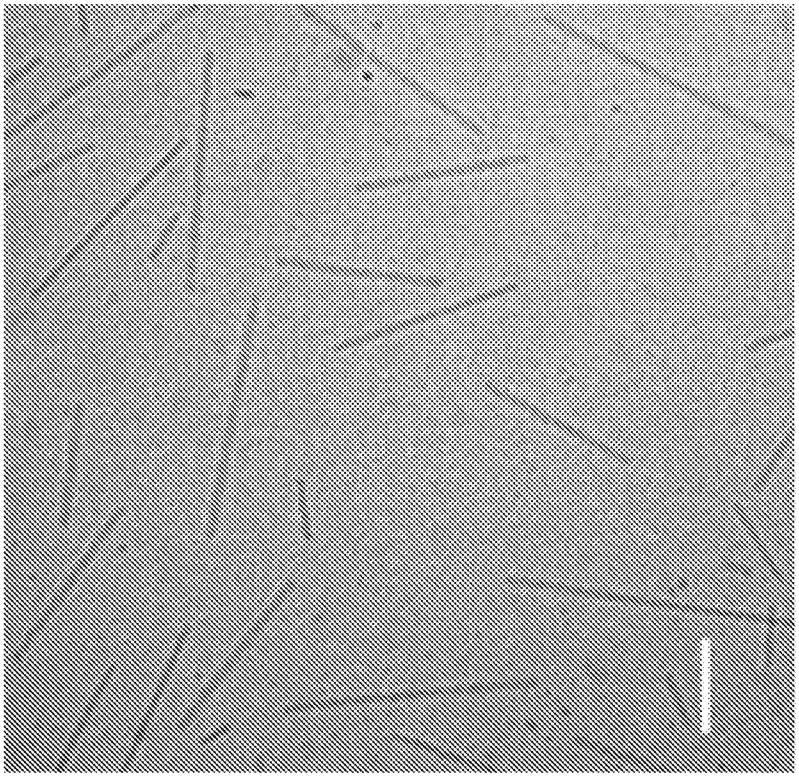
Figure 13C:
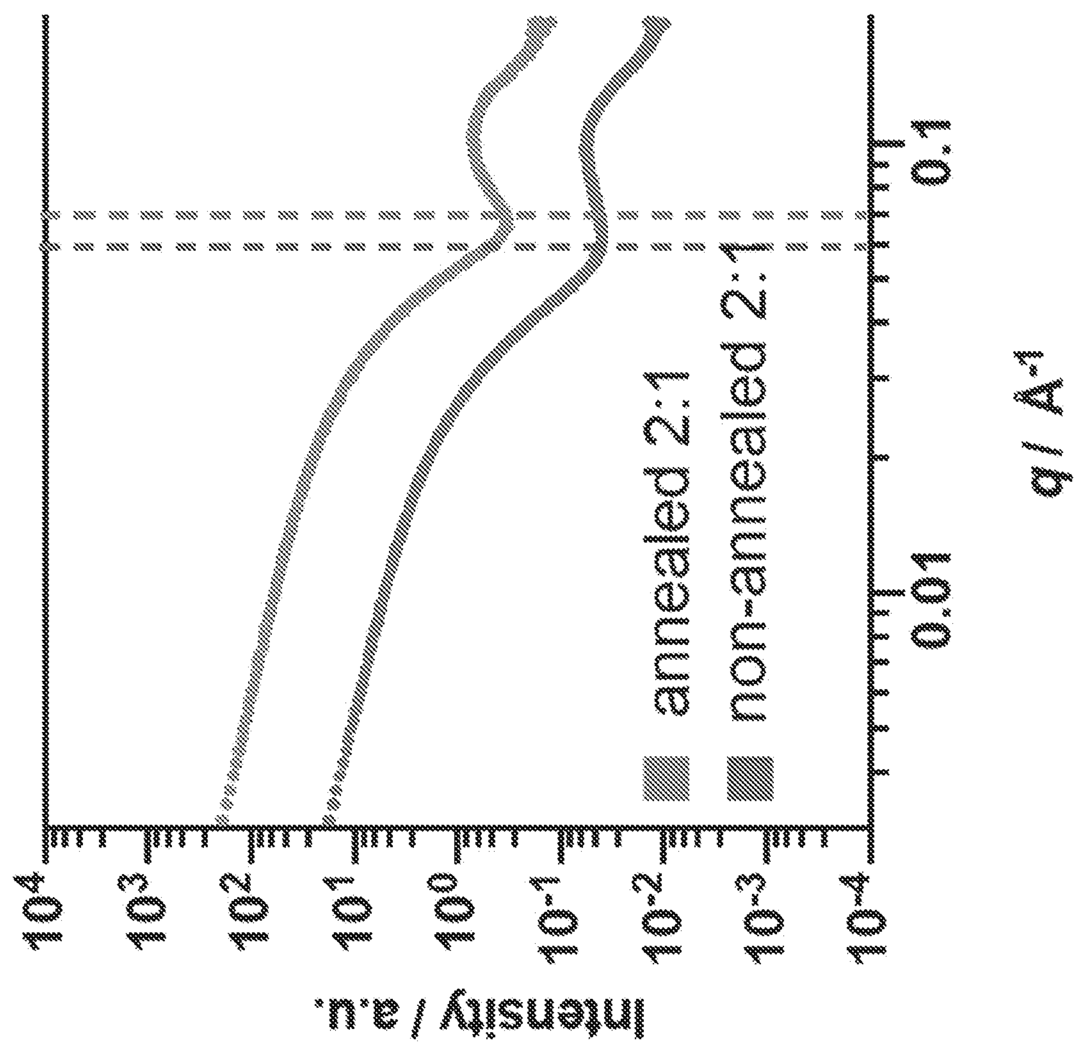
Figure 13E:
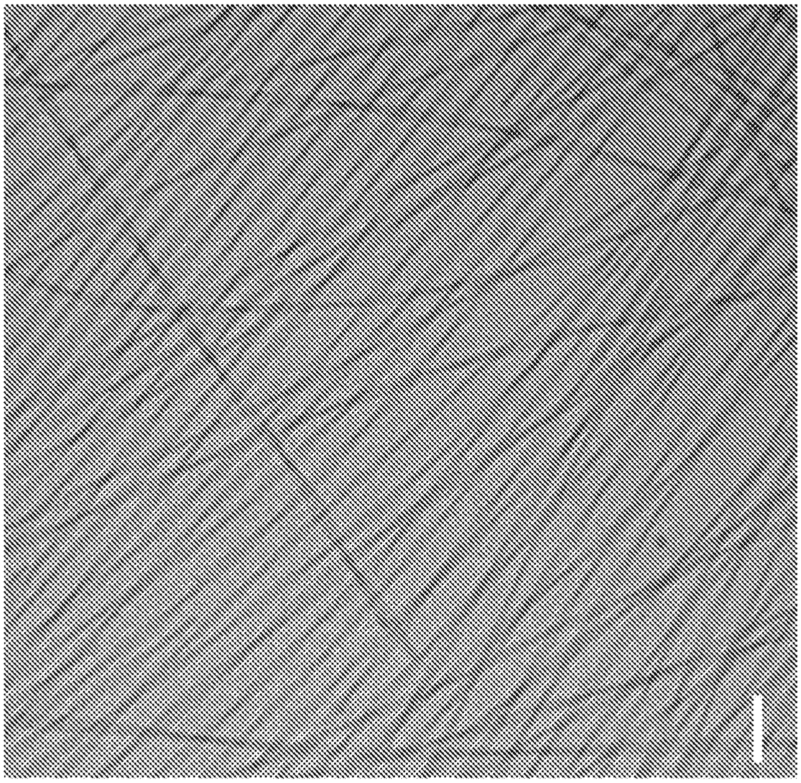
Figure 13D:
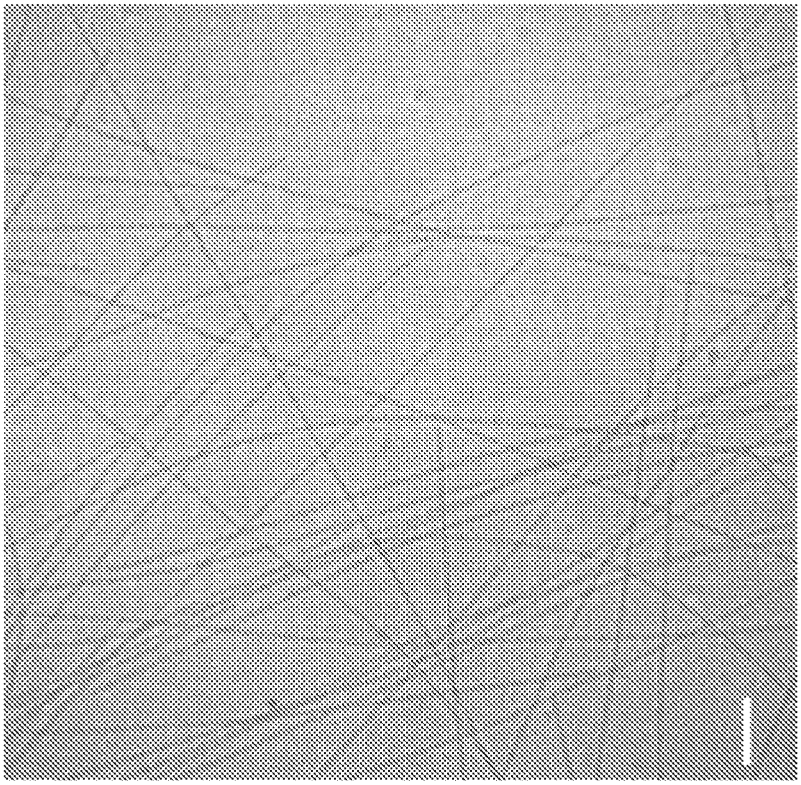
Figure 13F:
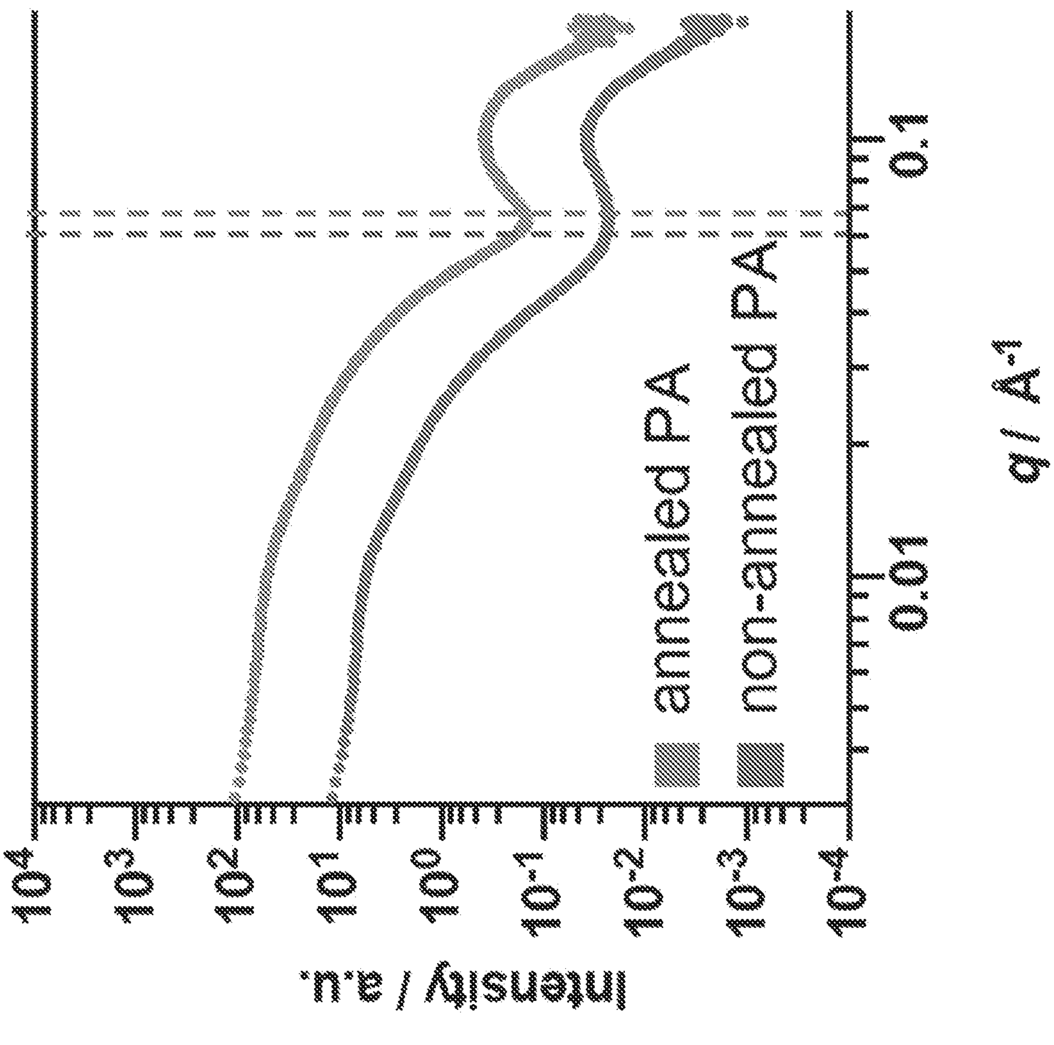
Figure 15:
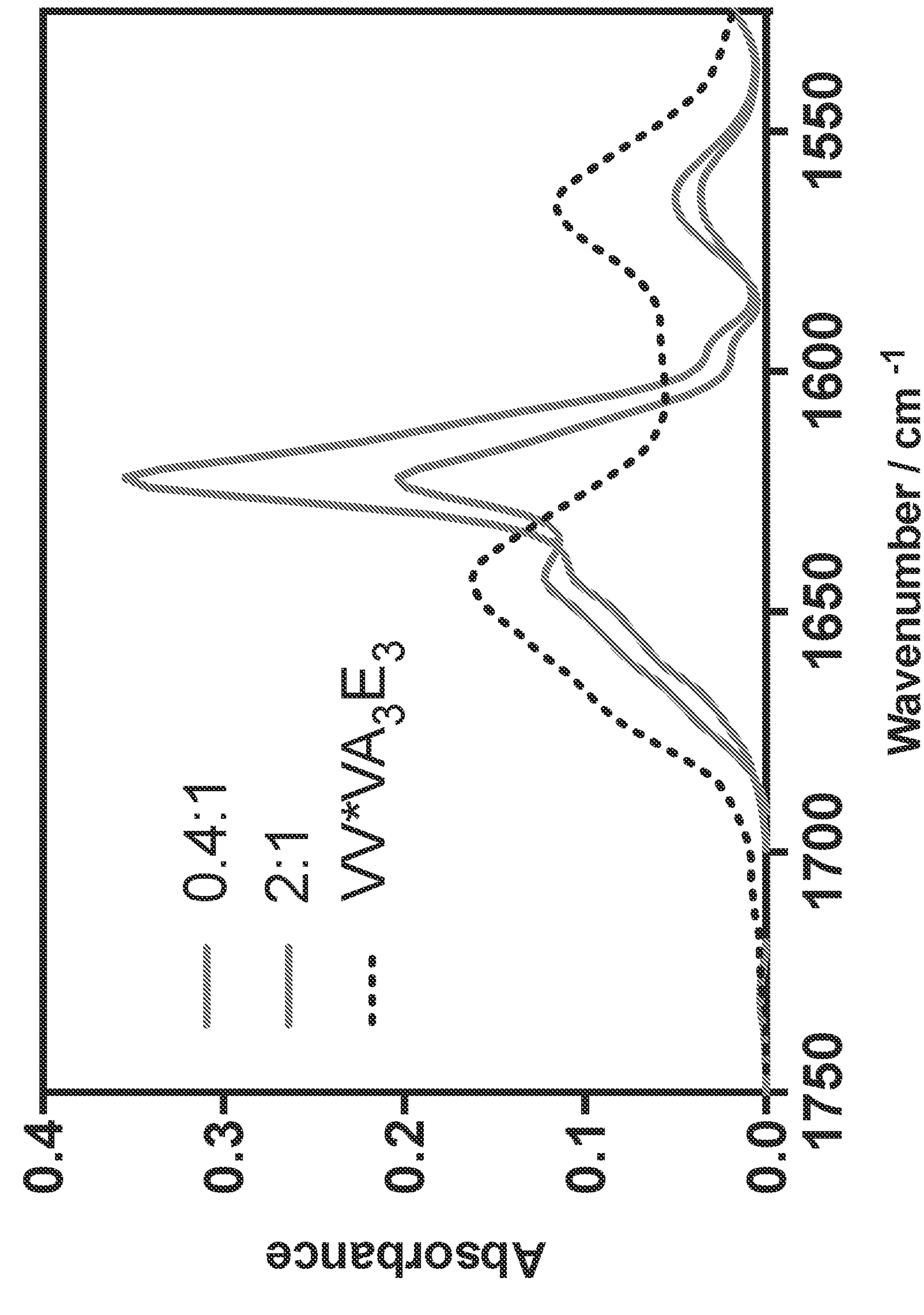
FIG. 15. Transmission FT-IR spectra of annealed P1/PA co-assembly at molar ratios of 0.4:1 and 2:1, and P1 only, where all the P1 is $^{13}$C-labeled on the carbonyl of middle valine.

In addition to VT-WAXS and fluorescence anisotropy, FTIR with the $^{13}$C-labeled PA revealed intermolecular association in the annealed structure (FIG. 12F). The presence of the peak at 1593 cm' in the 2:1 co-assembly suggests PA restored the hydrogen bonding with itself by expelling the free peptide upon thermal annealing. When the $^{13}$C-P1 (Ac-VV*VAAAEEE (SEQ ID NO: 47)-$NH_2$) was added to annealed P1/PA co-assemblies, no β-sheet peak was observed from the labeled valine in 0.4:1 or 2:1 ratios, indicating that P1 did not form any β-sheet structures on its own after annealing (FIG. 15). As shown in FIG. 12G, the free peptide is located between the β-sheets at the low ratio and intercalates into hydrogen bonds of the PA β-sheets at the high ratio. However, the incorporation of the free peptide within the hydrogen bonded β-sheets is not thermodynamically favored, since annealing expels the free peptide from the PA nanostructure.

Amyloid β (Aβ) is the major proteinaceous constituent of senile plaques, which are the pathological hallmark of Alzheimer's disease (AD).[11] The Aβ oligomers, with intermediate structure between monomers and fibrils, have been identified as the toxic species in a number of different neurodegenerative disorders.[12]

The pentapeptide P4 (Ac-LPFFD (SEQ ID NO: 45)-$NH_2$) is a pentapeptide with an amphiphilic nature that was designed to disrupt the β-sheet structure formation during amyloid aggregation. Having investigated the co-assembly mechanisms of complementary peptides with PA, it was hypothesized that PA could be utilized as a drug carrier that co-assembles with P4. P4 is another exemplary free peptide described herein.

Figure 16A:
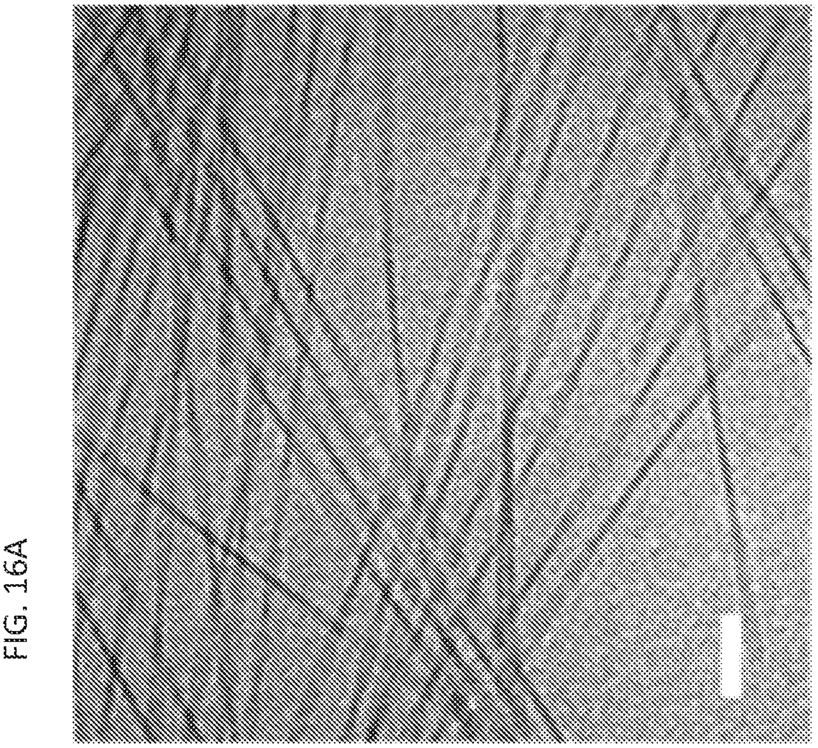
FIG. 16. Enhanced inhibition on Aβ42 aggregation by peptide/PA co-assembly. Cryo-TEM of co-assembly of P4 (Ac-LPFFD (SEQ ID NO: 45) —NH2) with PA at 0.4:1 (FIG. 16A) and 2:1 (FIG. 16B) at non-annealed state.
(FIG. 16C) SAXS profiles of non-annealed PA, P4/PA co-assemblies at molar ratios of 0.4:1 and 2:1.
(FIG. 16D) WAXS profiles of P4 and non-annealed PA, P4/PA at 0.4:1 and 2:1. The baselines of PA and free peptide/PA co-assemblies were offset by 0.008 cm-1 for each pattern. e-g, Internal molecular packing of co-assembled P4 (in light pink) and PA (in dark pink) at low free peptide content (FIG. 16E) and high free peptide content (FIG. 16F), corroborated by cluster analysis of PA alkyl tail and P4 at increasing equivalents (FIG. 16G).
(FIG. 16H) Transmission Fourier-transform infrared (TR-FTIR) spectroscopy of non-annealed P4/13C-PA co-assemblies (13C-PA: $C_{15}H_{31}$CO-VV*VAAAEEE (SEQ ID NO: 47) —NH2).
(FIG. 16I) P4 degradation upon chymotrypsin for 24 hours, showing co-assembling with PA can prevent P4 from enzymatic degradation. The percentage of remaining P4 is based on HPLC peak area.
(FIG. 16J) Aβ42 aggregation kinetics where the ThT fluorescence intensity is positively correlated to Aβ42 β-sheet content as aggregating, showing that the P4/PA co-assemblies are more potent that P4 on inhibiting the Aβ42 aggregation.
Figure 16B:
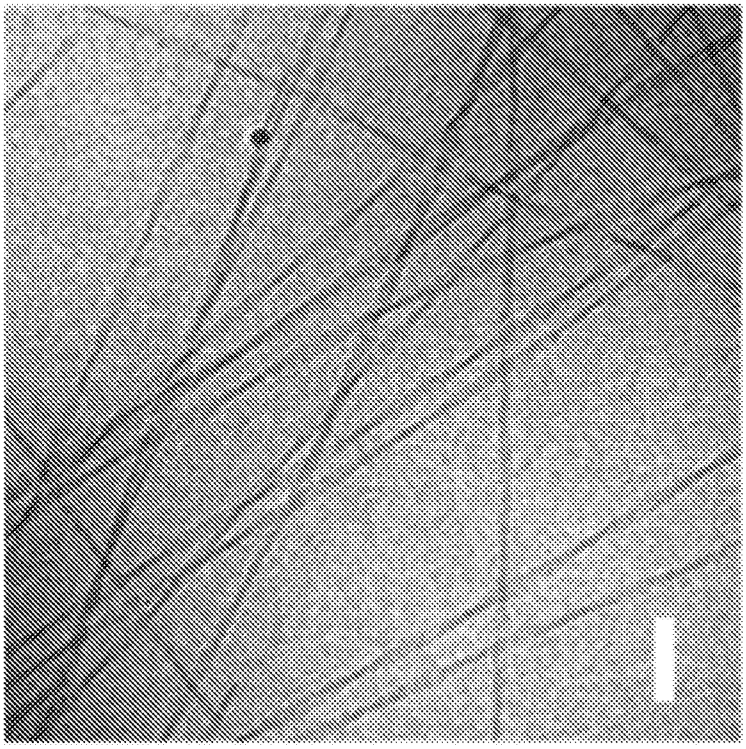
Figure 16D:
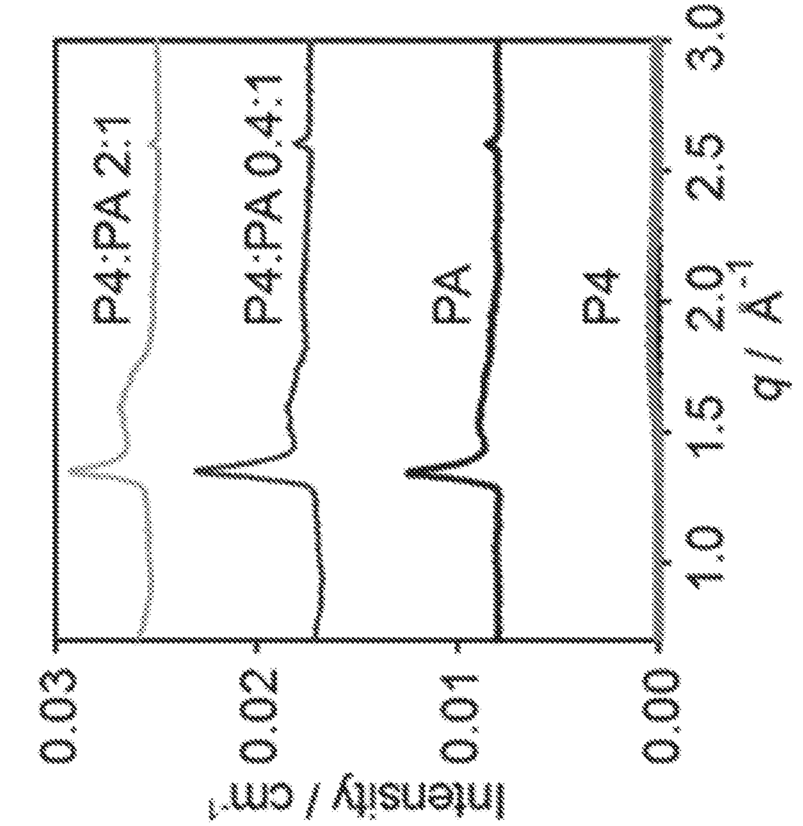
Figure 16C:
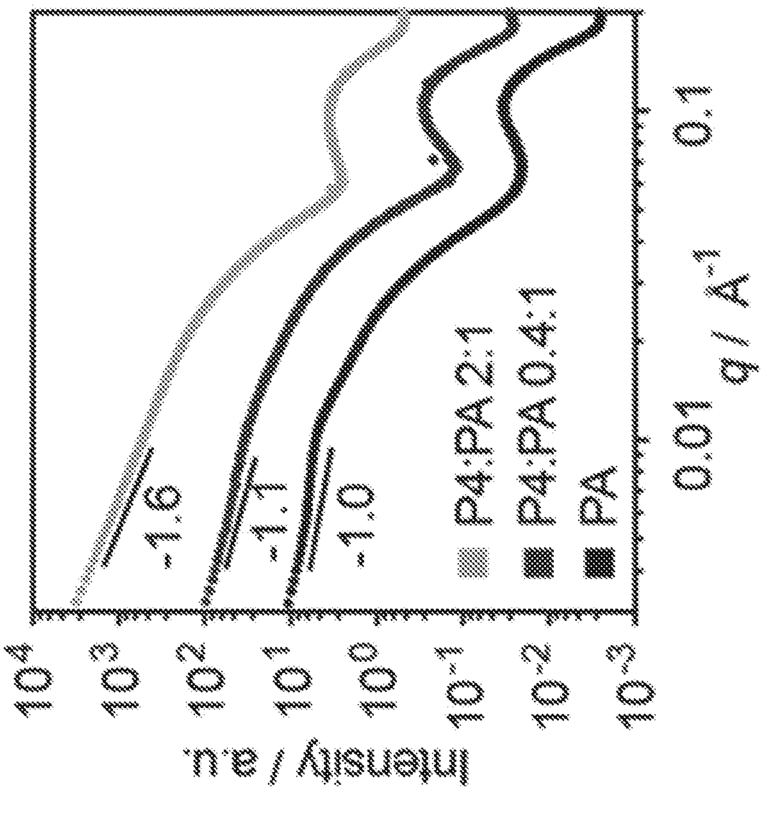
Figures 17A, 17B:
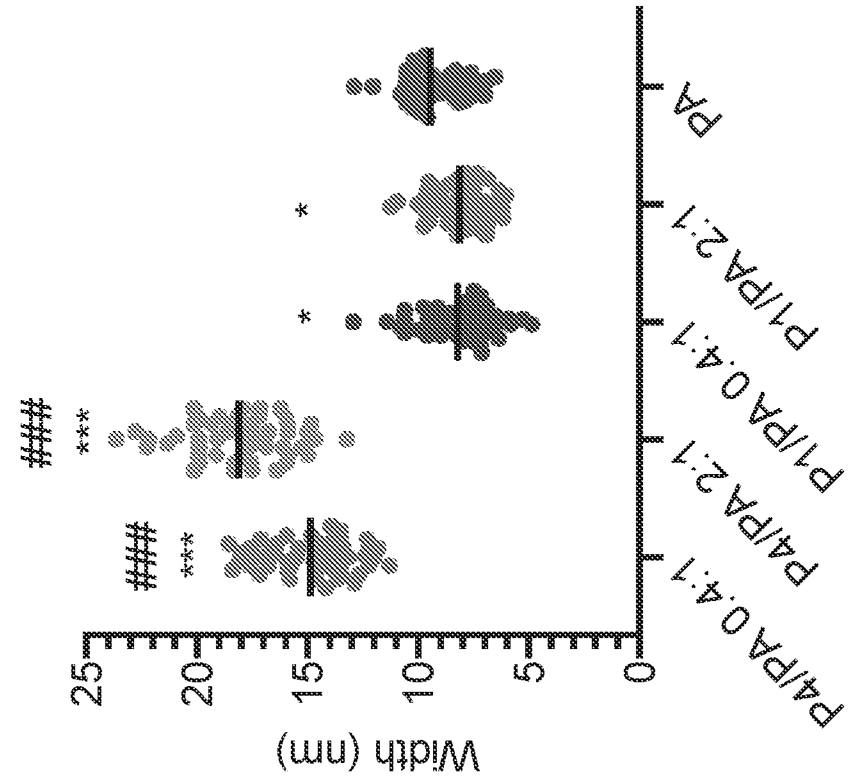
FIG. 17. Histogram analysis (FIG. 17A) and average values (FIG. 17B) of the nanoribbon width formed by the non-annealed P4/PA co-assemblies, P1/PA co-assemblies and PA. One-way ANOVA with the Bonferroni test is used: *p<0.001, p<0.01, *p<0.05 vs PA, ###p<0.001 vs P1/PA of the same co-assembly ratio. Results were based on 50 iterations of measuring the widest region on the nanoribbon.
Figure 18:
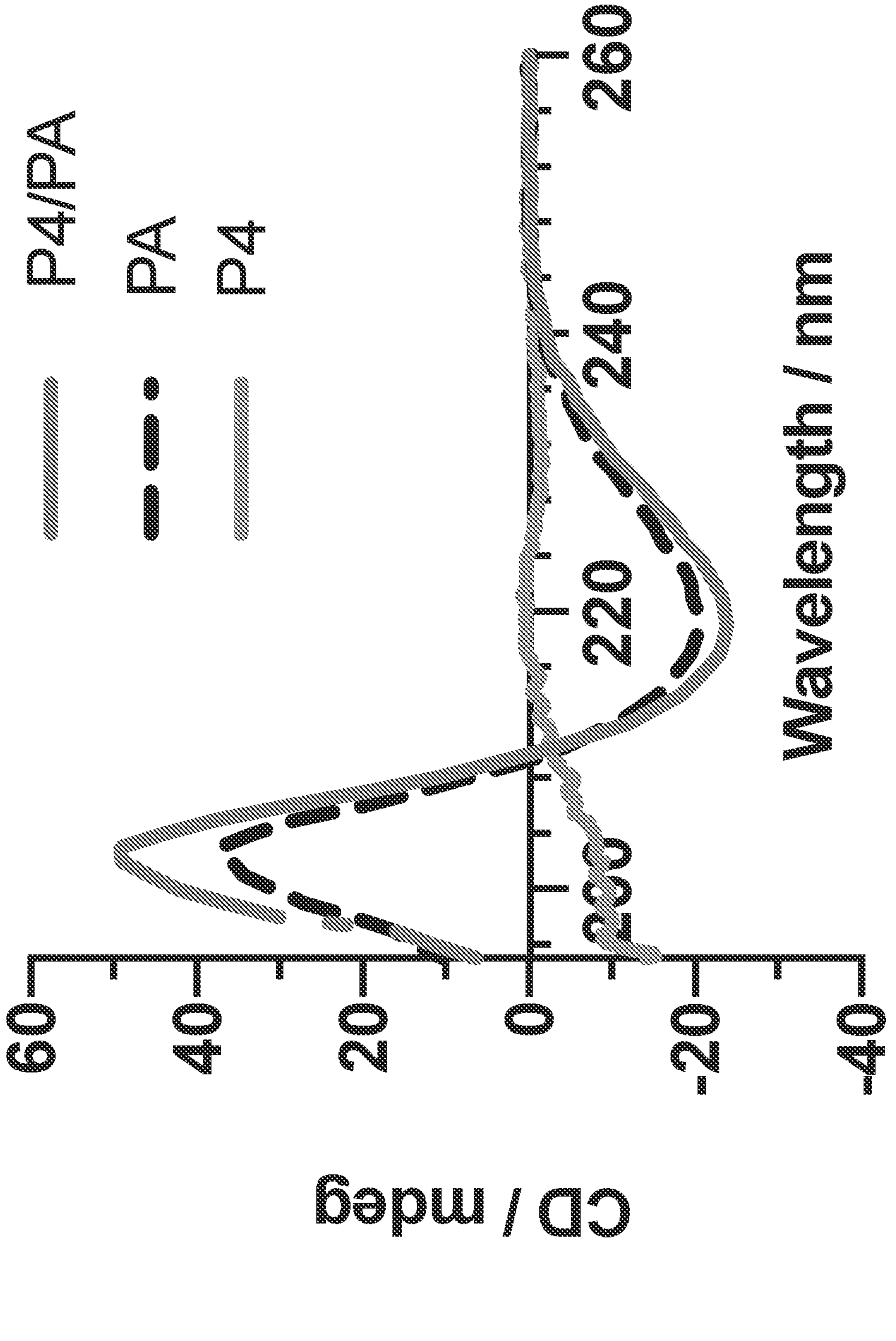
FIG. 18. CD spectrum of aged P4/PA 0.4:1, PA and P4 alone.

Cryo-TEM showed that P4/PA co-assemblies at low (P4/PA 0.4:1, FIG. 16A) and high (P4/PA 2:1, FIG. 16B) peptide concentrations formed long nanoribbons, as opposed to the short nanoribbons formed by P1/PA 2:1 (FIG. 7D). Moreover, the SAXS slopes in Guinier region were −1.1 for 0.4:1 P4/PA co-assembly and −1.6 for 2:1 P4/PA co-assembly (FIG. 16C), consistent with the cryo-TEM observation that shows a ribbon-like nanostructures with average widths of 14.9 nm for 0.4:1 P4/PA and 18.1 nm for 2:1 P4/PA, respectively. In contrast, P1/PA co-assemblies displayed a SAXS slope of −1.0 for peptide/PA molar ratios of 0.4:1 and 2:1, which is also consistent with the cryo-TEM images showing a narrower ribbon-like nanostructure with average widths of 8.25 nm for 0.4:1 P1/PA and 8.16 nm for 2:1 P1/PA (FIG. 17). The β-sheet secondary structure of P4/PA co-assemblies was confirmed by CD spectroscopy (FIG. 18) and further analyzed by WAXS (FIG. 16D). Similar to the trend that has been observed with model peptides P1-P3, a small amount of P4 addition stabilizes the PA β-sheet motif evidenced by the increased β-sheet content on WAXS at P4/PA 0.4:1; the P4/PA co-assembly at high peptide concentrations represented by 2:1 has reduced β-sheet content. P4 alone as a soluble peptide does not form regular nanostructures or β-sheet.

Figure 16F:
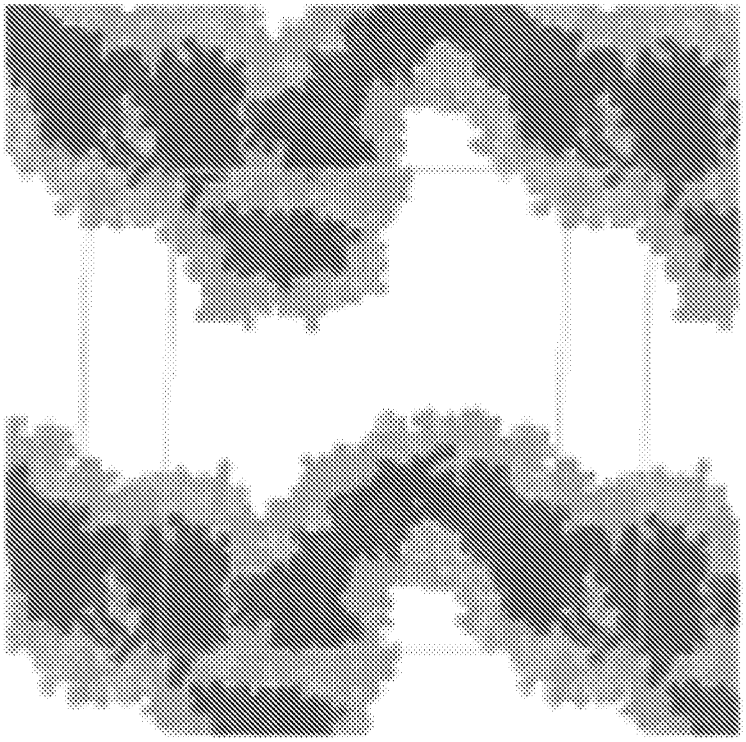
Figure 16E:
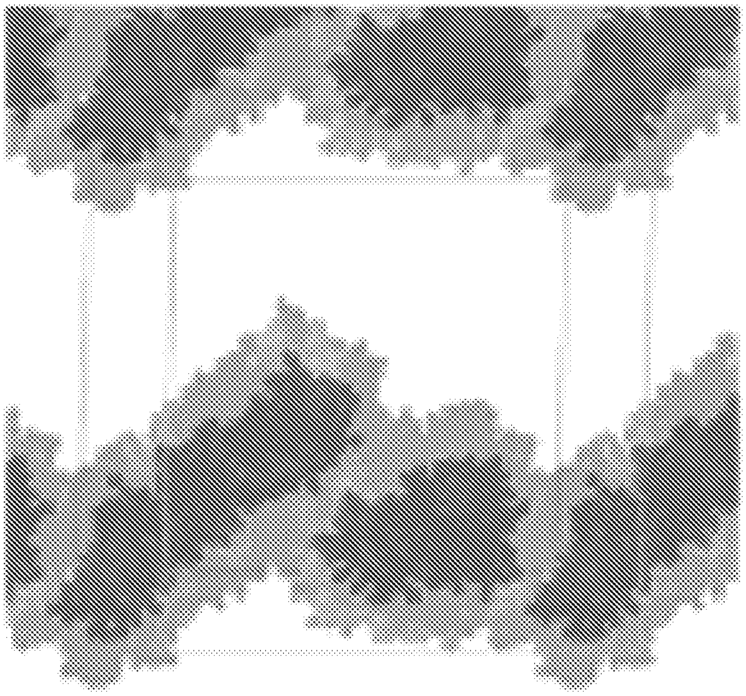
Figure 16G:
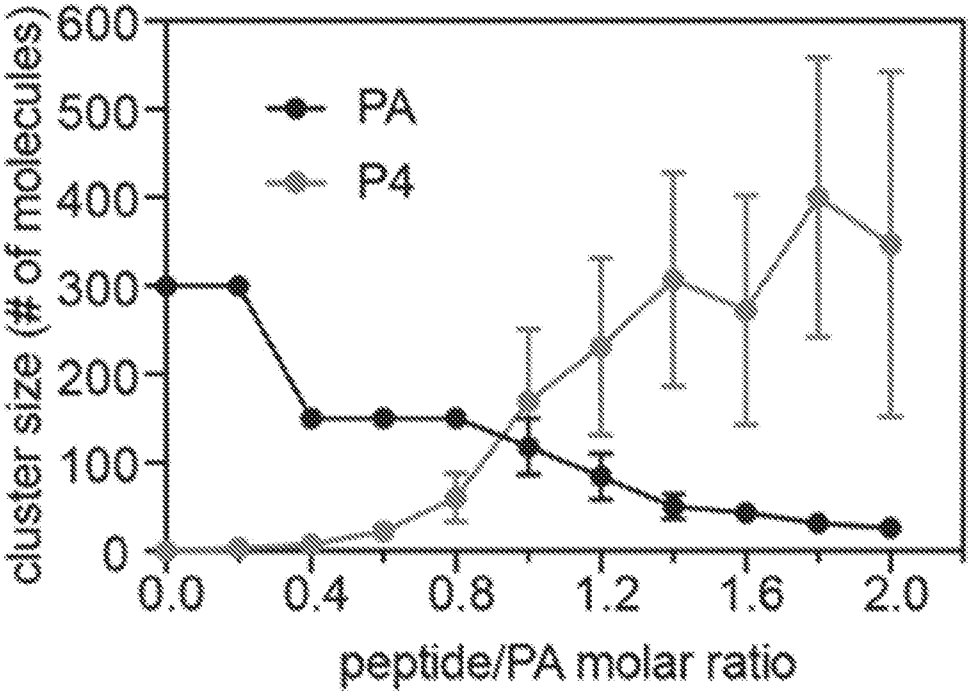
Figure 16H:
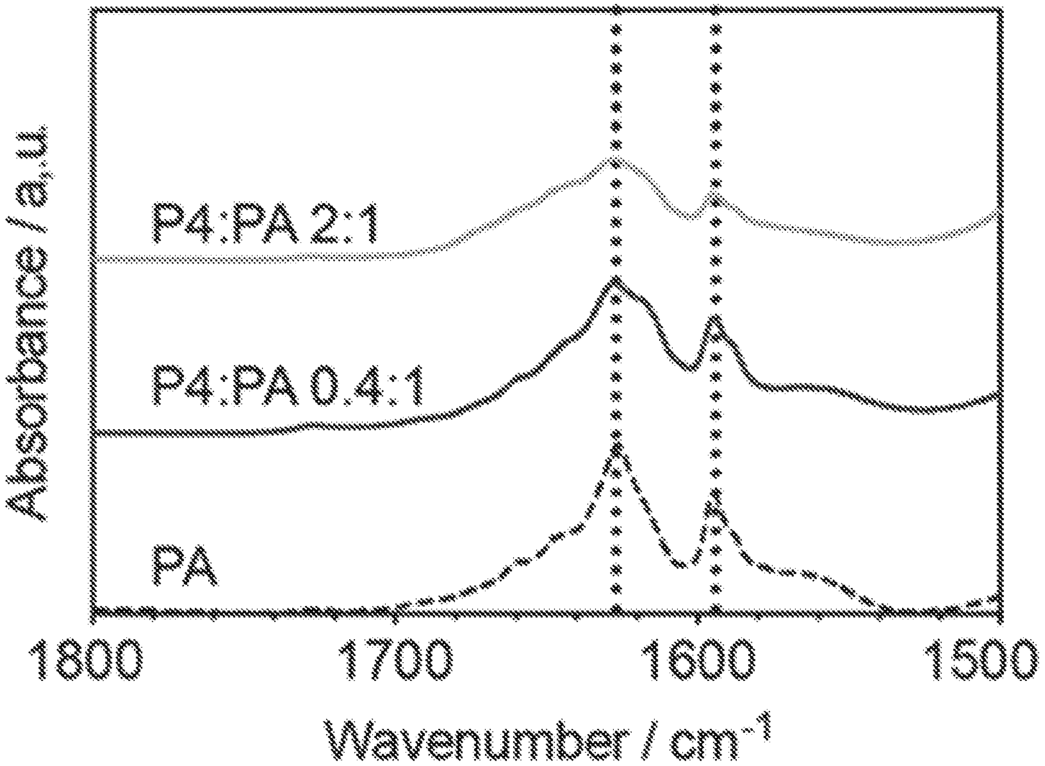
Figure 16I:
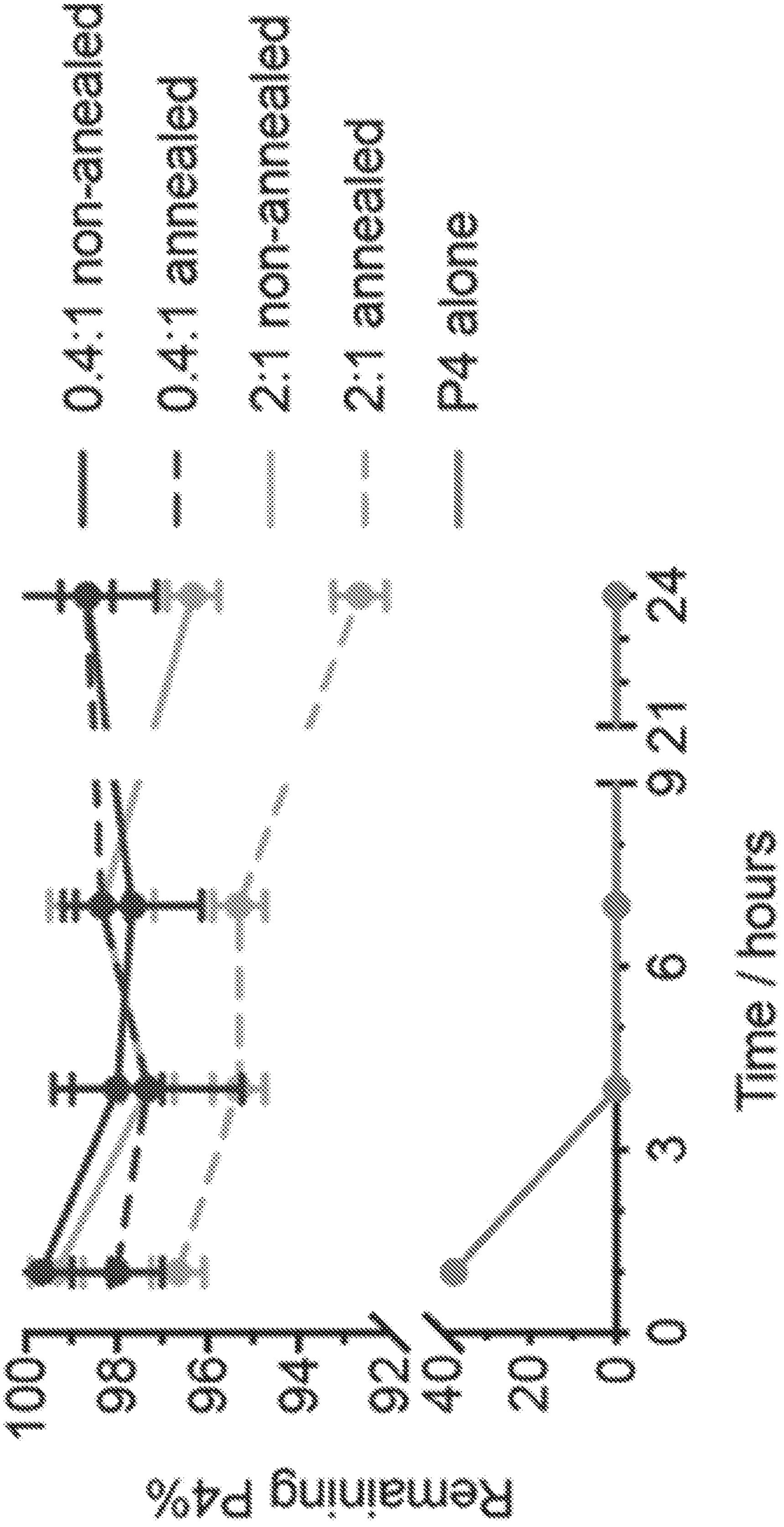
Figure 19:
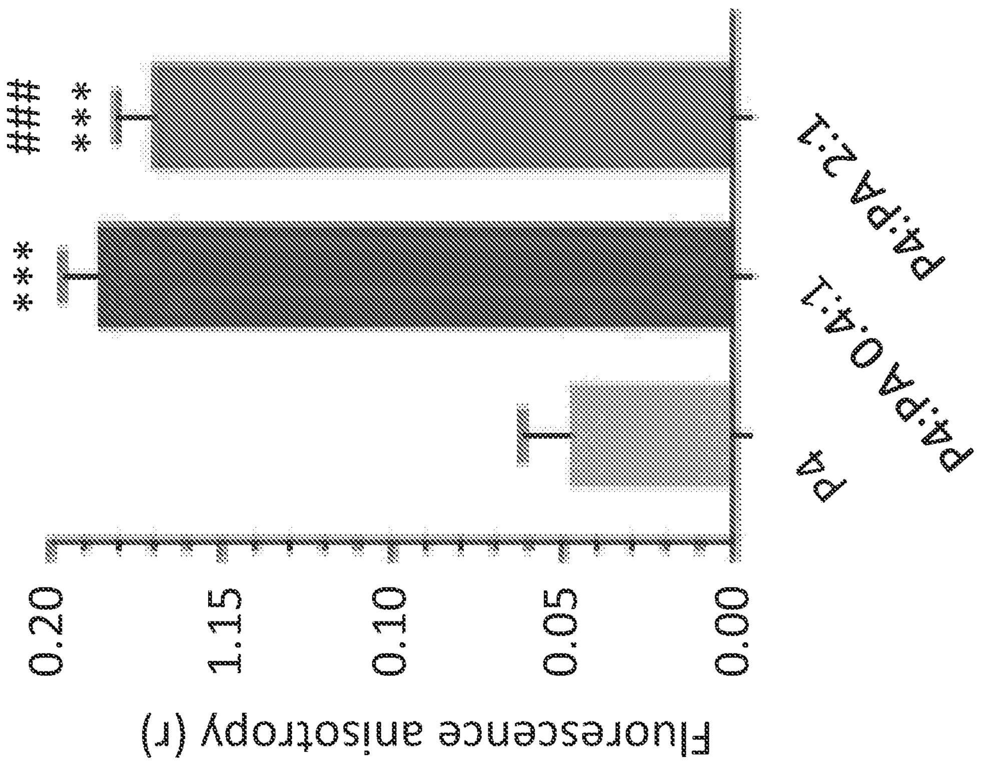
FIG. 19. Fluorescence anisotropy of P4 alone or co-assembled with PA at a molar ratio of 0.4:1 and 2:1. One-way ANOVA with the Bonferroni test is used: ***p<0.001 vs P4, ###p<0.001 vs P1/PA 0.4:1.
Figure 20:
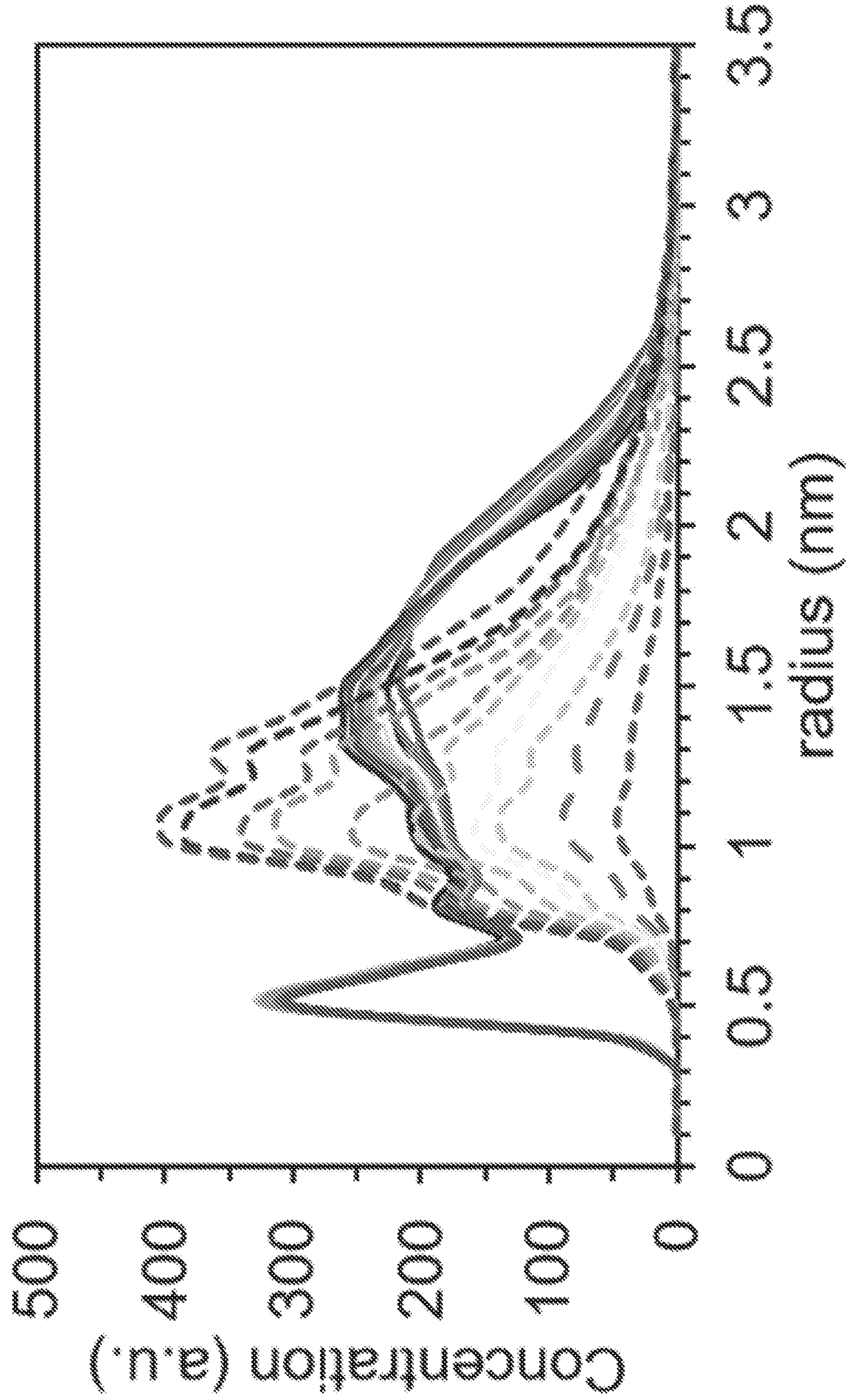
FIG. 20. Radial distribution of PA (solid line) and P4 (dashed line) within P4/PA co-assemblies at increasing P4 concentrations.

The molecular mobility of P4 within the PA co-assemblies without annealing was measured by fluorescence anisotropy, showing a significant decrease compared to P4 alone (FIG. 19). Consistent with observations for P1, the 2:1 co-assembly of P4 with PA was slightly more mobile than 0.4:1 as a result of the less ordered internal structure at high free peptide content. However, the anisotropy values of the co-assembled P4 were generally higher than co-assembled P1, possibly due to the higher hydrophobicity of P4 sequence. The coarse-grained simulation and FTIR spectroscopy revealed the molecular distribution of P4/PA co-assemblies. The simulation results suggested that at low free peptide content (FIG. 16) and high free peptide content (FIG. 16F), P4 was able to co-assemble with PA, resulting in nanoribbons in which the hydrophobic core of stacked PA alkyl tails stayed intact at low peptide content and broken up at high peptide content. The cluster analysis quantitively described that the PA cluster could tolerate peptide addition at P4/PA 0.2:1 and started disintegrating upon further increased peptide concentrations (FIG. 16G). In addition to these internal structural features in common with P1/PA co-assemblies, the hydrophobic core of PA shrinks at high P4 content as illustrated in FIG. 16F. Radial distribution analysis with varying P4 concentrations further explained the molecular alignment of the peptide and PA (FIG. 20). The presence of P4 causes the fibers to shrink by up to 0.2 nm and narrowing the PA distribution by 0.8-1.7 nm. The distribution of the P4 shows that the high hydrophobicity and short length makes them remain close to the aliphatic tail even with high ratios of peptide, which could explain the disruptive effect on β-sheet as well as the deformation of PA hydrophobic core at high P4 content. Relative to P1, the cluster size of P4 molecules increased much more dramatically with increasing peptide content, indicating the strong tendency for P4 to form clusters within the nanoribbons. FTIR spectroscopy that employed $^{13}$C-PA and P4 (FIG. 16H) revealed that the 1593 cm' peak was fully retained for P4/PA ratio of 0.4 and weakened but still present in 2:1 P4/PA mixtures. This result also supports that the excess P4 forms clusters in the nanostructure, preventing the decoupling of β-sheet hydrogen bonding between PAs. Collectively these data show that even though the sequence of P4 is quite different from the PA, it can still co-assemble with PA due to the hydrophobic interactions among the peptide residues.

Figure 16J:
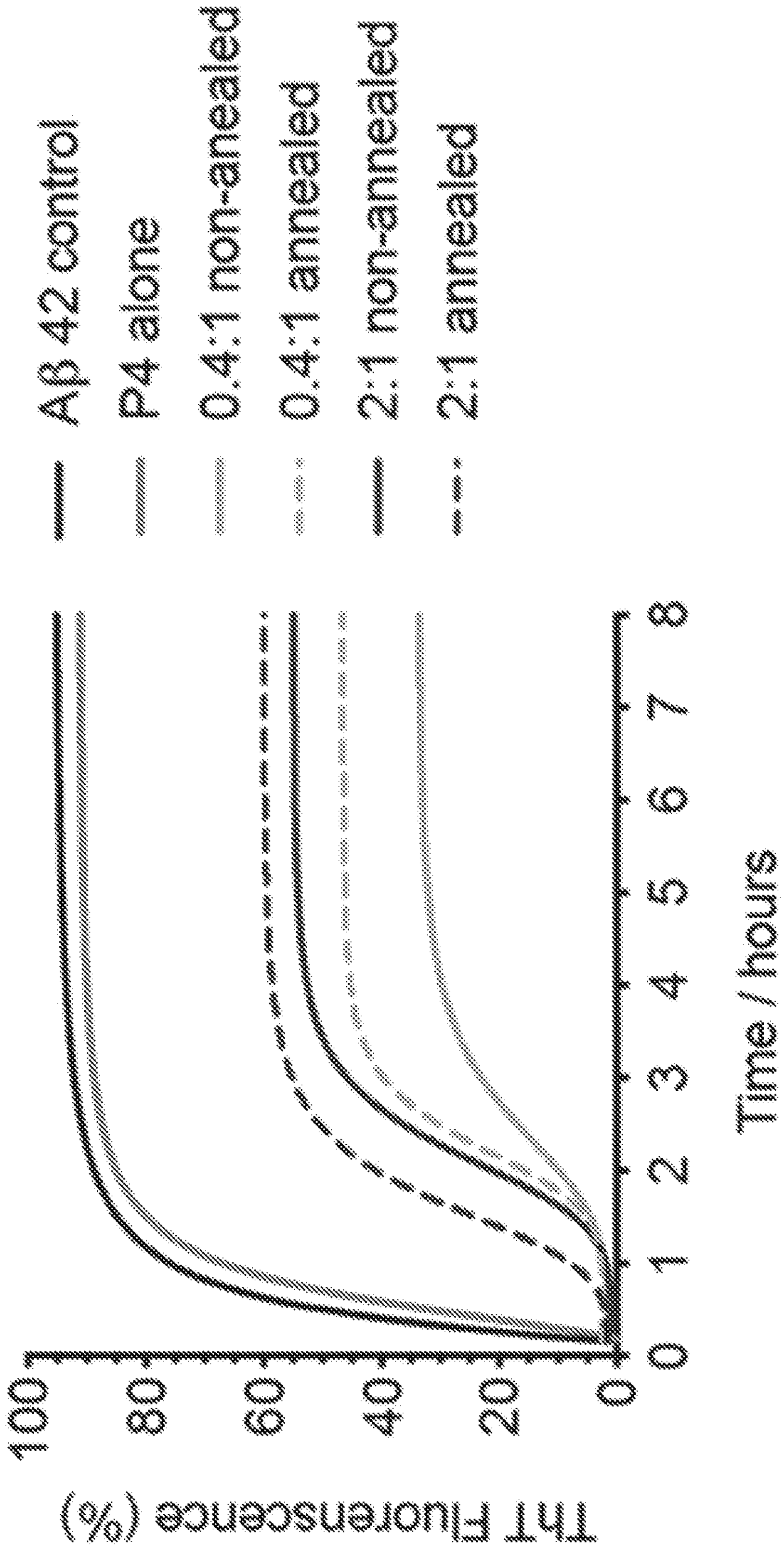

To explore the therapeutic potential of P4/PA co-assemblies, P4 alone as well as P4/PA co-assemblies were exposed to chymotrypsin in an enzymatic degradation test (FI. 16I). At 12.5 μg/mL chymotrypsin, P4 alone was degraded completely in 4 hours, whereas greater than 90% of the P4 peptide was observed in the P4/PA co-assemblies after 24 hours. For the P4/PA co-assemblies without annealing, no statistically significant difference of P4 stability was observed between 0.4:1 and 2:1 over 24 hours. For the annealed co-assemblies, P4 in 0.4:1 P4/PA showed better stability than in 2:1. Moreover, the non-annealed P4/PA 2:1 was able to prevent more peptide decomposition than the annealed 2:1 P4/PA, although there was no statistically significant difference between the non-annealed and annealed 0.4:1 P4/PA co-assemblies. The P4/PA co-assemblies and P4 alone were incubated at 37° C. with monomeric Aβ42 and the aggregation was monitored by a thioflavin T (ThT) fluorescence assay, which has been widely used for monitoring amyloid fibrillation where the fluorescence intensity is quantitively correlated with β-sheet formation.[14] To eliminate the contribution of the ThT fluorescence signal given by the β-sheet structured peptide/PA co-assemblies, the fluorescence intensity was recorded in the absence of Aβ42 and subtracted as background. The total molar concentration of peptide alone, PA alone as well as peptide and PA co-assembly at different molar ratios was consistent as 30 μM for potency comparison. As shown in FIG. 16J, non-annealed P4/PA 0.4:1 showed 64% reduced signal relative to Aβ 42 alone, which was interpreted as 64% inhibition of β-sheet aggregation. The non-annealed P4/PA co-assemblies displayed more inhibition than the annealed sample, consistent with better peptide stability of non-annealed P4/PA co-assemblies, highlighting the biological functions of the metastable states of these co-assembled structures. Surprisingly, the PA alone with and without annealing also displayed Aβ42 aggregation inhibition at 34% and 22%, respectively (FIG. 21), implying the presence of an interaction between PA and Aβ42 monomers.

Figure 22:
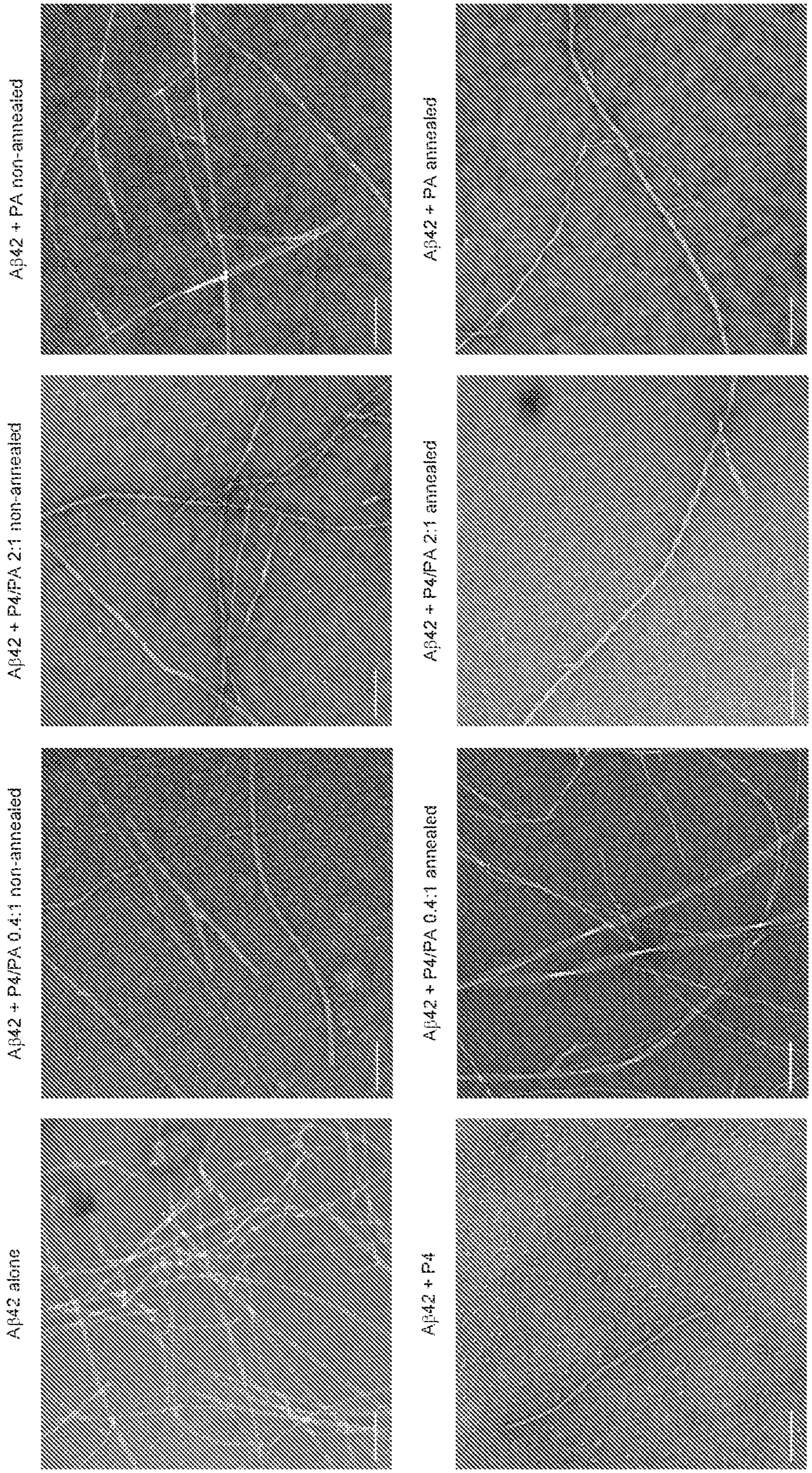
FIG. 22. Representative negative staining TEM images of Aβ42 incubated under 37° C. for 16 hours without or with PA or P4 alone, P4/PA co-assemblies at non-annealed and annealed states. Scale bar is 100 nm.

To characterize the morphology of Aβ42 aggregated in the presence of P4/PA co-assemblies, monomeric Aβ42 was incubated by itself, with P4 alone, with PA alone, or with P4/PA co-assemblies for 16 hours at 37° C., and the resulting solutions were imaged by negatively stained TEM (FIG. 22). Similar to previously reported results[13], Aβ42 alone formed long fibril structures with diameter of approximately 6 nm, while mostly micelles and very few fibrils of reduced length were observed when Aβ42 was co-incubated with P4 alone. The Aβ42 with either non-annealed P4/PA co-assemblies or self-assembled PA alone displayed a mixture of micelles and fibrils that were polydisperse in width. In contrast, we observed intertwined fibers when Aβ42 was mixed with the annealed P4/PA co-assemblies. These changes in morphology are supported by the results from ThT assays which showed that Aβ42 aggregation from monomers towards fibrils is disrupted in the presence of PA assemblies.

Figure 23A:
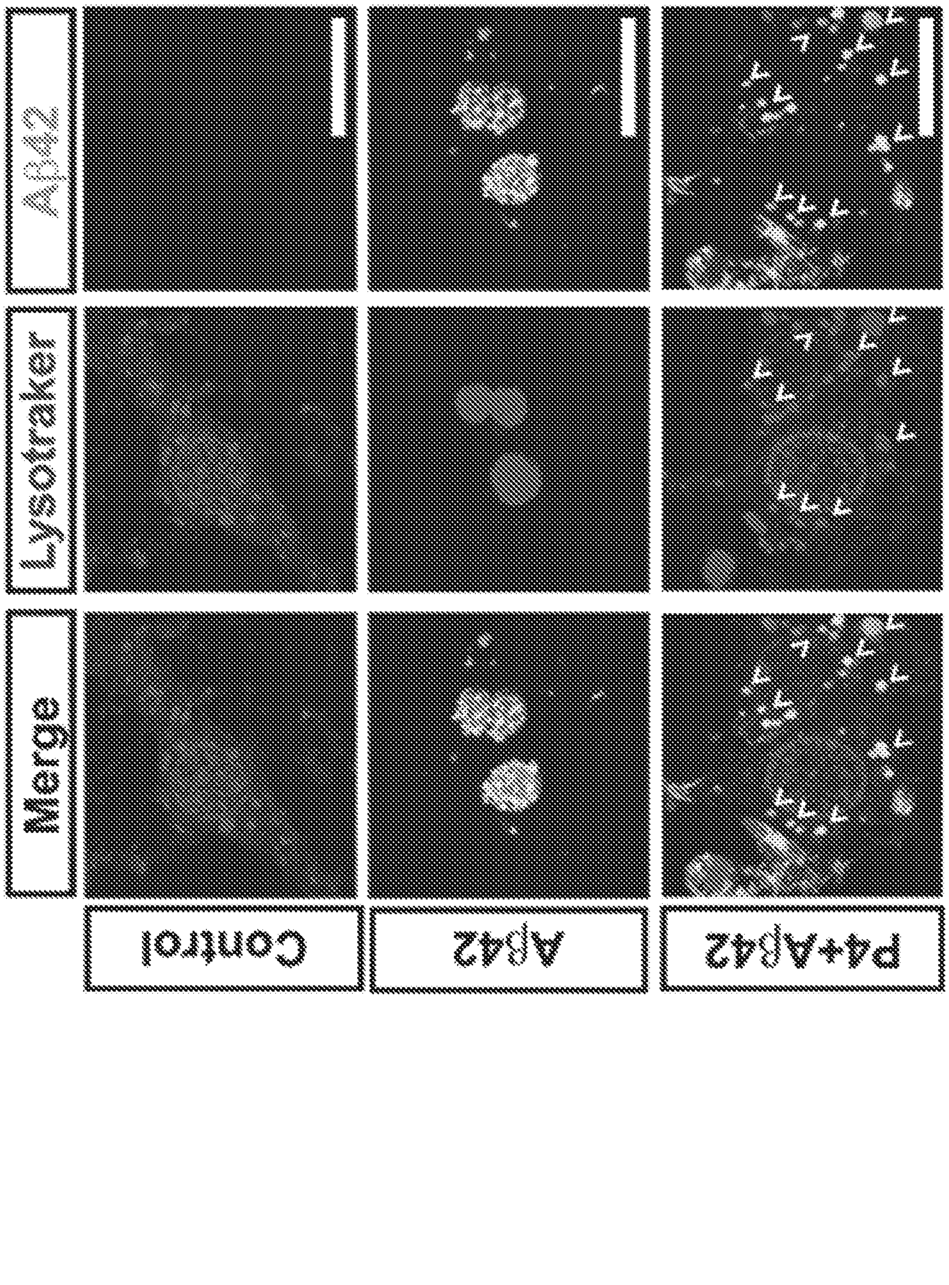
(FIG. 23A-23B) Representative confocal images of neurons stained with Lysotracker (blue, lysosomes), Aβ42-HiLyte488 (green, Aβ42), PA-TAMRA (red, PA) treated with Aβ42, P4, PA and P4/PA at 0.4:1 and 2:1 (non-annealed) for 24 h. Scale bar 10 μm.
Figure 23B:
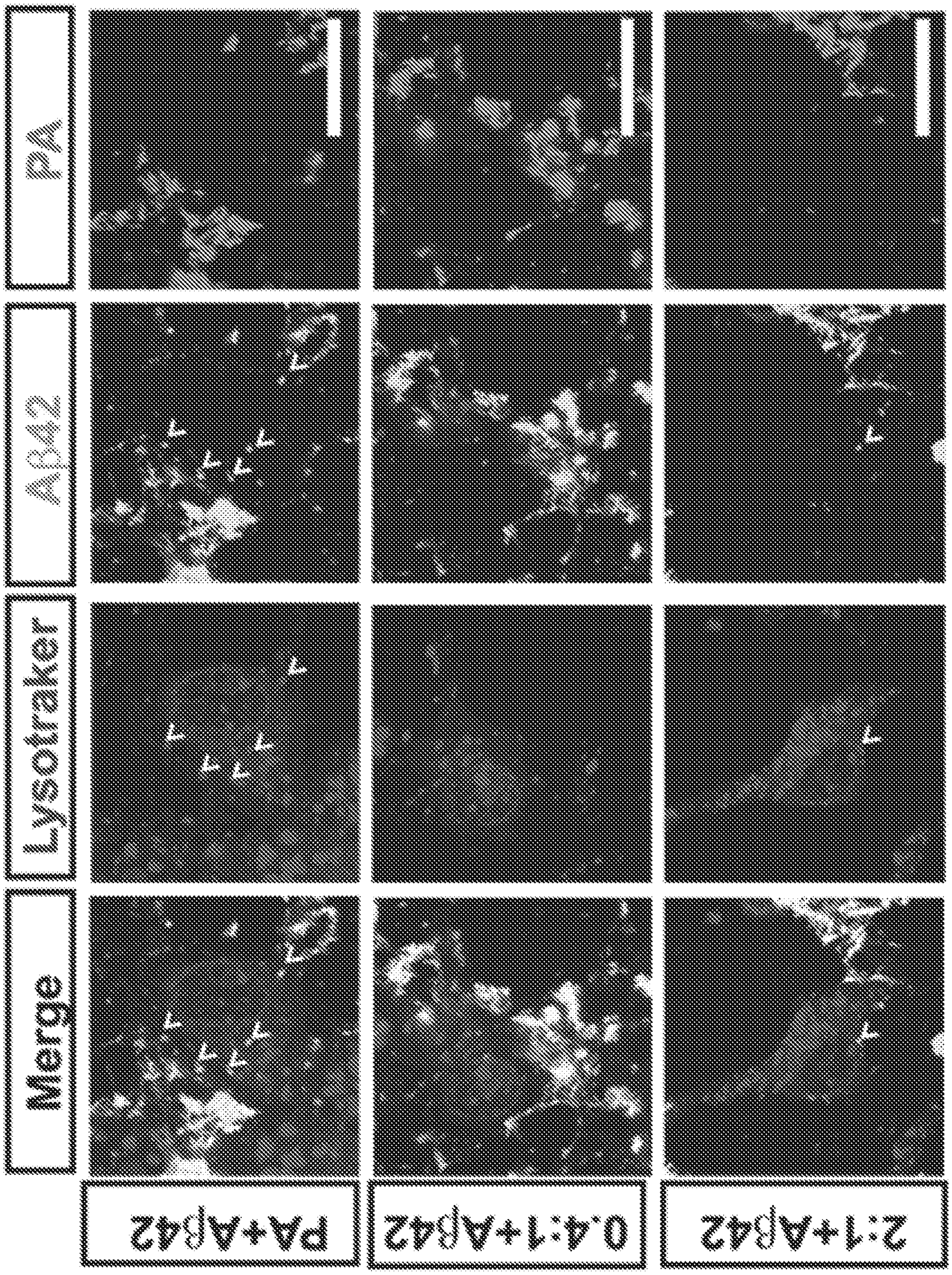

Given the inhibition activity of P4/PA co-assemblies on Aβ42 aggregation in ThT fluorescence assay, it was next explored whether these co-assemblies were able to inhibit primary mouse cortical neuron death in the presence of Aβ42. Aβ42 has been reported to be internalized into a variety of cell types, including cortical neurons, and induce neurotoxicity by triggering intracellular pathways.[15] Both non-annealed and annealed P4/PA as well as self-assembled PA alone were applied in primary neuronal cultures to investigate how the switch from metastable state to equilibrated state would influence neurotoxicity. To gain mechanistic insights into the biological function of the supramolecular assemblies on suppressing Aβ42 neurotoxicity, in situ confocal microscopy was employed to characterize the uptake and intracellular localization of Aβ42. The PA and Aβ42 were fluorescently labeled by replacing 5 mol % of the molecules with TAMRA-conjugated PA and HiLyte488-conjugated Aβ42, respectively. Cortical neurons were treated with Aβ42 pre-incubated for 16 hours with P4, PA and P4/PA at 0.4:1 and 2:1 ratio. Fluorescent images acquired after 24 hours of treatment showed that Aβ42 (10 mM) caused cell death due to Aβ42 aggregation into oligomers, which are toxic to neuronal cells. Aβ42 in the presence of P4 (30 mM) and PA alone (30 mM) appeared as granular intracellular deposits and colocalized with LysoTracker-405, confirming their compartmentalization within acidic organelles (FIG. 23A-23B). No visible Aβ42 was seen inside neurons in the presence of the non-annealed PA/P4 assemblies while cells treated with annealed PA/P4, showed a high uptake of Aβ42 in their cytoplasm (FIG. 24).

Figure 23C:
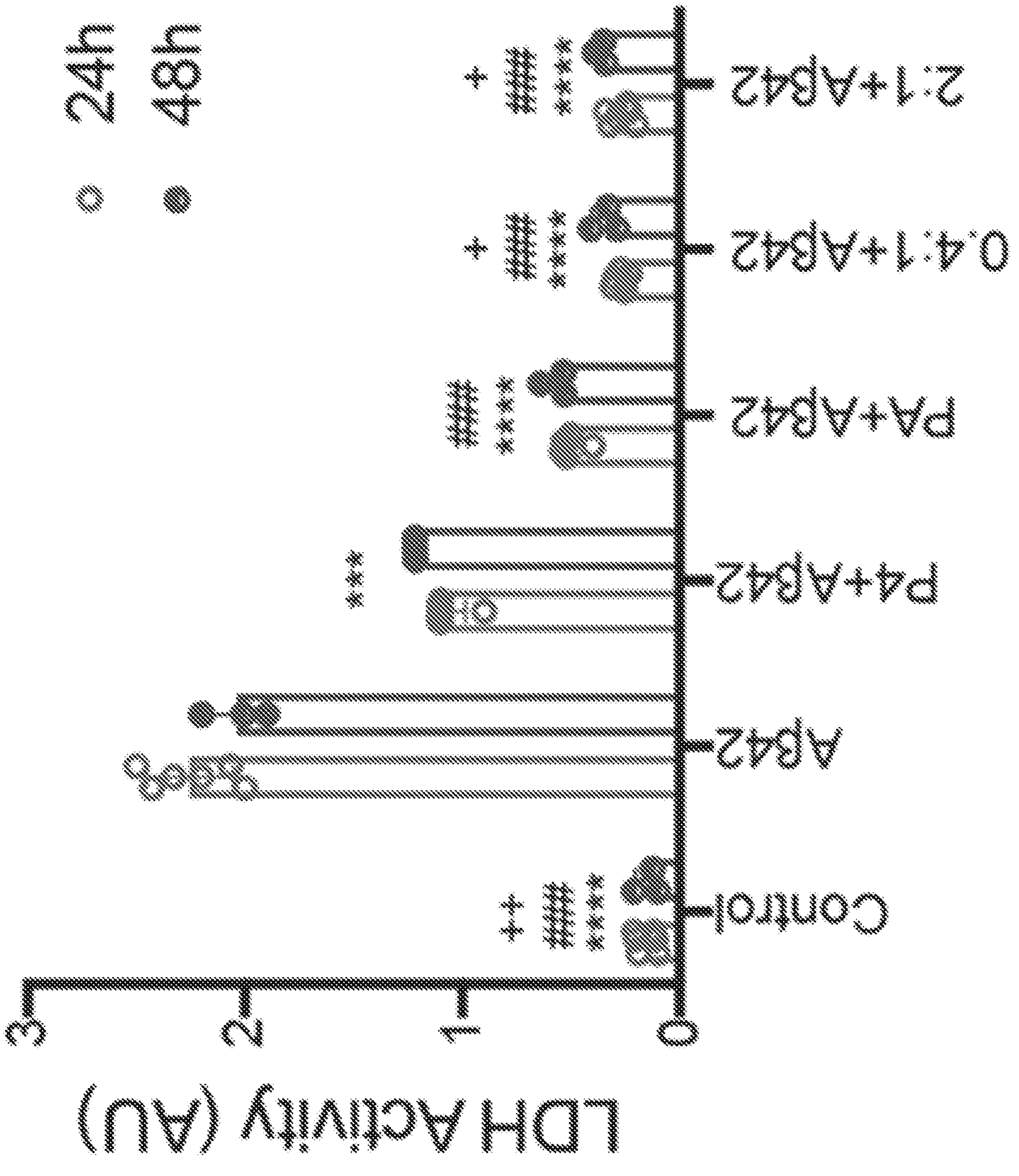
(FIG. 23C) Cell viability assessed by LDH assay in primary neurons treated with Aβ42, P4, PA and P4/PA at 0.4:1 and 2:1 (non-annealed) for 24 h and 48 h.
Figure 23D:
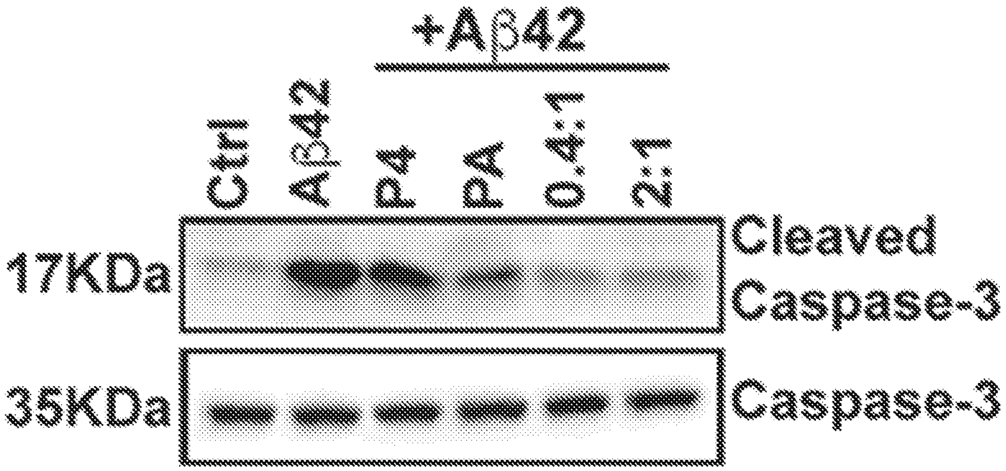
(FIG. 23D) Representative WBs of Cleaved Caspase-3 and Caspase-3 in neurons treated with Aβ42, P4, PA and P4/PA at 0.4:1 and 2:1 (non-annealed) for 12 h.
Figure 23E:
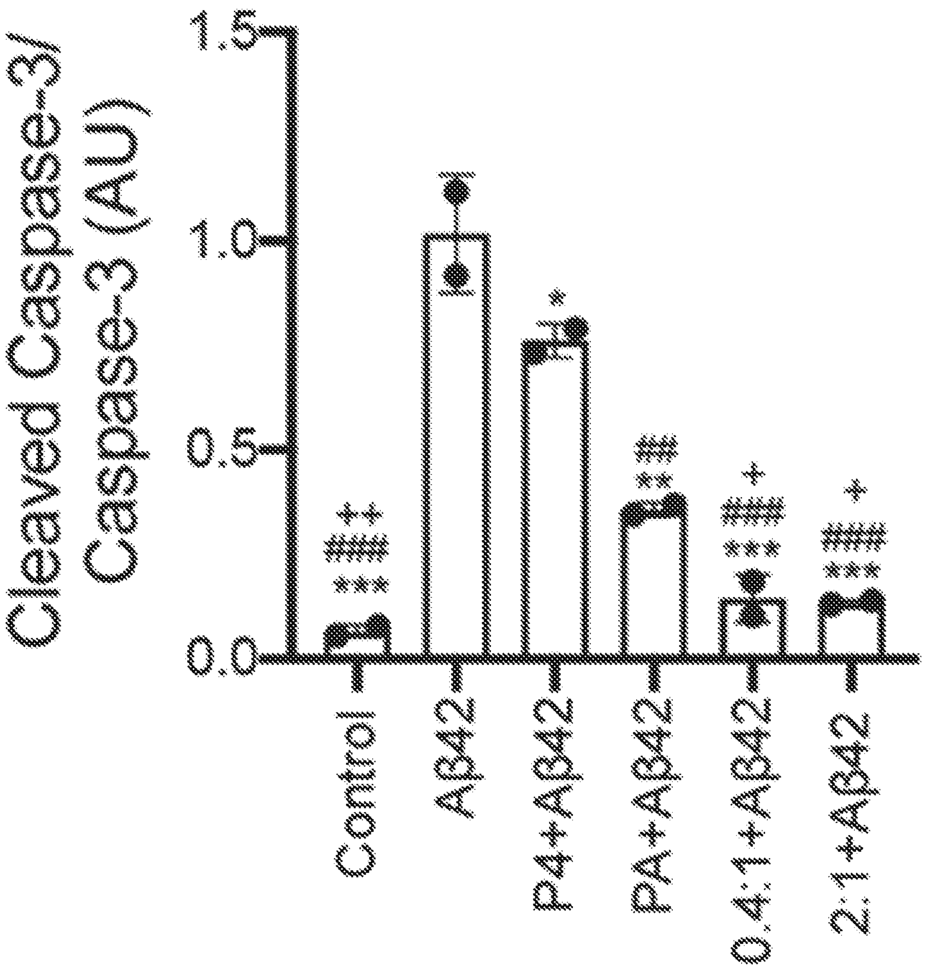
(FIG. 23E) Dot plot representing the normalized protein levels of cleaved caspase-3 at 12 h in the conditions referred to in FIG. 23D. One-way ANOVA with the Bonferroni test is used: *p<0.001, p<0.01, *p<0.05 vs Aβ42, ###p<0.001, ##p<0.01, *p<0.05 vs P4+Aβ42 and +p<0.05 vs PA+Aβ42.
Figure 24A:
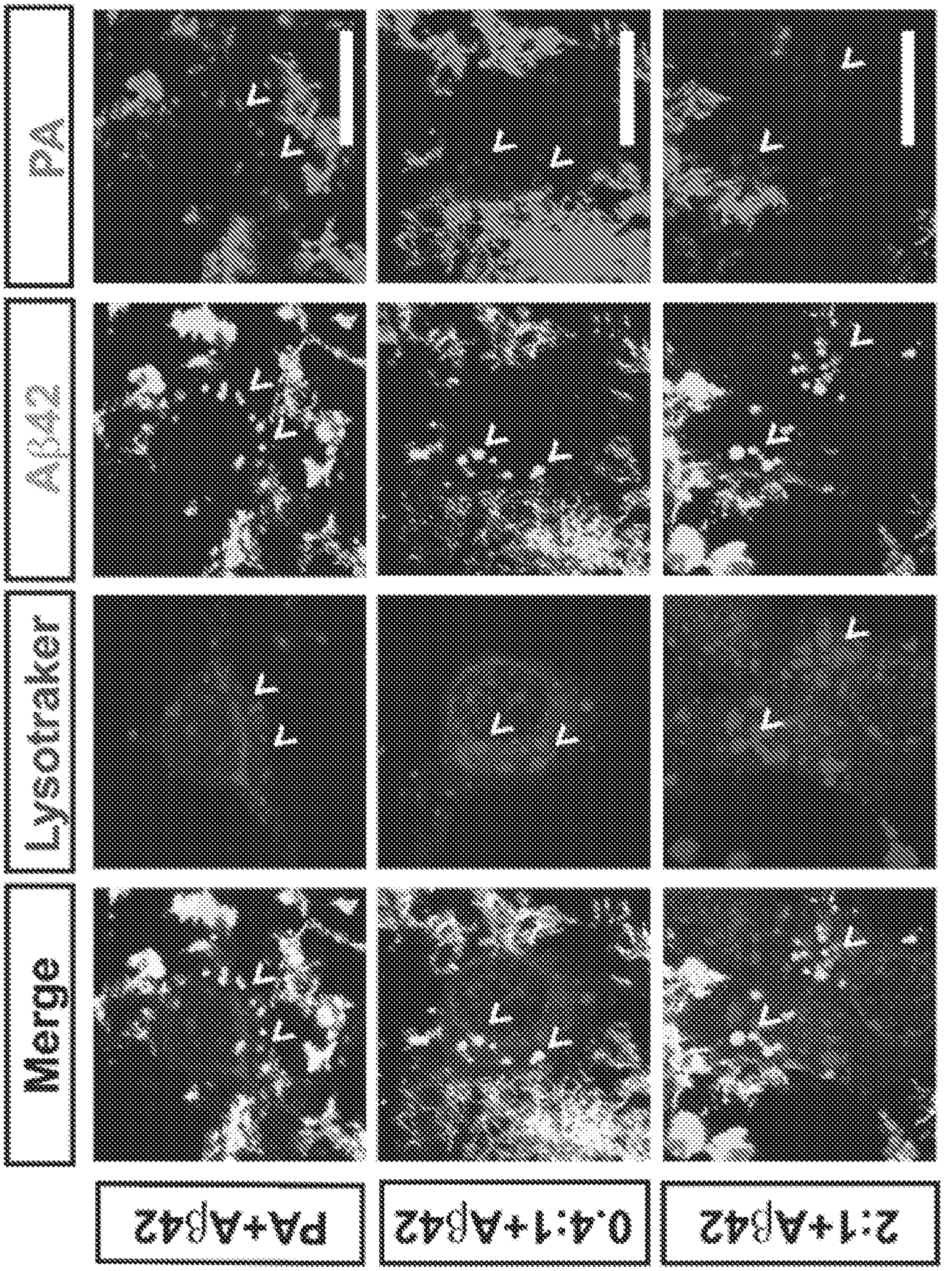
(FIG. 24A) Representative confocal images of neurons stained with Lysotracker (blue, lysosomes), Aβ42-Alexa488 (green, Aβ42), PA-TAMRA (red, PA) treated with PA and P4/PA at 0.4:1 and 2:1 (annealed) for 24 hours. Scale bar 10 μm.
Figure 24B:
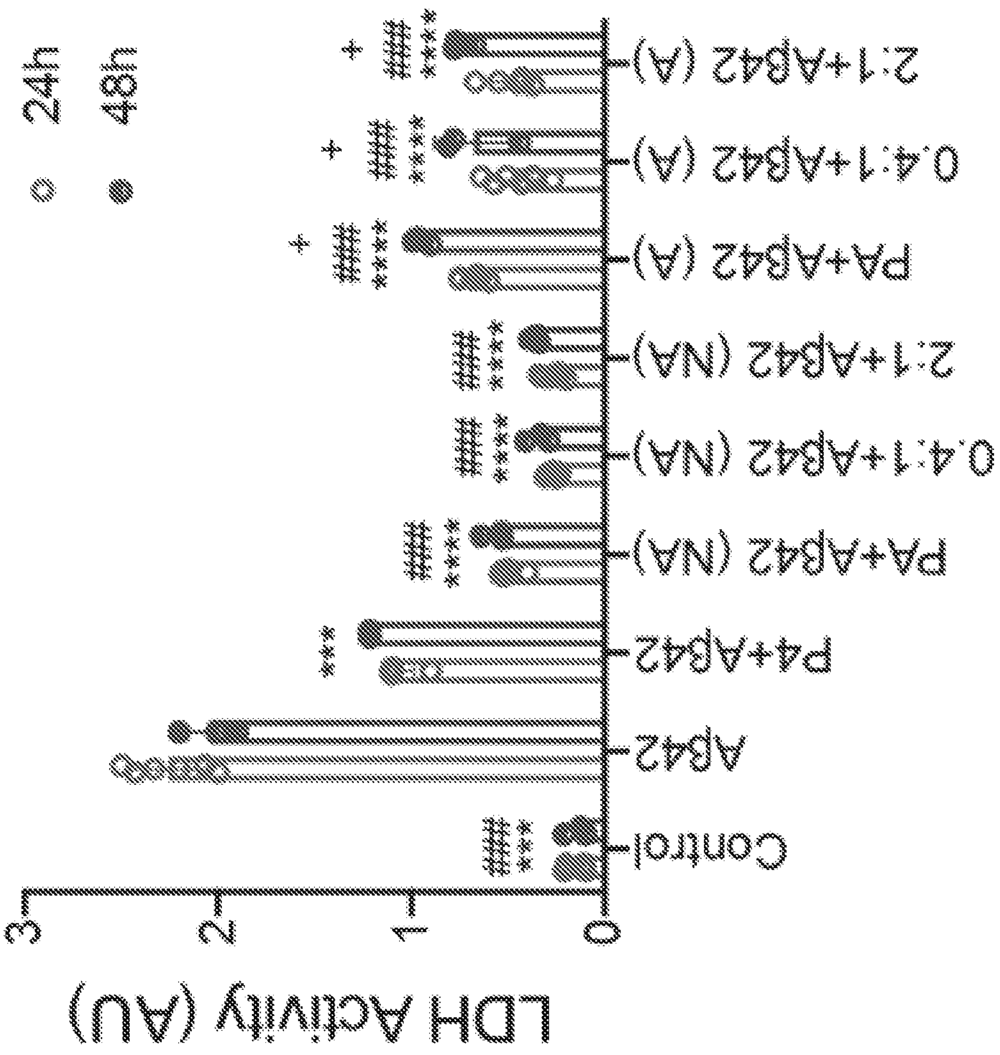
(FIG. 24B) Cell viability assessed by LDH assay in primary neurons treated with Aβ42, P4, PA and P4/PA annealed (A) and non-annealed (NA) at 0.4:1 and 2:1 for 24 and 48 hours.
Figure 24D:
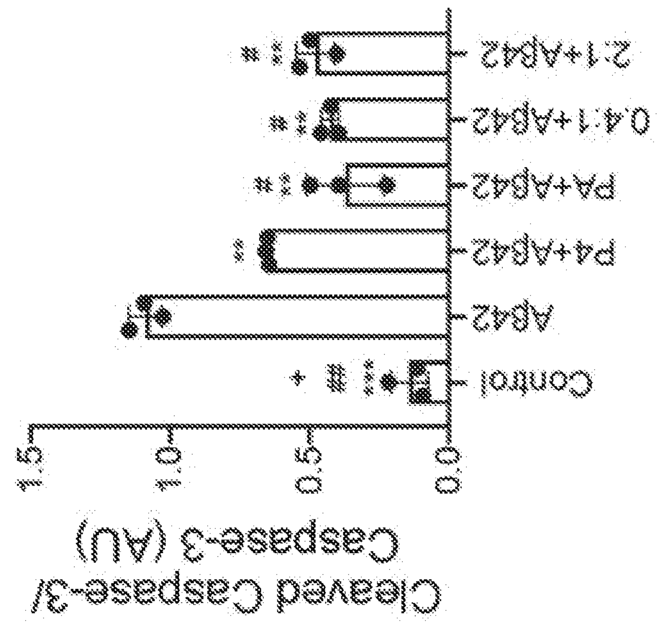
(FIG. 24D) Dot plot representing the normalized protein levels of cleaved caspase-3 at 12 h in the conditions referred on c.
Figure 24C:
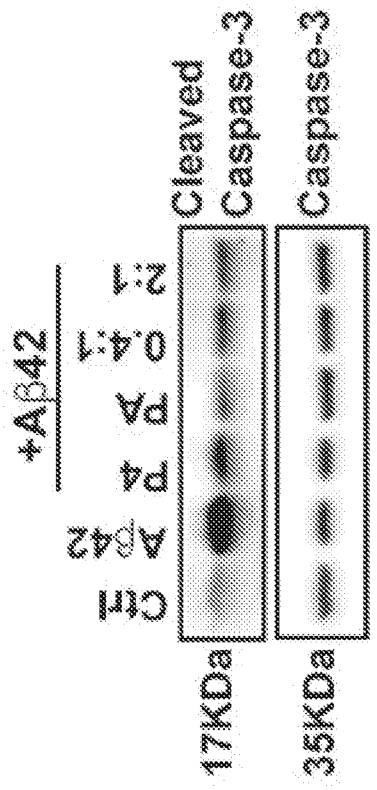
(FIG. 24C) Representative WBs of Cleaved Caspase-3 and Caspase-3 in neurons treated with Aβ42, P4, PA and P4/PA annealed at 0.4:1 and 2:1 for 12 hours. One-way ANOVA with the Bonferroni test is used: *p<0.001, p<0.01, *p<0.05 vs Aβ42, ###p<0.001, ##p<0.01, vs P4+Aβ42 and +p<0.05 vs non-annealed (NA) PAs.
Figure 24E:
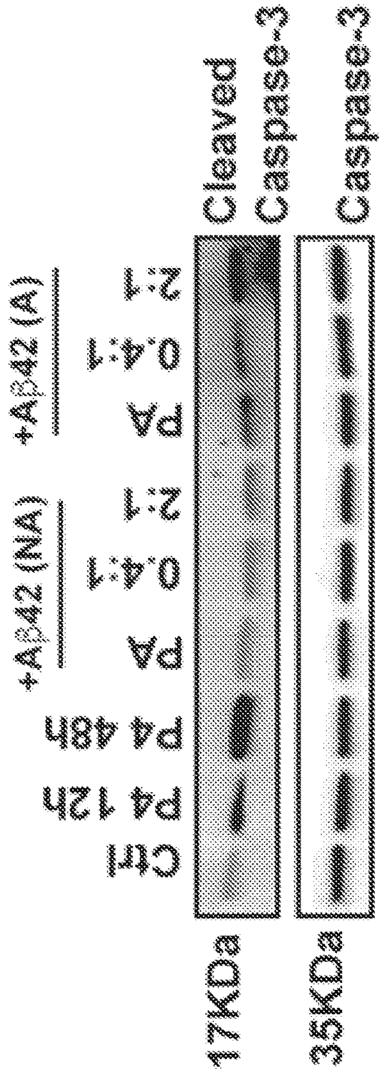
(FIG. 24E) Representative western-blots (WBs) of Cleaved Caspase-3 and Caspase-3 in neurons treated with P4 at 12 and 48 hours, nonannealed (NA) or annealed (A) PA and P4/PA at 0.4:1 and 2:1 for 48 hours.
Figure 24F:
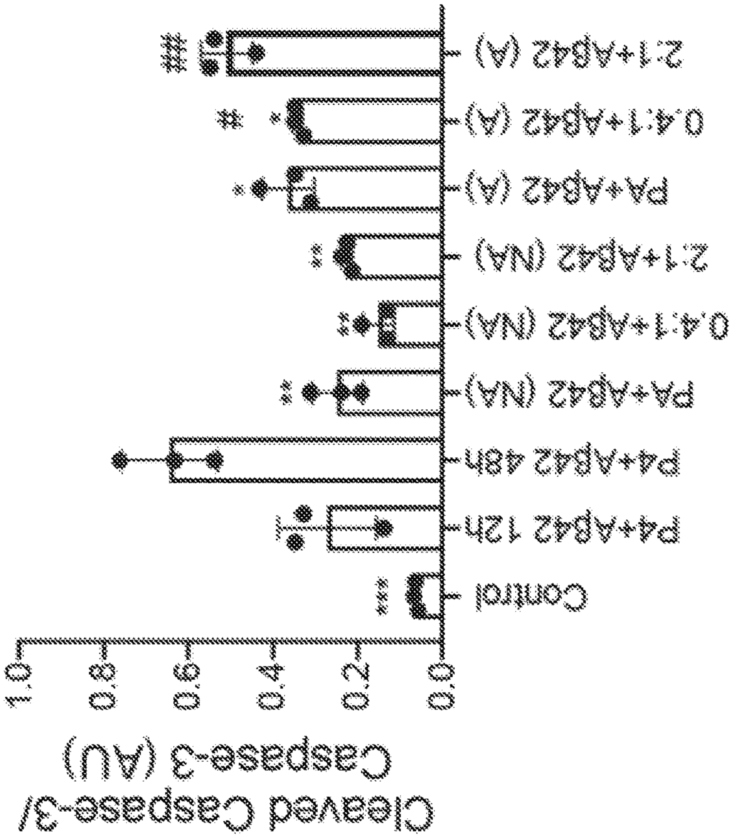
(FIG. 24F) Dot plot representing the normalized protein levels of cleaved caspase-3 at 12 h in the conditions referred. One-way ANOVA with the Bonferroni test is used: *p<0.001, p<0.01, *p<0.05 vs P4+A Aβ42 at 48 h, ###p<0.001, ##p<0.01, vs non-annealed (NA) PAs. Results based on at least three iterations.

Neural death was analyzed by LDH assay and the expression of cleaved caspase-3 by western blot analysis. Caspase-3 is a principal cell death protease involved in neuronal apoptosis during physiological development and under pathological conditions such as AD.[15, 16] As shown in FIG. 23C-E, the administration of Aβ42 alone caused significant cell death manifested by higher LDH activity (FIG. 23C) and a significantly increase of cleaved caspase −3 compared to control condition (no treatment, FIG. 23D, E). P4 condition showed decreased cell death compared to Aβ42 consistent with previous studies reported.[17] Notably, cell neurotoxicity was significantly decreased with the addition of non-annealed PAs. Especially, neuronal cells treated with P4/PA co-assemblies showed significantly lower levels of neurotoxicity, suggesting the synergistic effect of P4 and PA as well as the protective enzymatic effect of PA on P4 preserving its activity (FIG. 23C-E). P4 is more hydrophobic than the peptide segment of PA according to their calculated log P values (Table 1). Log P values were calculated by Molinspiration Cheminformatics.

TABLE 1

LogP values of peptide segment on PA and peptide sequence of P4 at all possible charge states.

| Peptide Sequence | Charge State | LogP |
|---|---|---|
| PA segment | 0 | -4.57 |
| (Ac-$V_3A_3E_3$ | -1 | -5.5 |
| (SEQ ID NO: 47)-$NH_2$) | -2 | -5.46 |
| | -3 | -5.43 |
| P4 | 0 | 0.54 |
| (Ac-LPFFD | | |
| (SEQ ID NO: 45)-$NH_2$) | -1 | -2.18 |

Figure 21A:
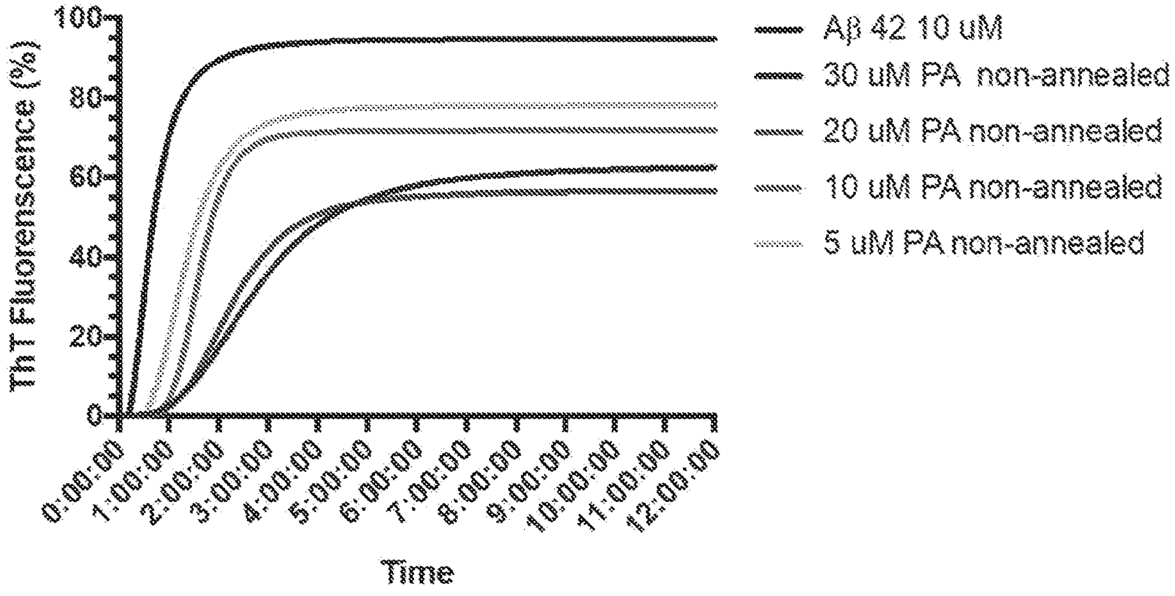
FIG. 21. Aβ42 aggregation kinetics monitored by ThT fluorescence at 37° C. for 12 hours. Incubation starts with 10 μM Aβ42 and aged (FIG. 21A) or annealed (FIG. 21B) PA solution at different concentrations.
Figure 21B:
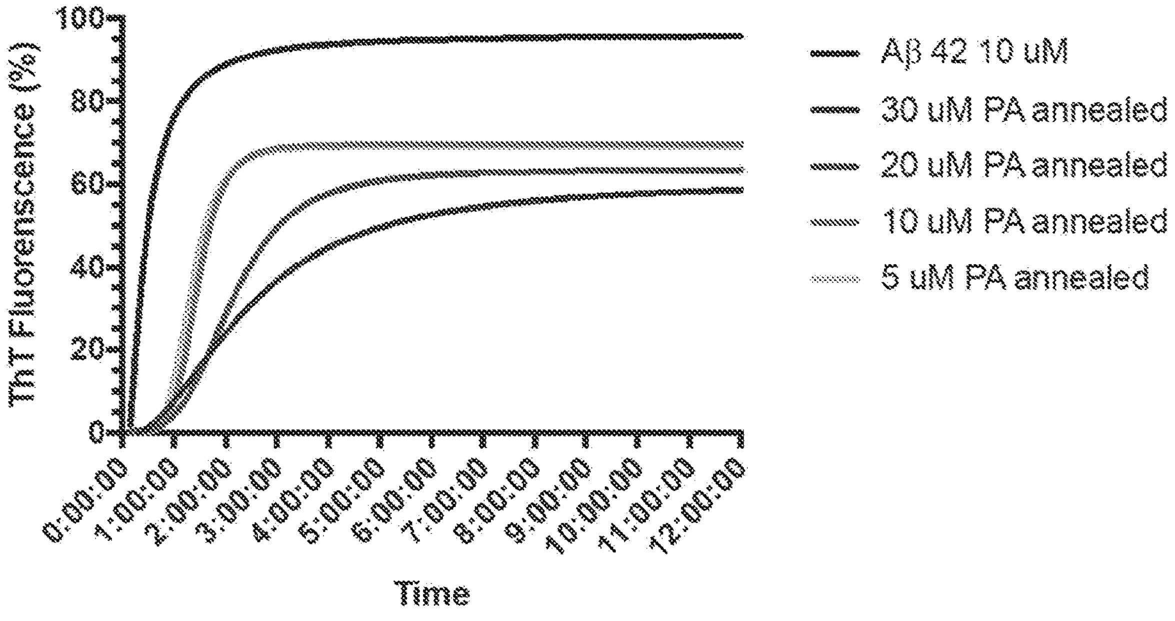

Since Aβ42 is the most hydrophobic component, the increased hydrophobicity of the β-sheet motifs by incorporating P4 into nanofibers may cause greater cohesion between the monomeric Aβ42 and the P4/PA nanostructure, leading to the inhibited aggregation behavior and consequently less neurotoxicity. Finally, when cells were treated with annealed PAs, a significant increase in neural toxicity by LDH and cleaved caspase-3 at 24 and 48 hours was found compared to the treatment with non-annealed PAs, likely due to the reduced interactions between P4 and PA due to the annealing process (FIG. 21). Based on these findings, it was concluded that co-assembly of the amyloid inhibitor P4 with PA significantly enhanced the therapeutic inhibition of Aβ42 neurotoxicity. In particular, the non-annealed co-assemblies, which show more supramolecular interactions between P4 and the PA β-sheet, have better peptide stability and potency compared to the annealed condition, indicating that kinetically trapped supramolecular assemblies can exhibit superior pharmaceutical functions and thus highlighting the importance of supramolecular synthesis pathways.

Demonstrated herein is the potential of a supramolecular peptide assembly to modulate incorporation of a therapeutic peptide through non-covalent interactions. By assembling from the monomeric state, the morphology and internal structure of the co-assemblies are tuned by peptide/PA stoichiometry and the amphiphilicity encoded by peptide sequences. Without annealing, a small amount of added peptide stabilizes the internal structure by displacing water molecules and locating itself between β-sheet motifs. When PA co-assembles with peptide at high concentrations, the peptide tends to suppress β-sheet formation by inhibiting the directional extension of PA hydrogen bonding in the nanostructure. Thermal annealing partially expels the co-assembled peptides into solution phase, indicating that some of the incorporated peptides at non-annealed state are not thermodynamically favored. To understand the generalizability and possible application of our findings, an β-amyloid (Aβ) peptide inhibitor recognized as a drug candidate for AD treatment was applied in the peptide/PA co-assembly supramolecular system. Compared to the therapeutic peptide in soluble form, the peptide/PA co-assemblies have shown elevated inhibitive activity against AP 42 aggregation that leads to profoundly enhanced neuronal cell viability, suggesting the potential of peptide/PA co-assembly as a therapeutic platform in neurodegenerative diseases. The scope of soluble peptides co-assembling with supramolecular systems can be further extended by integrating with computational prediction, which potentially create strategies from a therapeutic point as well as source of novel superstructures.

REFERENCES

1. Tantakitti, F.; Boekhoven, J.; Wang, X.; Kazantsev, R. V.; Yu, T.; Li, J. H.; Zhuang, E.; Zandi, R.; Ortony, J. H.; Newcomb, C. J.; Palmer, L. C.; Shekhawat, G. S.; de la Cruz, M. O.; Schatz, G. C.; Stupp, S. I., Energy landscapes and functions of supramolecular systems. *Nat Mater* 2016, 15 (4), 469-+.
2. Zhang, S. M.; Greenfield, M. A.; Mata, A.; Palmer, L. C.; Bitton, R.; Mantei, J. R.; Aparicio, C.; de la Cruz, M. O.; Stupp, S. I., A self-assembly pathway to aligned monodomain gels. *Nat Mater* 2010, 9 (7), 594-601.
3. Ortony, J. H.; Newcomb, C. J.; Matson, J. B.; Palmer, L. C.; Doan, P. E.; Hoffman, B. M.; Stupp, S. I., Internal dynamics of a supramolecular nanofibre. *Nat Mater* 2014, 13 (8), 812-816.
4. Korevaar, P. A.; Newcomb, C. J.; Meijer, E. W.; Stupp, S. I., Pathway Selection in Peptide Amphiphile Assembly. *Journal of the American Chemical Society* 2014, 136 (24), 8540-8543.
5. Lee, S. S.; Hsu, E. L.; Mendoza, M.; Ghodasra, J.; Nickoli, M. S.; Ashtekar, A.; Polavarapu, M.; Babu, J.; Riaz, R. M.; Nicolas, J. D.; Nelson, D.; Hashmi, S. Z.; Kaltz, S. R.; Earhart, J. S.; Merk, B. R.; McKee, J. S.; Bairstow, S. F.; Shah, R. N.; Hsu, W. K.; Stupp, S. I., Gel scaffolds of BMP-2-binding peptide amphiphile nanofibers for spinal arthrodesis. *Adv Healthc Mater* 2015, 4 (1), 131-141.
6. Cui, H.; Cheetham, A. G.; Pashuck, E. T.; Stupp, S. I., Amino acid sequence in constitutionally isomeric tetrapeptide amphiphiles dictates architecture of one-dimensional nanostructures. *J Am Chem Soc* 2014, 136 (35), 12461-8.
7. Xu, S., Cross-beta-sheet structure in amyloid fiber formation. *J Phys Chem B* 2009, 113 (37), 12447-55.
8. Meisburger, S. P.; Thomas, W. C.; Watkins, M. B.; Ando, N., X-ray Scattering Studies of Protein Structural Dynamics. *Chemical Reviews* 2017, 117 (12), 7615-7672.
9. Matson, J. B.; Newcomb, C. J.; Bitton, R.; Stupp, S. I., Nanostructure-templated control of drug release from peptide amphiphile nanofiber gels. *Soft Matter* 2012, 8 (13), 3586-3595.
10. Rossi, A. M.; Taylor, C. W., Analysis of protein-ligand interactions by fluorescence polarization. *Nature Protocols* 2011, 6 (3).
11. Viola, K. L.; Klein, W. L., Amyloid beta oligomers in Alzheimer's disease pathogenesis, treatment, and diagnosis. *Acta Neuropathol* 2015, 129 (2), 183-206.
12. Walsh, D. M.; Klyubin, I.; Fadeeva, J. V.; Cullen, W. K.; Anwyl, R.; Wolfe, M. S.; Rowan, M. J.; Selkoe, D. J., Naturally secreted oligomers of amyloid beta protein potently inhibit hippocampal long-term potentiation in vivo. *Nature* 2002, 416 (6880), 535-9.
13. Soto, C.; Sigurdsson, E. M.; Morelli, L.; Kumar, R. A.; Castano, E. M.; Frangione, B., Beta-sheet breaker peptides inhibit fibrillogenesis in a rat brain model of amyloidosis: implications for Alzheimer's therapy. *Nat Med* 1998, 4 (7), 822-6.
14. LeVine, H., 3rd, Thioflavine T interaction with synthetic Alzheimer's disease beta-amyloid peptides: detection of amyloid aggregation in solution. *Protein Sci* 1993, 2 (3), 404-10.
15. Han, X. J.; Hu, Y. Y.; Yang, Z. J.; Jiang, L. P.; Shi, S. L.; Li, Y. R.; Guo, M. Y.; Wu, H. L.; Wan, Y. Y., Amyloid beta-42 induces neuronal apoptosis by targeting mitochondria. *Mol Med Rep* 2017, 16 (4), 4521-4528.
16. Kuida, K.; Zheng, T. S.; Na, S.; Kuan, C.; Yang, D.; Karasuyama, H.; Rakic, P.; Flavell, R. A., Decreased apoptosis in the brain and premature lethality in CPP32-deficient mice. *Nature* 1996, 384 (6607), 368-72.
17. De Bona, P.; Giuffrida, M. L.; Caraci, F.; Copani, A.; Pignataro, B.; Attanasio, F.; Cataldo, S.; Pappalardo, G.; Rizzarelli, E., Design and synthesis of new trehalose-conjugated pentapeptides as inhibitors of A beta(1-42) fibrillogenesis and toxicity. *J Pept Sci* 2009, 15 (3), 220-228.

Example 2

The severe acute respiratory syndrome coronavirus 2 (SARS-CoV-2) infection relies on its spike protein binding to angiotensin-converting enzyme 2 (ACE2) on host cells to initiate cellular entry. Blocking the interactions between spike protein and ACE2 offers promising opportunities for developing therapeutics for the prevention or treatment of COVID-19. Here PA assemblies were utilized as a platform co-assembling a peptide fragment sequence from ACE2 binding to SARS-CoV-2 spike receptor binding domain (RBD). The non-covalent incorporation of this peptide sequence into PA nanostructures stabilized the peptide against enzymatic degradation, and more importantly, enables the inhibition of SARS-CoV-2 pseudovirus entry into human host cells. These findings will provide an avenue to designing peptide-based therapeutics for COVID-19.

Figures 25A, 25B:
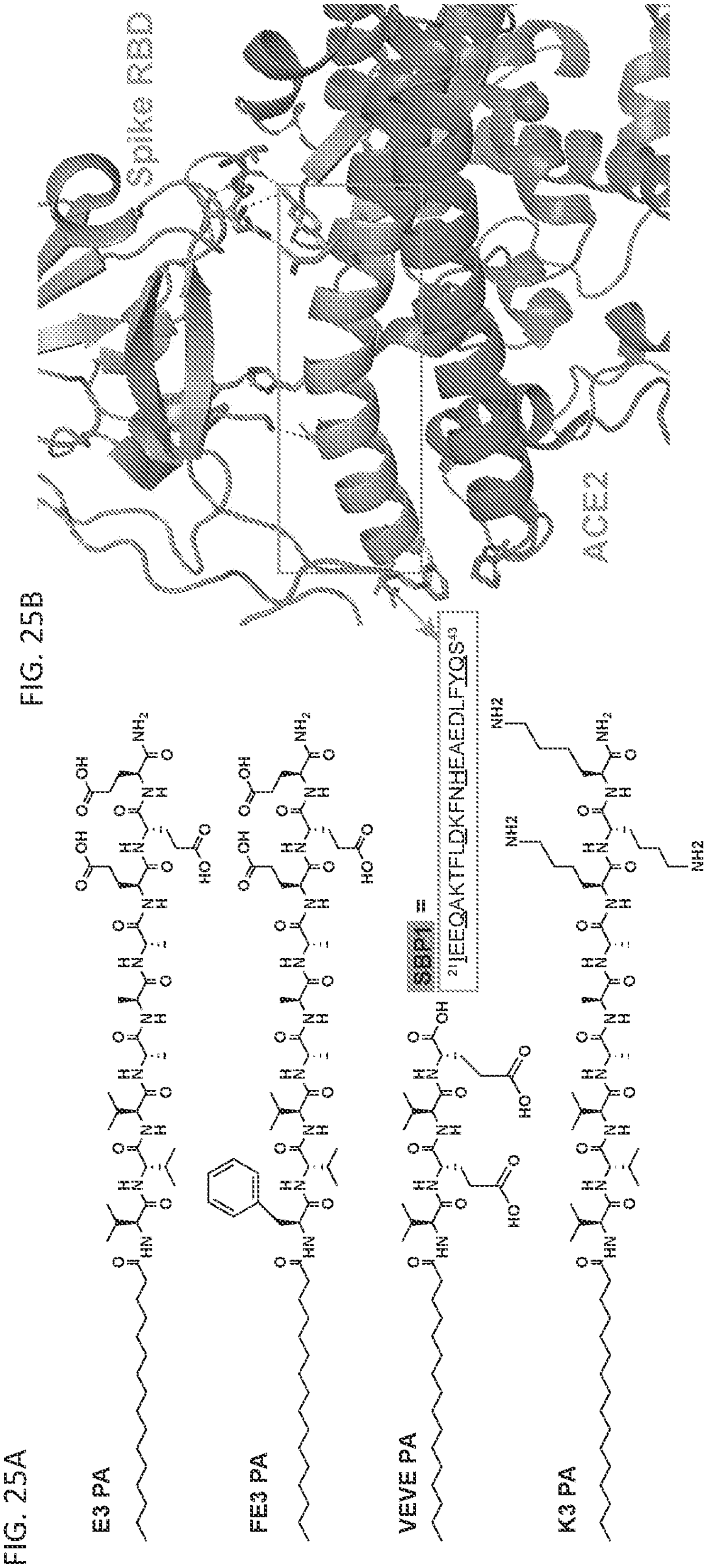
FIG. 25A shows chemical design of peptide amphiphiles (PAs) co-assembling with SBP-1 peptide.
FIG. 25B shows Complex structure of SARS-CoV-2 spike RBD (orange) and ACE2 (blue), (PDB: 6M17, resolution of 2.90 Å), where the SBP-1 (pink) as a partial sequence of ACE2 includes the key residues binding to SARS-CoV-2 spike RBD.

The four PA sequences including $C_{16}$-$V_3A_3E_3$ (SEQ ID NO: 47) ($E_3$ PA), $C_{16}$-$FV_2A_3E_3$ (SEQ ID NO: 48) ($FE_3$ PA), $C_{16}$-VEVE (SEQ ID NO: 49) (VEVE PA) and $C_{16}$-$V_3A_3K_3$ (SEQ ID NO: 50) ($K_3$ PA) were chosen as molecular backbone, owing to their strong propensity of self-assembling into one-dimensional nanostructures in aqueous environment (FIG. 25A). SBP-1 peptide is a 23-mer fragment sequence of ACE2 α-helix domain interfaced with spike RBD through mostly polar contacts (FIG. 25B). SBP-1 is another exemplary free peptide described herein. In contrast to SBP-1 peptide alone that may be vulnerable to enzymatic degradation in water, it was hypothesized that non-covalently incorporated SBP-1 in PA nanostructures can be stabilized and potentially display enhanced biological efficacy.

Figure 26:
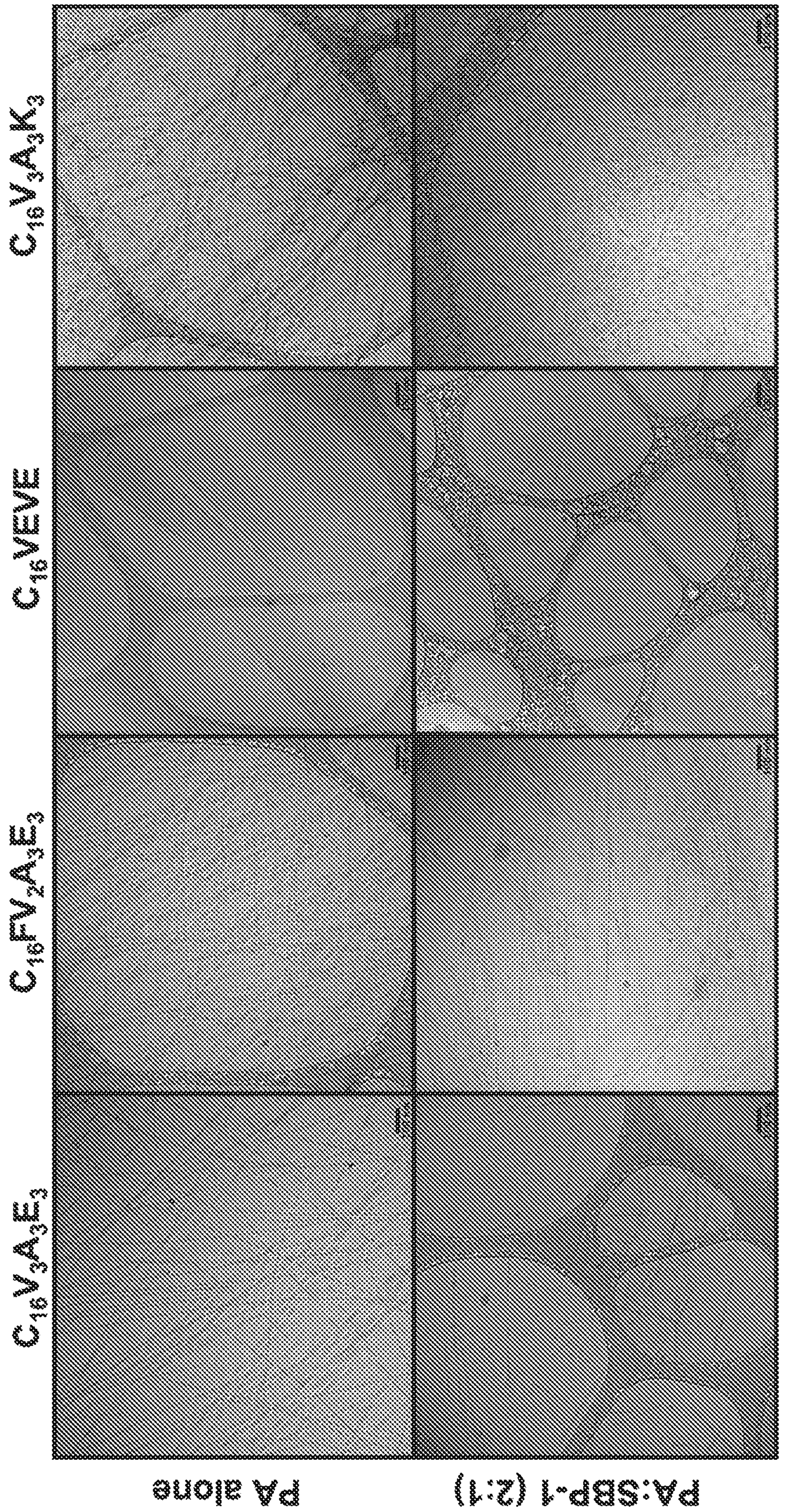
FIG. 26. Cryo-TEM images of self-assembled PA and PA co-assembled with SBP-1 peptide at a molar ratio of PA:SBP1 2:1.
Figure 27A:
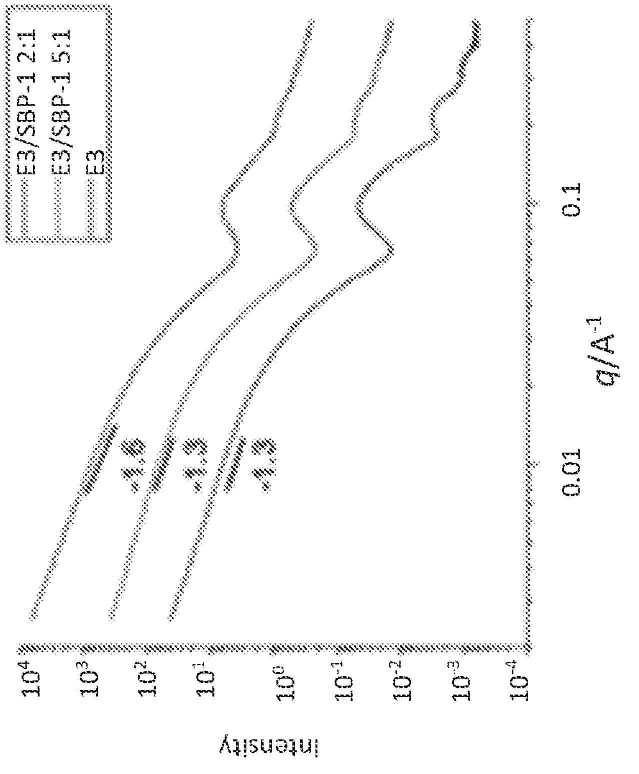
FIG. 27A-27D show SAXS profiles of PA co-assembled with SBP-1 at molar ratio of PA/SBP-1 2:1 or 5:1 and self-assembled PA in aqueous solution. The PA concentration in all conditions was 10 mM.
Figure 27B:
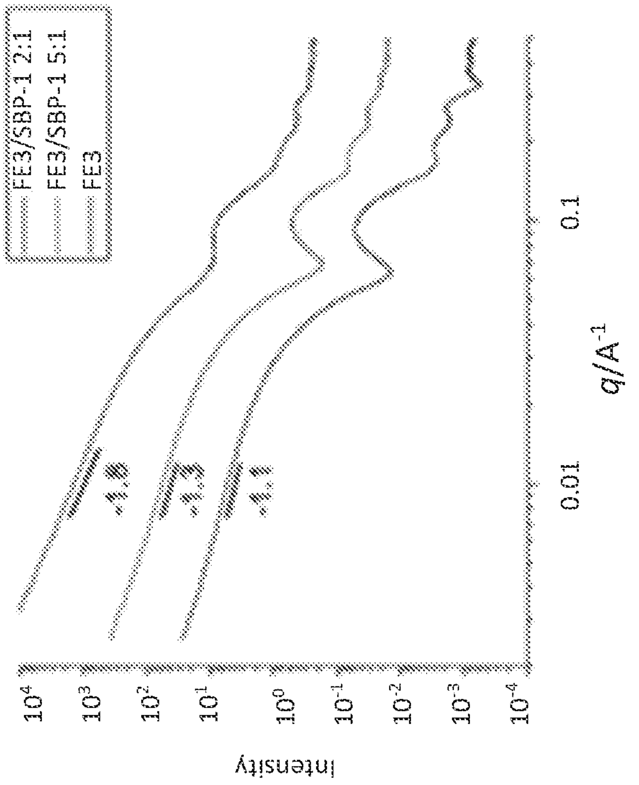
Figure 27C:
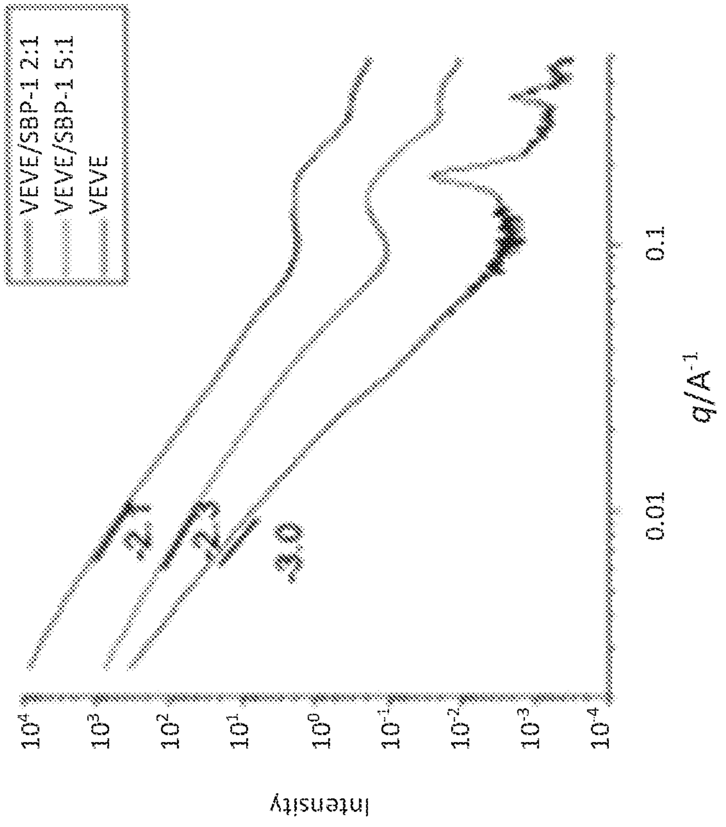
Figure 27D:
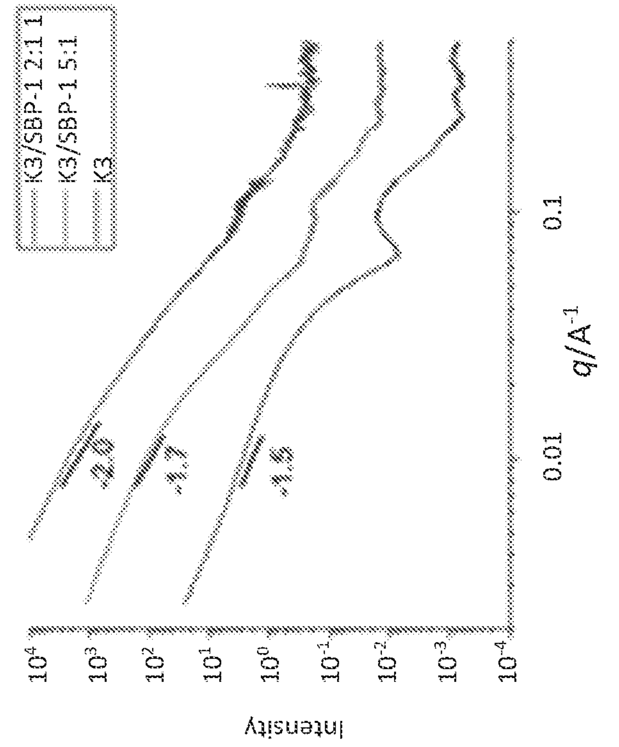
Figure 27E:
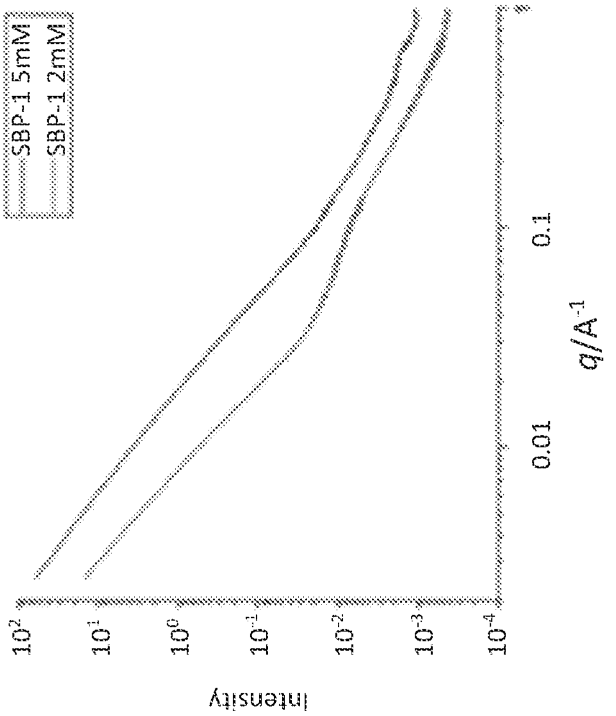
(FIG. 27E) SAXS profiles SBP-1 peptide alone in aqueous solution at corresponding concentrations. Intensities were offset for clarity.

The nanostructures of self-assembled PA as well as co-assembled PA with SBP1 were characterized by cryogenic transmission microscopy (cryo-TEM) imaging (FIG. 26). The $E_3$ PA, $FE_3$ PA and $K_3$ PA self-assembled into nanofibers in water, and VEVE PA formed wide nanoribbons. When these PAs assembled in the presence of SBP-1, the persistency of the nanostructures was reduced, resulting in short nanofibers or narrower nanoribbons. These observations indicate that the SBP-1 as a long peptide may interfere the hydrogen bonding formation between PA molecules, thus inhibiting their nanostructure elongation.

To corroborate the observations on cryo-TEM, solution small-angle X-ray scattering (SAXS) was performed with self-assembled PA, PA/SBP-1 co-assemblies and SBP-1 alone (FIG. 27). For samples with $E_3$ PA, $FE_3$ PA and $K_3$ PA (FIG. 27A-27D), their slopes in Guinier region became more negative when co-assembled with SBP-1; furthermore, the SAXS minimum was diminishing as PA co-assembled with increasing amount of SBP-1. These changes indicate that the incorporation of SBP-1 may cause the aggregation of the nanofibers, leading to increased polydispersity in the supramolecular system. For VEVE PA, the self-assembled PA displayed high crystallinity suggested by the presence of sharp peaks on SAXS spectrum. When co-assembled with SBP-1 peptide, the sharp peaks disappeared, and the negative value of the slopes in Guinier region were smaller, indicating the disruption of the stacked nanoribbons caused by the introduction of SBP-1 peptide. In contrast, SBP-1 peptide alone at corresponding concentrations (FIG. 27E) did not show any features of regular nanostructure on the SAXS profile.

Figure 28A:
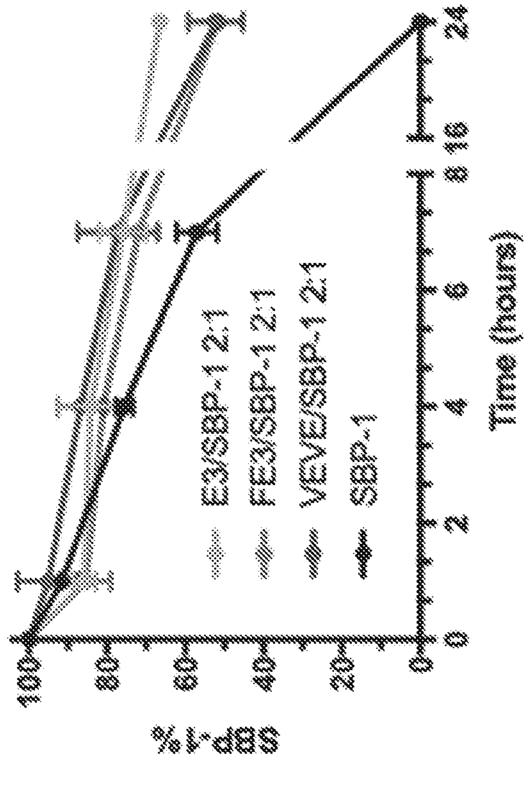
FIG. 28A-28B show Enzymatic degradation of SBP-1 peptide alone or co-assembled with PA by exposing to 0.1 μg/mL α-chymotrypsin at 37° C. for 24 hours.
Figure 28B:
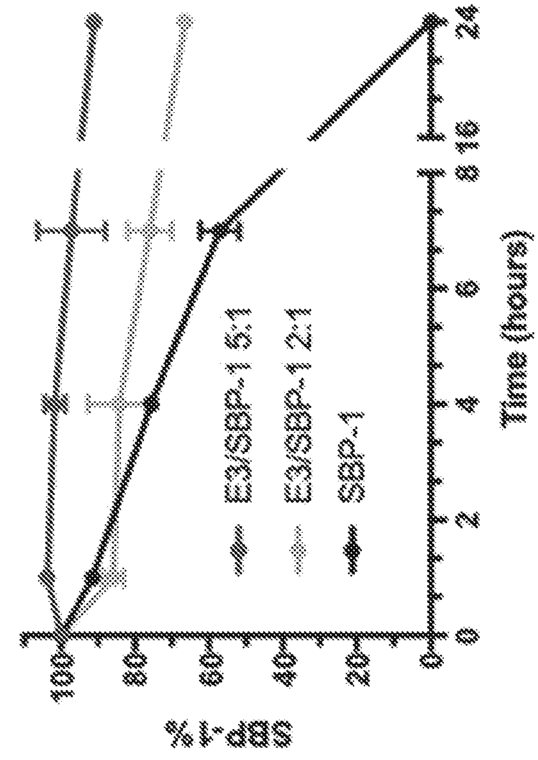

The enzymatic degradation kinetics of SBP-1 peptide were then investigated by exposing α-chymotrypsin over 24 hours. Contrary to SBP-1 peptide alone, which decomposed completely in 24 hours, the PA co-assemblies at PA/SBP-1 2:1 molar ratio (FIG. 28A) were able to preserve SBP-1 peptide at the percentages varying from 50% to 75%. The SBP-1 degradation within $E_3$/SBP-1 co-assemblies at different molar ratios were further assessed (FIG. 28B). By incorporating SBP-1 at a smaller amount ($E_3$/SBP-1 5:1), almost 100% SBP-1 peptide was preserved over the time range of 24 hours. This further validated the role of $E_3$ PA in protecting SBP-1 peptide from enzymatic degradation.

Figure 29A:
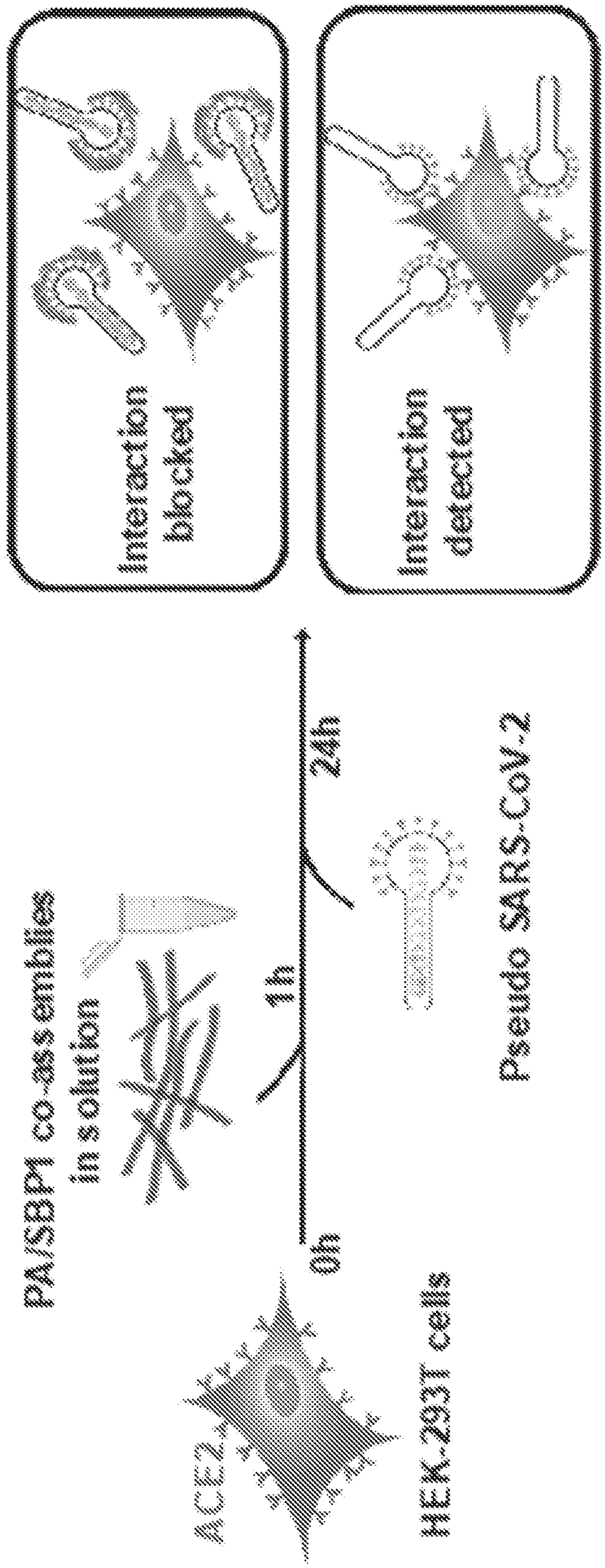
FIG. 29A shows a schematic representation of the experimental design of SARS-CoV-2 pseudovirus infection into ACE2 expressing HEK293T cells.
Figure 29B:
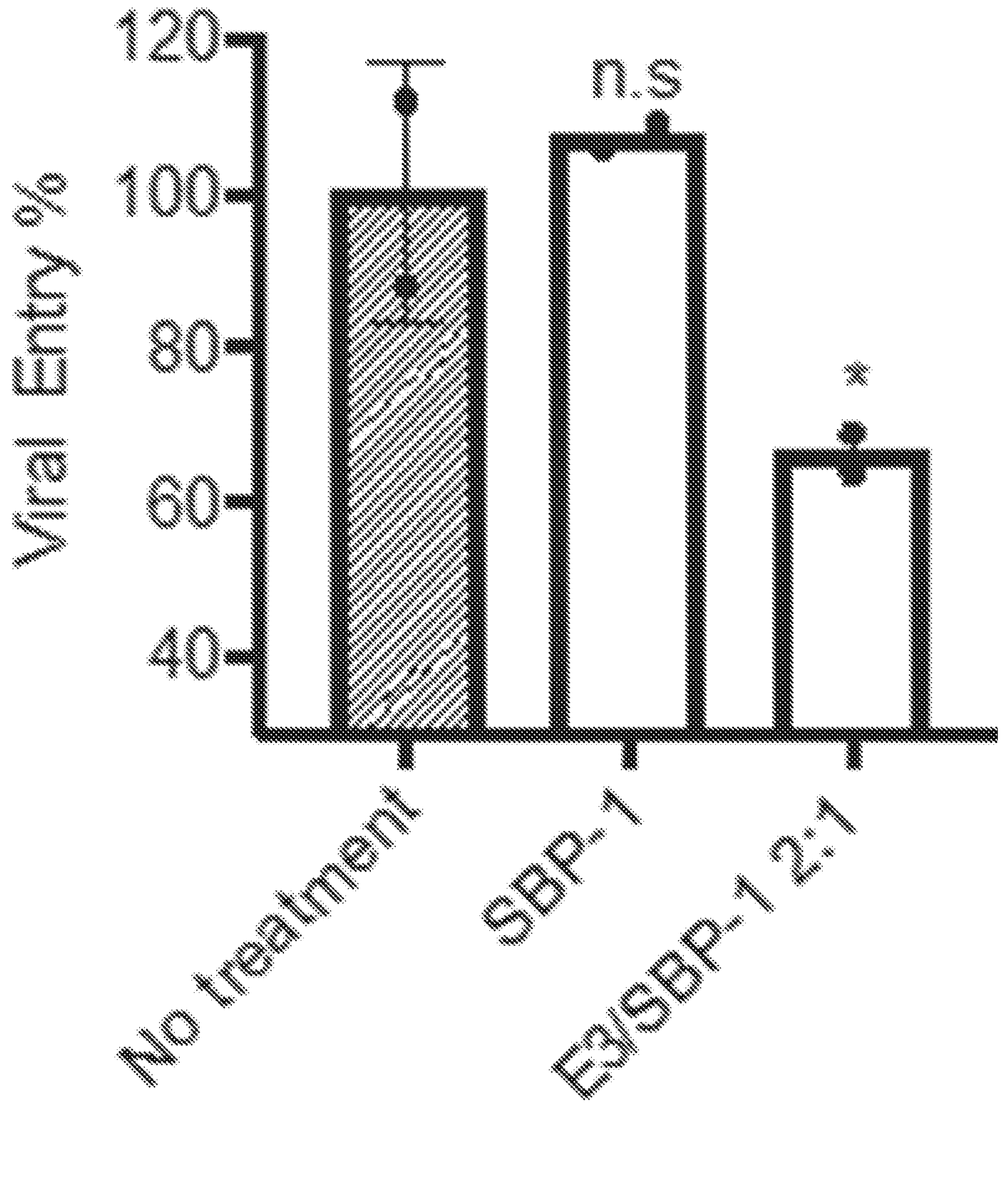
(FIG. 29B) The effect of SBP-1 peptide alone and SBP-1 co-assembled with E3 PA on SARS-CoV-2 pseudovirus entry into cells. One-way ANOVA with the Bonferroni test is used: *p<0.05 vs. no treatment.

Given the protective effect of $E_3$ PA by co-assembling with SBP-1, the biological functions of $E_3$/SBP-1 co-assemblies were then evaluated in vitro. The PA fibers or peptide were first incubated with red fluorescent ACE2 expressing HEK293T cells for an hour, SARS-CoV-2 pseudovirus with green fluorescence coated with spike protein was then added and cultured for 24 hours (FIG. 29A). Cells were cultured in 96-well plate and viral entry was determined by the fluorescence intensity. In relation to no treatment group defined as 100% viral entry, $E_3$/SBP-1 suppressed around 30% of the viral infection. However, SBP-1 alone did not show inhibition activity of viral entry. SBP-1 peptide alone may form irregular aggregates in solution which reduced the accessibility of binding to SARS-CoV-2 RBD. In contrast, co-assembling with $E_3$ PA may help SBP-1 peptide partitioning in the nanofiber, enabling the presentation of SBP-1 peptide as monomers with biological efficacy of inhibiting SARS-CoV-2 viral infection.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

The invention claimed is:

1. A nanostructure comprising a peptide amphiphile and a free peptide, wherein the peptide amphiphile comprises a hydrophobic tail comprising a chain of 8 to 24 carbons, a structural peptide segment having a propensity for forming β-sheet conformations, and a charged peptide segment comprising E, EE, EEE, EEEE (SEQ ID NO: 43, wherein the free peptide comprises LPFFD (SEQ ID NO: 45), or KLVFF (SEQ ID NO: 46, and wherein the free peptide and the peptide amphiphile are non-covalently co-assembled within the nanostructure.

2. The nanostructure of claim 1, wherein the structural peptide segment comprises four or more consecutive V and/or A residues.

3. The nanostructure of claim 1, wherein the structural peptide segment comprises $V_2A_2$ (SEQ ID NO: 51), $V_2A_3$ (SEQ ID NO: 52), $V_3A_3$ (SEQ ID NO: 53), or VEV.

4. The nanostructure of claim 1, wherein the charged peptide segment comprises EEE.

5. The nanostructure of claim 1, wherein the peptide amphiphile comprises $C_{8\text{-}24}$-$V_3A_3E_3$ (SEQ ID NO: 47).

6. A method of treating or preventing a neurodegenerative disorder in a subject, the method comprising providing to the subject a composition comprising the nanostructure of claim 1.

7. The method of claim 6, wherein the structural peptide segment comprises $V_2A_2$ (SEQ ID NO: 51), $V_2A_3$ (SEQ ID NO: 52), or $V_3A_3$ (SEQ ID NO: 53) and the charged peptide segment comprises EE, EEE, or EEEE (SEQ ID NO:43).

8. The method of claim 6, wherein the neurodegenerative disorder is selected from Alzheimer's disease, Parkinson's disease, and Huntington's disease.

* * * * *

SEQUENCE LISTING

```
<160> NUMBER OF SEQ ID NOS: 56

<210> SEQ ID NO 1
<211> LENGTH: 23
<212> TYPE: PRT
<213> ORGANISM: Artificial Sequence
<220> FEATURE:
<223> OTHER INFORMATION: Synthetic

<400> SEQUENCE: 1

Ile Glu Glu Gln Ala Lys Thr Phe Leu Asp Lys Phe Asn His Glu Ala
1               5                   10                  15

Glu Asp Leu Phe Tyr Gln Ser
            20


<210> SEQ ID NO 2
<211> LENGTH: 23
<212> TYPE: PRT
<213> ORGANISM: Artificial Sequence
<220> FEATURE:
<223> OTHER INFORMATION: Synthetic

<400> SEQUENCE: 2

Glu Glu Gln Ala Lys Thr Phe Leu Asp Lys Phe Asn His Glu Ala Glu
1               5                   10                  15

Asp Leu Phe Tyr Gln Ser Ser
            20


<210> SEQ ID NO 3
```

<211> LENGTH: 36
<212> TYPE: PRT
<213> ORGANISM: Artificial Sequence
<220> FEATURE:
<223> OTHER INFORMATION: Synthetic

<400> SEQUENCE: 3

```
Glu Glu Gln Ala Lys Thr Phe Leu Asp Lys Phe Asn His Glu Ala Glu
1               5                   10                  15

Asp Leu Phe Tyr Gln Ser Ser Leu Ala Ser Trp Asn Tyr Asn Thr Asn
            20                  25                  30

Ile Thr Glu Glu
        35
```

<210> SEQ ID NO 4
<211> LENGTH: 21
<212> TYPE: PRT
<213> ORGANISM: Artificial Sequence
<220> FEATURE:
<223> OTHER INFORMATION: Synthetic

<400> SEQUENCE: 4

```
Pro Thr Thr Lys Phe Met Leu Lys Tyr Asp Glu Asn Gly Thr Ile Thr
1               5                   10                  15

Asp Ala Val Asp Cys
            20
```

<210> SEQ ID NO 5
<211> LENGTH: 21
<212> TYPE: PRT
<213> ORGANISM: Artificial Sequence
<220> FEATURE:
<223> OTHER INFORMATION: Synthetic

<400> SEQUENCE: 5

```
Tyr Gln Asp Val Asn Cys Thr Asp Val Ser Pro Thr Ala Ile His Ala
1               5                   10                  15

Asp Gln Leu Thr Pro
            20
```

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

```
Gln Tyr Gly Ser Phe Cys Thr Ala Gln Leu Asn Arg Ala Leu Ser Gly
1               5                   10                  15

Ile Ala Ala Val Glu Gln
            20
```

<210> SEQ ID NO 7
<211> LENGTH: 160
<212> TYPE: PRT
<213> ORGANISM: Artificial Sequence
<220> FEATURE:
<223> OTHER INFORMATION: Synthetic

<400> SEQUENCE: 7

```
Asp Glu Asp Leu Glu Glu Leu Glu Arg Leu Tyr Arg Lys Ala Glu Glu
1               5                   10                  15

Val Ala Lys Glu Ala Lys Asp Ala Ser Arg Arg Gly Asp Asp Glu Arg
```

```
            20                  25                  30

Ala Lys Glu Gln Met Glu Arg Ala Met Arg Leu Phe Asp Gln Val Phe
        35                  40                  45

Glu Leu Ala Gln Glu Leu Gln Glu Lys Gln Thr Asp Gly Asn Arg Gln
    50                  55                  60

Lys Ala Thr His Leu Asp Lys Ala Val Lys Glu Ala Ala Asp Glu Leu
65                  70                  75                  80

Tyr Gln Arg Val Arg Glu Leu Glu Glu Gln Val Met His Val Leu Asp
                85                  90                  95

Gln Val Ser Glu Leu Ala His Glu Leu Leu His Lys Leu Thr Gly Glu
            100                 105                 110

Glu Leu Glu Arg Ala Ala Tyr Phe Asn Trp Trp Ala Thr Glu Met Met
        115                 120                 125

Leu Glu Leu Ile Lys Ser Asp Asp Glu Arg Glu Ile Arg Glu Ile Glu
    130                 135                 140

Glu Glu Ala Arg Arg Ile Leu Glu His Leu Glu Glu Leu Ala Arg Lys
145                 150                 155                 160


<210> SEQ ID NO 8
<211> LENGTH: 75
<212> TYPE: PRT
<213> ORGANISM: Artificial Sequence
<220> FEATURE:
<223> OTHER INFORMATION: Synthetic

<400> SEQUENCE: 8

Glu Leu Glu Glu Gln Val Met His Val Leu Asp Gln Val Ser Glu Leu
1               5                   10                  15

Ala His Glu Leu Leu His Lys Leu Thr Gly Glu Glu Leu Glu Arg Ala
            20                  25                  30

Ala Tyr Phe Asn Trp Trp Ala Thr Glu Met Met Leu Glu Leu Ile Lys
        35                  40                  45

Ser Asp Asp Glu Arg Glu Ile Arg Glu Ile Glu Glu Glu Ala Arg Arg
    50                  55                  60

Ile Leu Glu His Leu Glu Glu Leu Ala Arg Lys
65                  70                  75


<210> SEQ ID NO 9
<211> LENGTH: 56
<212> TYPE: PRT
<213> ORGANISM: Artificial Sequence
<220> FEATURE:
<223> OTHER INFORMATION: Synthetic

<400> SEQUENCE: 9

Asp Lys Glu Trp Ile Leu Gln Lys Ile Tyr Glu Ile Met Arg Leu Leu
1               5                   10                  15

Asp Glu Leu Gly His Ala Glu Ala Ser Met Arg Val Ser Asp Leu Ile
            20                  25                  30

Tyr Glu Phe Met Lys Lys Gly Asp Glu Arg Leu Leu Glu Glu Ala Glu
        35                  40                  45

Arg Leu Leu Glu Glu Val Glu Arg
    50                  55


<210> SEQ ID NO 10
<211> LENGTH: 64
<212> TYPE: PRT
<213> ORGANISM: Artificial Sequence
<220> FEATURE:
```

<223> OTHER INFORMATION: Synthetic

<400> SEQUENCE: 10

```
Asn Asp Asp Glu Leu His Met Leu Met Thr Asp Leu Val Tyr Glu Ala
1               5                   10                  15

Leu His Phe Ala Lys Asp Glu Glu Ile Lys Lys Arg Val Phe Gln Leu
            20                  25                  30

Phe Glu Leu Ala Asp Lys Ala Tyr Lys Asn Asn Asp Arg Gln Lys Leu
        35                  40                  45

Glu Lys Val Val Glu Glu Leu Lys Glu Leu Leu Glu Arg Leu Leu Ser
    50                  55                  60
```

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

```
Tyr Lys Tyr Arg Tyr Leu
1               5
```

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

```
Gly Phe Leu Tyr Val Tyr Lys Gly Tyr Gln Pro Ile
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

```
Phe Tyr Thr Thr Thr Gly Ile Gly Tyr Gln Pro Tyr
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

```
Ser Thr Ser Gln Lys Ser Ile Val Ala Tyr Thr Met
1               5                   10
```

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

```
Ala Leu Asn Cys Tyr Trp Pro Leu Asn Asp Tyr Gly Phe Thr Thr Thr
```

-continued

```
1               5                   10                  15

Gly Ile Gly Tyr Gln Pro Tyr Arg Val Val Val Leu Ser Phe Glu Leu
            20                  25                  30


<210> SEQ ID NO 16
<211> LENGTH: 26
<212> TYPE: PRT
<213> ORGANISM: Artificial Sequence
<220> FEATURE:
<223> OTHER INFORMATION: Synthetic

<400> SEQUENCE: 16

Gly Asp Tyr Ser His Cys Ser Pro Leu Arg Tyr Tyr Pro Trp Trp Lys
1               5                   10                  15

Cys Thr Tyr Pro Asp Pro Glu Gly Gly Gly
            20                  25


<210> SEQ ID NO 17
<211> LENGTH: 58
<212> TYPE: PRT
<213> ORGANISM: Artificial Sequence
<220> FEATURE:
<223> OTHER INFORMATION: Synthetic

<400> SEQUENCE: 17

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55


<210> SEQ ID NO 18
<211> LENGTH: 30
<212> TYPE: PRT
<213> ORGANISM: Artificial Sequence
<220> FEATURE:
<223> OTHER INFORMATION: Synthetic

<400> SEQUENCE: 18

Asn Gly Ala Ile Cys Trp Gly Pro Cys Pro Thr Ala Phe Arg Gln Ile
1               5                   10                  15

Gly Asn Cys Gly His Phe Lys Val Arg Cys Cys Lys Ile Arg
            20                  25                  30


<210> SEQ ID NO 19
<211> LENGTH: 30
<212> TYPE: PRT
<213> ORGANISM: Artificial Sequence
<220> FEATURE:
<223> OTHER INFORMATION: Synthetic

<400> SEQUENCE: 19

Asn Gly Ala Ile Cys Trp Gly Pro Cys Pro Thr Ala Phe Arg Gln Ile
1               5                   10                  15

Gly Asn Cys Gly Arg Phe Arg Val Arg Cys Cys Arg Ile Arg
            20                  25                  30


<210> SEQ ID NO 20
<211> LENGTH: 50
<212> TYPE: PRT
```

<213> ORGANISM: Artificial Sequence
<220> FEATURE:
<223> OTHER INFORMATION: Synthetic

<400> SEQUENCE: 20

Val Val Glu Gln Tyr Asn Gln Thr Ile Leu Asn Leu Thr Ser Glu Ile
1 5 10 15

Ser Thr Leu Glu Asn Lys Ser Ala Glu Leu Asn Tyr Thr Val Gln Lys
20 25 30

Leu Gln Thr Leu Ile Asp Asn Ile Asn Ser Thr Leu Val Asp Leu Lys
35 40 45

Trp Leu
50

<210> SEQ ID NO 21
<211> LENGTH: 35
<212> TYPE: PRT
<213> ORGANISM: Artificial Sequence
<220> FEATURE:
<223> OTHER INFORMATION: Synthetic

<400> SEQUENCE: 21

Leu Thr Gln Ile Asn Thr Thr Leu Leu Asp Leu Thr Tyr Glu Met Leu
1 5 10 15

Ser Leu Gln Gln Val Val Lys Ala Leu Asn Glu Ser Tyr Ile Asp Leu
20 25 30

Lys Glu Leu
35

<210> SEQ ID NO 22
<211> LENGTH: 36
<212> TYPE: PRT
<213> ORGANISM: Artificial Sequence
<220> FEATURE:
<223> OTHER INFORMATION: Synthetic

<400> SEQUENCE: 22

Ser Leu Thr Gln Ile Asn Thr Thr Leu Leu Asp Leu Thr Tyr Glu Met
1 5 10 15

Leu Ser Leu Gln Gln Val Val Lys Ala Leu Asn Glu Ser Tyr Ile Asp
20 25 30

Leu Lys Glu Leu
35

<210> SEQ ID NO 23
<211> LENGTH: 37
<212> TYPE: PRT
<213> ORGANISM: Artificial Sequence
<220> FEATURE:
<223> OTHER INFORMATION: Synthetic

<400> SEQUENCE: 23

Gly Ile Asn Ala Ser Val Val Asn Ile Gln Lys Glu Ile Asp Arg Leu
1 5 10 15

Asn Glu Val Ala Lys Asn Leu Asn Glu Ser Leu Ile Asp Leu Gln Glu
20 25 30

Leu Gly Lys Tyr Glu
35

<210> SEQ ID NO 24
<211> LENGTH: 68
<212> TYPE: PRT

```
<213> ORGANISM: Artificial Sequence
<220> FEATURE:
<223> OTHER INFORMATION: Synthetic

<400> SEQUENCE: 24

Glu Leu Asp Ser Phe Lys Glu Glu Leu Asp Lys Tyr Phe Lys Asn His
1               5                   10                  15

Thr Ser Pro Asp Val Asp Leu Gly Asp Ile Ser Gly Ile Asn Ala Ser
            20                  25                  30

Val Val Asn Ile Gln Lys Glu Ile Asp Arg Leu Asn Glu Val Ala Lys
        35                  40                  45

Asn Leu Asn Glu Ser Leu Ile Asp Leu Gln Glu Leu Gly Lys Tyr Glu
    50                  55                  60

Gln Tyr Ile Lys
65


<210> SEQ ID NO 25
<211> LENGTH: 38
<212> TYPE: PRT
<213> ORGANISM: Artificial Sequence
<220> FEATURE:
<223> OTHER INFORMATION: Synthetic

<400> SEQUENCE: 25

Asn Gly Ile Gly Val Thr Gln Asn Val Leu Tyr Glu Asn Gln Lys Gln
1               5                   10                  15

Ile Ala Asn Gln Phe Asn Lys Ala Ile Ser Gln Ile Gln Glu Ser Leu
            20                  25                  30

Thr Thr Thr Ser Thr Ala
        35


<210> SEQ ID NO 26
<211> LENGTH: 27
<212> TYPE: PRT
<213> ORGANISM: Artificial Sequence
<220> FEATURE:
<223> OTHER INFORMATION: Synthetic

<400> SEQUENCE: 26

Ile Gln Lys Glu Ile Asp Arg Leu Asn Glu Val Ala Lys Asn Leu Asn
1               5                   10                  15

Glu Ser Leu Ile Asp Leu Gln Glu Leu Gly Lys
            20                  25


<210> SEQ ID NO 27
<211> LENGTH: 38
<212> TYPE: PRT
<213> ORGANISM: Artificial Sequence
<220> FEATURE:
<223> OTHER INFORMATION: Synthetic

<400> SEQUENCE: 27

Gly Asp Ile Ser Gly Ile Asn Ala Ser Val Val Asn Ile Gln Lys Glu
1               5                   10                  15

Ile Asp Arg Leu Asn Glu Val Ala Lys Asn Leu Asn Glu Ser Leu Ile
            20                  25                  30

Asp Leu Gln Glu Leu Gly
        35


<210> SEQ ID NO 28
<211> LENGTH: 28
<212> TYPE: PRT
```

```
<213> ORGANISM: Artificial Sequence
<220> FEATURE:
<223> OTHER INFORMATION: Synthetic

<400> SEQUENCE: 28

Tyr Glu Asn Gln Lys Gln Ile Ala Asn Gln Phe Asn Lys Ala Ile Ser
1               5                   10                  15

Gln Ile Gln Glu Ser Leu Thr Thr Thr Ser Thr Ala
            20                  25


<210> SEQ ID NO 29
<211> LENGTH: 48
<212> TYPE: PRT
<213> ORGANISM: Artificial Sequence
<220> FEATURE:
<223> OTHER INFORMATION: Synthetic

<400> SEQUENCE: 29

Asp Val Asp Leu Gly Asp Ile Ser Gly Ile Asn Ala Ser Val Val Asn
1               5                   10                  15

Ile Gln Lys Glu Ile Asp Arg Leu Asn Glu Val Ala Lys Asn Leu Asn
            20                  25                  30

Glu Ser Leu Ile Asp Leu Gln Glu Leu Gly Lys Tyr Glu Gln Tyr Ile
        35                  40                  45


<210> SEQ ID NO 30
<211> LENGTH: 35
<212> TYPE: PRT
<213> ORGANISM: Artificial Sequence
<220> FEATURE:
<223> OTHER INFORMATION: Synthetic

<400> SEQUENCE: 30

Ile Ser Gly Ile Asn Ala Ser Val Val Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu Leu
        35


<210> SEQ ID NO 31
<211> LENGTH: 36
<212> TYPE: PRT
<213> ORGANISM: Artificial Sequence
<220> FEATURE:
<223> OTHER INFORMATION: Synthetic

<400> SEQUENCE: 31

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu
        35


<210> SEQ ID NO 32
<211> LENGTH: 36
<212> TYPE: PRT
<213> ORGANISM: Artificial Sequence
<220> FEATURE:
<223> OTHER INFORMATION: Synthetic

<400> SEQUENCE: 32
```

```
Asp Ile Ser Gly Ile Asn Ala Ser Val Val Asn Ile Gln Lys Glu Ile
1               5                   10                  15

Asp Arg Leu Asn Glu Val Ala Lys Asn Leu Asn Glu Ser Leu Ile Asp
            20                  25                  30

Leu Gln Glu Leu
        35


<210> SEQ ID NO 33
<211> LENGTH: 34
<212> TYPE: PRT
<213> ORGANISM: Artificial Sequence
<220> FEATURE:
<223> OTHER INFORMATION: Synthetic

<400> SEQUENCE: 33

Asp Ile Ser Gly Ile Asn Ala Ser Trp Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu


<210> SEQ ID NO 34
<211> LENGTH: 41
<212> TYPE: PRT
<213> ORGANISM: Artificial Sequence
<220> FEATURE:
<223> OTHER INFORMATION: Synthetic

<400> SEQUENCE: 34

Ser Leu Asp Gln Ile Asn Val Thr Phe Leu Asp Leu Glu Tyr Glu Met
1               5                   10                  15

Lys Lys Leu Glu Glu Ala Ile Lys Lys Leu Glu Glu Ser Tyr Ile Asp
            20                  25                  30

Leu Lys Glu Leu Gly Ser Gly Ser Gly
        35                  40


<210> SEQ ID NO 35
<211> LENGTH: 36
<212> TYPE: PRT
<213> ORGANISM: Artificial Sequence
<220> FEATURE:
<223> OTHER INFORMATION: Synthetic

<400> SEQUENCE: 35

Ile Ser Gly Ile Asn Ala Ser Val Val Asn Ile Gln Lys Glu Ile Asp
1               5                   10                  15

Arg Leu Asn Glu Val Ala Lys Asn Leu Asn Glu Ser Leu Ile Asp Leu
            20                  25                  30

Gln Glu Leu Lys
        35


<210> SEQ ID NO 36
<211> LENGTH: 21
<212> TYPE: PRT
<213> ORGANISM: Artificial Sequence
<220> FEATURE:
<223> OTHER INFORMATION: Synthetic

<400> SEQUENCE: 36

Gly Ile Gly Val Thr Ala Gln Asn Val Leu Tyr Glu Asn Gln Lys Gln
1               5                   10                  15

Ile Ala Asn Gln Phe
```

20

<210> SEQ ID NO 37
<211> LENGTH: 21
<212> TYPE: PRT
<213> ORGANISM: Artificial Sequence
<220> FEATURE:
<223> OTHER INFORMATION: Synthetic

<400> SEQUENCE: 37

Ile Gln Lys Glu Glu Ile Asp Arg Leu Asn Glu Val Ala Lys Asn Leu
1 5 10 15

Asn Glu Ser Leu Ile
20

<210> SEQ ID NO 38
<211> LENGTH: 22
<212> TYPE: PRT
<213> ORGANISM: Artificial Sequence
<220> FEATURE:
<223> OTHER INFORMATION: Synthetic

<400> SEQUENCE: 38

Gly Tyr His Leu Met Ser Phe Pro Gln Ala Ala Pro His Gly Val Val
1 5 10 15

Phe Leu His Val Thr Trp
20

<210> SEQ ID NO 39
<211> LENGTH: 19
<212> TYPE: PRT
<213> ORGANISM: Artificial Sequence
<220> FEATURE:
<223> OTHER INFORMATION: Synthetic

<400> SEQUENCE: 39

Gly Val Phe Val Phe Asn Gly Thr Ser Trp Phe Ile Thr Gln Arg Asn
1 5 10 15

Phe Phe Ser

<210> SEQ ID NO 40
<211> LENGTH: 28
<212> TYPE: PRT
<213> ORGANISM: Artificial Sequence
<220> FEATURE:
<223> OTHER INFORMATION: Synthetic

<400> SEQUENCE: 40

Ala Ala Cys Glu Val Ala Lys Asn Leu Asn Glu Ser Leu Ile Asp Leu
1 5 10 15

Gln Glu Leu Gly Lys Tyr Glu Gln Tyr Ile Lys Trp
20 25

<210> SEQ ID NO 41
<211> LENGTH: 19
<212> TYPE: PRT
<213> ORGANISM: Artificial Sequence
<220> FEATURE:
<223> OTHER INFORMATION: Synthetic

<400> SEQUENCE: 41

Met Trp Lys Thr Pro Thr Leu Lys Tyr Phe Gly Gly Phe Asn Phe Ser
1 5 10 15

Gln Ile Leu

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Ala Thr Ala Gly Trp Thr Phe Gly Ala Gly Ala Ala Leu Gln Ile Pro
1 5 10 15

Phe Ala Met Gln Met Ala Tyr
20

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Glu Glu Glu Glu
1

<210> SEQ ID NO 44
<211> LENGTH: 4
<212> TYPE: PRT
<213> ORGANISM: Artificial Sequence
<220> FEATURE:
<223> OTHER INFORMATION: Synthetic

<400> SEQUENCE: 44

Lys Lys Lys Lys
1

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Leu Pro Phe Phe Asp
1 5

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Lys Leu Val Phe Phe
1 5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Val Val Val Ala Ala Ala Glu Glu Glu
1 5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Phe Val Val Ala Ala Ala Glu Glu Glu
1 5

<210> SEQ ID NO 49
<211> LENGTH: 4
<212> TYPE: PRT
<213> ORGANISM: Artificial Sequence
<220> FEATURE:
<223> OTHER INFORMATION: Synthetic

<400> SEQUENCE: 49

Val Glu Val Glu
1

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Val Val Val Ala Ala Ala Lys Lys Lys
1 5

<210> SEQ ID NO 51
<211> LENGTH: 4
<212> TYPE: PRT
<213> ORGANISM: Artificial Sequence
<220> FEATURE:
<223> OTHER INFORMATION: Synthetic

<400> SEQUENCE: 51

Val Val Ala Ala
1

<210> SEQ ID NO 52
<211> LENGTH: 5
<212> TYPE: PRT
<213> ORGANISM: Artificial Sequence
<220> FEATURE:
<223> OTHER INFORMATION: Synthetic

<400> SEQUENCE: 52

Val Val Ala Ala Ala
1 5

<210> SEQ ID NO 53
<211> LENGTH: 6
<212> TYPE: PRT
<213> ORGANISM: Artificial Sequence
<220> FEATURE:
<223> OTHER INFORMATION: Synthetic

<400> SEQUENCE: 53

Val Val Val Ala Ala Ala

-continued 1 5

<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Ala Ala Val Val
1

<210> SEQ ID NO 55
<211> LENGTH: 6
<212> TYPE: PRT
<213> ORGANISM: Artificial Sequence
<220> FEATURE:
<223> OTHER INFORMATION: Synthetic

<400> SEQUENCE: 55

Ala Ala Ala Val Val Val
1 5

<210> SEQ ID NO 56
<211> LENGTH: 6
<212> TYPE: PRT
<213> ORGANISM: Artificial Sequence
<220> FEATURE:
<223> OTHER INFORMATION: Synthetic

<400> SEQUENCE: 56

Ala Ala Ala Glu Glu Glu
1 5